(12) United States Patent
Spallitta

(10) Patent No.: US 10,709,135 B2
(45) Date of Patent: *Jul. 14, 2020

(54) ORGANOPHOSPHATES FOR TREATING AFFLICTIONS OF THE SKIN

(71) Applicant: ATTILLAPS HOLDINGS, Denver, CO (US)

(72) Inventor: Frank Anthony Spallitta, Denver, CO (US)

(73) Assignee: Attillaps Holdings, Denver, CO (US)

(*) Notice: Subject to any disclaimer, the term of this patent is extended or adjusted under 35 U.S.C. 154(b) by 3 days.

This patent is subject to a terminal disclaimer.

(21) Appl. No.: 14/444,748

(22) Filed: Jul. 28, 2014

(65) Prior Publication Data
US 2015/0086596 A1 Mar. 26, 2015

Related U.S. Application Data

(60) Provisional application No. 61/859,572, filed on Jul. 29, 2013, provisional application No. 61/861,072, filed on Aug. 1, 2013, provisional application No. 61/953,290, filed on Mar. 14, 2014.

(51) Int. Cl.

| | | |
|---|---|---|
| A61K 31/27 | (2006.01) |
| A01N 57/20 | (2006.01) |
| A01N 57/12 | (2006.01) |
| A61K 31/661 | (2006.01) |
| A61N 5/06 | (2006.01) |
| A61K 31/664 | (2006.01) |
| A01N 57/28 | (2006.01) |
| A01N 57/14 | (2006.01) |
| A61K 9/00 | (2006.01) |
| A61K 47/36 | (2006.01) |
| A61K 9/20 | (2006.01) |
| A61K 9/10 | (2006.01) |
| A61K 9/48 | (2006.01) |
| A61K 9/02 | (2006.01) |
| A61K 31/662 | (2006.01) |

(52) U.S. Cl.
CPC ............ *A01N 57/20* (2013.01); *A01N 57/12* (2013.01); *A01N 57/14* (2013.01); *A01N 57/28* (2013.01); *A61K 9/0075* (2013.01); *A61K 9/02* (2013.01); *A61K 9/10* (2013.01); *A61K 9/2054* (2013.01); *A61K 9/4866* (2013.01); *A61K 31/661* (2013.01); *A61K 31/662* (2013.01); *A61K 31/664* (2013.01); *A61K 47/36* (2013.01); *A61N 5/0616* (2013.01)

(58) Field of Classification Search
CPC . A61K 8/00; A61K 8/02; A61K 8/022; A61K 8/0241; A61K 8/04; A61K 8/042; A61K 8/044; A61K 8/046; A61K 8/0291; A61K 8/06; A61K 8/062; A61K 8/064; A61K 8/066

See application file for complete search history.

(56) References Cited

U.S. PATENT DOCUMENTS

| | | | |
|---|---|---|---|
| 5,629,300 A | 5/1997 | Boberg et al. | |
| 5,952,372 A * | 9/1999 | McDaniel ............... | A61K 31/35 514/453 |
| 6,133,310 A | 10/2000 | Parks | |
| 6,258,378 B1 | 7/2001 | Schneider et al. | |
| 6,406,713 B1 | 6/2002 | Janoff et al. | |
| 6,680,308 B1 * | 1/2004 | Hassan ................... | A61K 31/66 514/125 |
| 7,919,522 B2 | 4/2011 | Soll et al. | |
| 8,440,240 B2 | 5/2013 | Gao et al. | |
| 8,475,818 B2 | 7/2013 | Guerino et al. | |
| 8,546,357 B2 | 10/2013 | Akama et al. | |
| 10,500,183 B2 * | 12/2019 | Spallitta ............... | A61K 9/2013 |
| 2003/0040504 A1 | 2/2003 | Gans et al. | |
| 2006/0084632 A1 | 4/2006 | Goyal et al. | |
| 2007/0020304 A1 * | 1/2007 | Tamarkin ............... | A01N 25/16 424/405 |
| 2007/0287733 A1 | 12/2007 | Snorrason | |
| 2008/0292560 A1 | 11/2008 | Tamarkin et al. | |

(Continued)

FOREIGN PATENT DOCUMENTS

| | | |
|---|---|---|
| EP | 2 355 790 A2 | 8/2011 |
| GB | 2419093 A * | 4/2006 |

(Continued)

OTHER PUBLICATIONS

Jarmuda et al, Potential role of *Demodex* mites and bacteria in the induction of rosacea; Journal of Medical Microbiology (2012), 61, 1504-1510 (Year: 2012).*
Agres (Sep. 29, 2011) "New Life for Old Drugs" Advantage Business Media. Accessible on the Internet at URL: http://www.dddmag.com/articles/2011/07/new-life-old-drugs.
Akilov (2004) "Immune response in demodicosis," J Eur Acad Dermatol Venereol. 18(4):440-4.
Akilov et al. (2003) "Association between human demodicosis and HLA class I," Clin Exp Dermatol. 28(1):70-3.
Akilov et al. (2005) "A clinico-pathological approach to the classification of human demodicosis," J Dtsch Dermatol Ges. 3(8):607-14.
Askin et al. (Feb. 25, 2010) "Comparison of the two techniques for measurement of the density of Demodex folliculorum: standardized skin surface biopsy and direct microscopic examination," Br J Dermatol. 162(5):1124-6.

(Continued)

*Primary Examiner* — Micah Paul Young
(74) *Attorney, Agent, or Firm* — Leydig, Voit & Mayer, Ltd.

(57) ABSTRACT

Embodiments of the invention involve treating skin afflictions by the topical or oral use of organophosphates. By effectively reducing or eliminating the population of *Demodex* mites in affected skin areas and areas where *Demodex* mites may exist, this treatment achieves a more complete remission of clinical signs and symptoms of the skin afflictions than any previously described method. Embodiments of the invention are useful for treating skin afflictions including common acne, seborrheic dermatitis, perioral dermatitis, an acneform rash, transient acantholytic dermatosis, acne necrotica milliaris, psoriasis, steroid induced dermatitis, primary irritation dermatitis, rosacea and for diagnositic methods thereof.

55 Claims, 3 Drawing Sheets

(56) References Cited

U.S. PATENT DOCUMENTS

| | | | |
|---|---|---|---|
| 2008/0299220 | A1 | 12/2008 | Tamarkin et al. |
| 2009/0099135 | A1 | 4/2009 | Enan |
| 2009/0214676 | A1* | 8/2009 | Gao .................. A61K 36/23 424/725 |
| 2010/0099668 | A1 | 4/2010 | Guerino et al. |
| 2011/0009457 | A1 | 1/2011 | Gorgens et al. |
| 2011/0033395 | A1 | 2/2011 | Kaoukhov et al. |
| 2011/0034471 | A1 | 2/2011 | Held |
| 2011/0059988 | A1 | 3/2011 | Heckeroth et al. |
| 2011/0288141 | A1 | 11/2011 | Freehauf et al. |
| 2013/0095051 | A1 | 4/2013 | Kaoukhov et al. |
| 2013/0131016 | A1 | 5/2013 | Akama et al. |
| 2013/0131017 | A1 | 5/2013 | Akama et al. |
| 2013/0225516 | A1 | 8/2013 | Soll et al. |
| 2013/0243886 | A1 | 9/2013 | Hu et al. |
| 2013/0338197 | A1 | 12/2013 | Mita et al. |
| 2014/0017216 | A1 | 1/2014 | Klein et al. |

FOREIGN PATENT DOCUMENTS

| | | | | |
|---|---|---|---|---|
| GB | 2419093 | A * | 4/2006 | ........... A61K 9/0014 |
| WO | WO 2004/000337 | A1 | 12/2003 | |
| WO | WO 2009/010754 | A2 | 1/2009 | |
| WO | WO 2009010754 | A2 * | 1/2009 | ............. A01N 53/00 |
| WO | WO 2009/030686 | A1 | 3/2009 | |
| WO | WO 2010/066639 | A2 | 6/2010 | |
| WO | WO 2013/078071 | A1 | 5/2013 | |

OTHER PUBLICATIONS

Assen et al. (2005) "Ivermectin: pharmacology and application in dermatology," International Journal of Dermatology. 44(12):981-988.

Aycan et al. (2007) "[Frequency of the appearance of *Demodex* sp. in various patient and age groups]," Turkiye Parazitoloji Dergisi. 31(2):115-8.—English summary only.

Ayres, Jr. (1963) "Rosaceam Like Demodicidosis," Calif Med. 98(6):328-330.

Baima et al. (2002) "Demodicidosis revisited," Acta Derm Venereol. 82(1):3-6.

Banker et al. (1979) "Disperse Systems," Ch. 9 In; Modern Pharmaceutics. Marcel Dekker, Inc. New York, New York.

Banker et al. (1979) "Tablet Dosage Forms," Ch. 10 In; Modern Pharmaceutics. Marcel Dekker, Inc. New York, New York.

Barnett (Aug. 29, 2012) "That Rose in Your Cheeks Could Be Bacteria," ABC News Medical Unit. Accessible on the Internet at URL: http://abcnews.go.com/blogs/health/2012/08/29/that-rose-in-your-cheeks-could-be-bacteria.

Basta-Juzbasić et al. (2002) "Demodex folliculorum in development of dermatitis rosaceiformis steroidica and rosacea-related diseases," Clin Dermatol. 20(2):135-40.

Beridge et al. (2009) "[Cryotherapy in treatment of skin demodecosis]," Georgian Med News. (170):43-5.—English abstract provided only.

Bhatia et al. (2006) "Dispelling the Mystery of Demodex," The Dermatologist. 15(1):38-41.

Bikowski et al. (2009) "Demodex Dermatitis a Retrospective Analysis of Clinical Diagnosis and Successful Treatment with Topical Crotamiton," J Clin Aesthet Dermatol. 2(1):20-5.

Bonnar et al. (1993) "The *Demodex* mite population in rosacea," J Am Acad Dermatol. 28(3):443-8.

Borgo et al. (20009) "PCR analysis for Wolbachia in human and canine *Demodex* mites," Arch Dermatol Res. 301(10):747-52.

Casas et al. (Dec. 2012) "Quantification of Demodex folliculorum by PCR in rosacea and its relationship to skin innate immune activation," Exp Dermatol. 21:906-910.

Castillo (Aug. 30, 2012) "Red skin condition rosacea may be due to bacteria in skin mites," CBS News. Accessible on the Internet at URL: http://www.cbsnews.com/8301-504763_162-57503771-10391704/red-skin-condition-rosacea-may-be-due-to-bacteria-in-skin-mites.

Crawford et al. (2004) "Rosacea: I. Etiology, pathogenesis, and subtype classification," J Am Acad Dermatol. 51(3):327-41.

Cresce et al. (Jun. 2014) "The Quality of Life Impact of Acne and Rosacea Compared to Other Major Medical Conditions," J Drugs Dermatol. 13(6):692-7.

Czepita et al. (2005) "[Investigations on the occurrence as well as the role of Demodex folliculorum and Demodex brevis in the pathogensis of blepharitis]," Klin Oczna. 107(1-3):80-2.—English abstract provided only.

Czepita et al. (2007) "Demoodex folliculorum and Demodex brevis as a cause of chronic marginal blepharitis," Ann Acad Med Stetin. 53(1):63-7.

Del Rosso et al. (Mar. 2013) "An Evaluation of the Potential Correlations Between Pathophysiologic Mechanisms, Clinical Manifestaions, and Managemant of Rosacea," Cutis. 91(3 Suppl):1-8.

Demmler (1997) "[Blepharitis. Demodex folliculorum, associated pathogen spectrum and specific therapy]," Ophthalmologe. 94(3):191-6.—English abstract only.

Dittrich (1966) "Synergistic Effect Between Vapors of C-8514/ Schering 36268 and Dichlorvos Against the Carmine Spider Mite," 59(4):893-896.—English abstract only.

Dolenc-Voljc et al. (2005) "Density of Demodex folliculorum in perioral dermatitis," Acta Derm Venereol. 85(3):211-5.

Efi Pasmatzi et al. (2009) "Rosacea-Like Demodicosis Induced by Topical Pimecrolimus: Immunohistochemical Evaluation of Inflammatory Infiltrate," Hospital Chronicles. 4(4):172-174.

Elston (Sep. 2010) "*Demodex mites*: Facts and controversies," Clin Dermatol. 28(5):502-504.

Erbagci et al. (1998) "The significance of Demodex folliculorum density in rosacea," Int J Dermatol. 37(6):421-5.

Fell (1886) "Demodex Folliculorum in Diseased Conditions of the Human Face," Proceedings of the Ninth Annual Meeting of the American Society of Microscopists. 8:120-127.

Forstinger et al. (1999) "Treatment of rosacea-like demodicidosis with oral ivermectin and topical permethrin cream," J Am Acad Dermatol. 41(5 Pt 1):775-7.

Forton (1998) "Demodex-associated folliculitis," Am J Dermatopathol. 20(5):536-7.

Forton (2007) "Standardized skin surface biopsy: method to estimate the Demodex folliculorum density, not to study the Demodex folliculorum prevalence," J Eur Acad Dermatol Venereol. 21(9):1301-2.

Forton (Oct. 24, 2011) "Papulopustular rosacea, skin immunity and Demodex: pityriasis folliculorum as a missing link," J Eur Acad Dermatol Venereol. 26(1):19-28.

Forton et al. (1993) "Density of Demodex folliculorum in rosacea: a case-control study using standardized skin-surface biopsy," Br J Dermatol 128:650-9.

Forton et al. (1998) "Demodex folliculorum and topical treatment: acaricidal action evaluated by standardized skin surface biopsy," Br J Dermatol. 138(3):461-6.

Forton et al. (1998) "Limitations of standardized skin surface biopsy in measurement of the density of Demodex folliculorum. A case report," Br J Dermatol. 139(4):697-700.

Forton et al. (2005) "Demodicosis and rosacea: epidemiology and significance in daily dermatologic practice," J Am Acad Dermatol. 52(1):74-87.

Fulk et al. (1996) "Pilocarpine gel for the treatment of demodicosis—a case series," Optom Vis Sci. 73(12):742-5.

Gao et al. (2005) "In vitro and in vivo killing of ocular Demodex by tea tree oil," Br J Ophthalmol. 89(11):1468-73.

Gao et al. (2007) "Clinical treatment of ocular demodecosis by lid scrub with tea tree oil," Cornea. 26(2):136-43.

Georgala et al. (2001) "Increased density of Demodex folliculorum and evidence of delayed hypersensitivity reaction in subjects with papulopustular rosacea," J Eur Acad Dermatol Venereol. Sep. 2001;15(5):441-4.

Gillette (Sep. 5, 2012) "Bacteria-laden mites may cause rosacea," Dermatology Times. Accessible on the Internet at URL: http://dermatologytimes.modernmedicine.com/dermatology-times/content/bacteria-laden-mites-may-cause-rosacea.

(56) References Cited

OTHER PUBLICATIONS

Goodman (Aug. 30, 2012) "Are Mites Causing Your Rosacea?," WebMD, LLC. Accessible on the Internet at URL: http://www.webmd.com/skin-problems-and-treatments/news/20120830/are-mites-causing-your-rosacea.
Hom et al. (Jun. 6, 2013) "Demodex," Optom Vis Sci. 90(7):e198-205.
Hsu et al. (2009) "Demodicosis: a clinicopathological study," J Am Acad Dermatol. 60(3):453-62.
International Search Report with Written Opinion corresponding to International Patent Application No. PCT/US2014/048420, dated Nov. 14, 2014.
Ivanhoe Newswire (Dec. 11, 2007) "Something to Blush About, Medical Breakthroughs," Ivanhoe Newswire.
Ivy (1995) "Demodicidosis in childhood acute lymphoblastic leukemia; an opportunistic infection occurring with immunosuppression," Journal of Pediatrics. 127(5):751-4.
Jansen et al. (2001) "Rosacea-like demodicidosis associated with acquired immunodeficiency syndrome," 144(1):139-42.
Jarmuda et al. (Nov. 2012) "Potential role of *Demodex* mites and bacteria in the induction of rosacea," Journal of Medical Microbiology. 61(11):1504-1510.
Jesitus (2007) "Empirical treatment is key to identifying rosacea, other dermatoses," Dermatology Times.
Jio (Aug. 31, 2012) "Health & Beauty: Could These Tiny Mites Be Causing Your Rosacea?" Conde Nast. Accessible on the Internet at URL: http://www.glamour.com/health-fitness/blogs/vitamin-g/2012/08/health-beauty-could-these-tiny.
Kennedy (2006) "CollaGenex wins FDA approval for Oracea," MarketWatch, Inc. Accessible on the Internet at URL: http://www.marketwatch.com/story/collagenex-wins-fda-approval-for-oracea.
Kheirkhah et al. (2007) "Corneal manifestations of ocular demodex infestation," Am J Ophthalmol. 143(5):743-749.
Kligman et al. (2011) "Demodex folliculorum: Requirements for Understanding Its Role in Human Skin Disease," Journal of Investigative Dermatology. 131:8-10.
Kulac et al. (2008) "Clinical importance of Demodex folliculorum in patients receiving phototherapy," Int J Dermatol. 47(1):72-7.
Kupiec-Banasikowska et al. (2007) "Rosacea," WebMD, LLC. Accessible on the Internet at URL: http://emedicine.medscape.com/article/1071429-overview.
Lacey et al. (2007) "Mite-related bacterial antigens stimulate inflammatory cells in rosacea," Br J Dermatol. 157(3):474-81.
Lacey et al. (2009) "Under the lash: *Demodex* mites in human diseases," Biochem (Lond). 31(4):2-6.—Author manuscript provided.
Lacey et al. (Feb. 16, 2013) "Demodex quantification methods: Limitations of Confocal Laser Scanning Microscopy (CLSM)," Br J Dermatol. 169(1):212-3.
Larios et al. (2008) "Rosacea-like demodicidosis," Lancet Infect Dis. 8(12):804.
Lazaridou et al. (2010) "The potential role of microorganisms in the development of rosacea," Journal of the German Society of Dermatology. 9:21-25.
Lee et al. (2007) "Granulomatous rosacea-like demodicidos," Dermatol Online J. 13(4):9.
Li et al. (Jan. 14, 2010) "Correlation between ocular Demodex infestation and serum immunoreactivity to Bacillus proteins in patients with Facial rosacea," Ophthalmology. 117(5):870-877.
Liu et al. (2010) "Pathogenic role of *Demodex* mites in blepharitis," Curr Opin Allergy Clin Immunol. 10(5):505-510.
MacKenzie (Aug. 30, 2012) "Rosacea may be caused by mite feces in your pores," New Scientist. Accessible on the Internet at URL: https://www.newscientist.com/article/dn22227-rosacea-may-be-caused-by-mite-faeces-in-your-pores/.
Manolette et al. (Nov. 5, 2015) "Demodicosis," WebMD, LLC. Accessible on the Internet at URL: http://emedicine.medscape.com/article/1203895-overview.
McCarty (Mar. 15, 2013) "Bayer Sues Glenmark Over Patent for Rosacea Drug Finacea," Bloomberg L. P. Accssible on the Internet at URL: http://www.bloomberg.com/news/articles/2013-03-15/bayer-sues-glenmark-over-patent-for-rosacea-drug-finacea.
Moore (Aug. 31, 2012) "Rosacea May Be Caused by Bacteria Released by Tiny Mites Living on the Skin," Medical News Today. Accessible on the Internet at URL: http://www.medicalnewstoday.com/releases/249664.php.
Moravvej et al. (2007) "Association of rosacea with demodicosis," Arch Iran Med. 10(2):199-203.
Mumcuoglu et al. (2005) "The role of HLA A2 and Cw2 in the pathogenesis of human demodicosis," Dermatology. 210(2):109-14.
National Rosacea Society (2010) "Mites and Eye Symptoms," NRS Web Blog Thursday. Accessible on the Internet at URL: http://www.rosacea.org/weblog/mites_and_eye_symptoms.
National Rosacea Society (2016) "All About Rosacea," National Rosacea Society Accessible on the Internet at URL: http://www.rosacea.org/patients/allaboutrosacea.php.
National Rosacea Society (Fall 2010) "NRS-Funded Studies Advance Knowledge of Rosacea's Causes," Rosacea Review. Accessible on the Internet at URL: http://www.rosacea.org/rr/2010/fall/article_1.php.
National Rosacea Society (May 3, 2004) "New Study Shows Role for Bacteria in Development of Rosacea Symptoms," NRS Press Release. Accessible on the Internet at URL: http://www.rosacea.org/press/archive/20040503.php.
National Rosacea Society (Sep. 5, 2012) "The Chicken, not the Egg?" National Rosacea Society. Accessible on the Internet at URL: http://www.rosacea.org/weblog/the_chicken_not_the_egg.
NBC News (Aug. 29, 2012) "Tiny mites on your face may cause rosacea," NBC News. Accessible on the Internet at URL: http://vitals.nbcnews.com/_news/2012/08/29/13554038-tiny-mites-on-your-face-may-cause-rosacea?lite.
New York Daily News (Sep. 5, 2012) "New discovery may hold clues to rosacea cure; Red bumps may be linked to mites living on the face," New York Daily News. Accessible on the Internet at URL: http://www.nydailynews.com/life-style/health/new-discovery-hold-clues-rosacea-cure-red-bumps-linked-mites-living-face-article-1.1152511.
Nielsen et al. (1988) "Glycolamide esters as biolabile prodrugs of carboxylic acid agents: synthesis, stability, bioconversion, and physicochemical properties," Journal of Pharmaceutical Sciences. 77:285-298.
NIH News (2007) "Lavender and Tea Tree Oils May Cause Breast Growth in Boys," NIH News. Accessible on the Internet at URL: http://www.nih.gov/news-events/news-releases/lavender-tea-tree-oils-may-cause-breast-growth-boys.
Norn (1970) "Demodex folliculorum. Incidence and possible pathogenic role in the human eyelid," Ch. VII In; Acta Ophthalmologica. 48(S108):71-78.
O'Connell (Jul. 14, 2009) "Study finds cause of rosacea," The Irish Times. Accessible on the Internet at URL: http://www.irishtimes.com/news/health/study-finds-cause-of-rosacea-1.699476.
O'Reilly et al. (Nov. 19, 2011) "Demodex-associated bacterial proteins induce neutrophil activation," Br J Dermatol. 166(4):753-60.
O'Reilly et al. (Apr. 24, 2012) "Demodex-associated Bacillus proteins induce an aberrant wound healing response in a corneal epithelial cell line (hTCEpi)," Invest Ophthalmol Vis Sci. 53(6):3250-9.
O'Reilly et al. (Jun. 18, 2012) "Positive correlation between serum immunoreactivity to Demodex-associated Bacillus proteins and erythematotelangiectatic rosacea," Br J Dermatol. 167(5):1032-6.
Pena et al. (2000) "Is demodex really non-pathogenic?" Rev Inst Med Trop Sao Paulo. 42(3):171-3.
Pitman (Aug. 30, 2012) "Researchers Claim to be Closer Towards Effective Treatment of Rosacea Cosmetics Design," William Reed Business Media SAS. Accessible on the Internet at URL: http://www.cosmeticsdesign.com/Formulation-Science/Researchers-claim-to-be-closer-towards-effective-treatment-of-rosacea.
Press Trust of India (Aug. 30, 2012) "Rosacea may be caused by skin bacteria: study," Business Standard. Accessible on the Internet at URL: http://www.business-standard.com/article/pti-stories/rosacea-may-be-caused-by-skin-bacteria-study-112083000384_1.html.

(56) References Cited

OTHER PUBLICATIONS

Prieto et al. (2002) "Effects of intense pulsed light on sun-damaged human skin, routine, and ultrastructural analysis," Lasers Surg Med. 30(2):82-5.
PSmicrographs "Follicle mite (*Demodex folliculorum*)," PSmicrographs. Accessible on the Internet at URL: www.psmicrographs.co.uk/follicle-mite--demodex-folliculorum-/science-image/80016342.
Rebora (2002) "The management of rosacea," Am J Clin Dermatol. 3(7):489-96.
Ríos-Yuil et al. (Mar. 2013) "Evaluation of Demodex folliculorum as a Risk Factor for the Diagnosis of Rosacea in Skin Biopsies. Mexico's General Hospital (1975-2010)," Indian J Dermatol. 58(2):157. pp. 1-10.
Roihu et al. (1998) "*Demodex mites* in acne rosacea," J Cutan Pathol. 25(10):550-2.
Román-Curto et al. (Aug. 2012) "Demodicidosis simulating acute graft-versus-host disease after allogeneic stem cell transplantation in one patient with acute lymphoblastic leukemia," Transpl Infect Dis. 14:387-390.
Rufli et al. (1981) "The hair follicle mites *Demodex folliculorum* and *Demodex brevis*: biology and medical importance. A review," Dermatologica. 162(1):1-11.
Sahn et al. (1992) "Demodicidosis in a child with leukemia," J Am Acad Dermatol. 27(5 Pt 2):799-801.
Sandoz "Sandoz Launches First Generic Version of Metrogel® 1% in the US," Sandoz: A Novartis. Accessible on the Internet at URL: http://www.sandoz.com/media_center/press_releases_news/global_news/sandoz_launches_first_generic_version_of_metrogel_reg_1_in_the_us.shtml.
Sattler et al. (Nov. 2012) "Non-invasive in vivo detection and quantification of *Demodex* mites by confocal laser scanning microscopy," Br J Dermatol. 167(5):1042-7.
Schaller et al. (2003) "Demodex abscesses: clinical and therapeutic challenges," J Am Acad Dermatol. 49(5 Suppl):S272-4.
Schmidt et al. (Oct. 2004) "Demodex and rosacea, III: Treatment of *Demodex* mites associated with inflammatory rosacea," Cosmetic Dermatology. 17(10):655-658.
Schneider et al. (1999) "Metrifonate: A Cholinesterase Inhibitor for Alzheimer's Disease Therapy," CNS Drug Reviews. 5(1):13-26.
Science Daily (Aug. 29, 2012) "Bacterial Cause Found for Skin Condition Rosacea," Science Daily. Accessible on the Internet at URL: https://www.sciencedaily.com/releases/2012/08/120829195121.htm.
Sekizawa et al. (1989) "Environmental Health Criteria 79: Dichlorvos," World Health Orgnization. Geneva, Switzerland.
Shelley et al. (1989) "Unilateral demodectic rosacea," J Am Acad Dermatol. 20(5 Pt 2):915-7.
Sifferlin (Sep. 4, 2012) "Rosacea: Caused by Mite Poop in Your Facial Pores?" Time Magazine. Accessible on the Internet at URL: http://healthland.time.com/2012/09/04/rosacea-caused-by-mite-poop-in-your-facial-pores/.
Spiegel et al. (1963) "Use of nonaqueous solvents in parenteral products," Journal of Pharmaceutical Sciences. 52(10):917-927.
Stanisław et al. (2012) "The potential role of *Demodex folliculorum* mites and bacteria in the induction of rosacea," Journal of Medical Microbiology. 61:1504-1510.

Supplementary European Search Report corresponding to European Patent Application No. 14832600, dated Jun. 29, 2016.
Talghini et al. (Jul. 1, 2014) "Demodex folliculorum and Skin Disease: A Case-Control Study," J. Med. Sci. 14(5):229-234.
Walton et al. (2000) "Studies in vitro on the relative efficacy of current acaricides for *Sarcoptes scabiei* var. *hominis*," Trans. Royal Chem. Soc. 94:92-96.
Wilkin et al. (2002) "Standard classification of rosacea: Report of the National Rosacea Society Expert Committee on the Classification and Staging of Rosacea" Journal of the American Academy of Dermatology. 46:584-587.
Wood (Archived web page from Dec. 12, 2010) "Compendium of Pesticide Common Names; Classification of acaricides," Web Archive of URL: http://alanwood.net/pesticides/class_acaricides.html. pp. 1-8.
Woods (2003) "It's Enough to Make Your Skin Crawl: Microscopic Mites May Be Linked to Acne, Thinning Hair and Other Skin Disorders," University of Florida's Institute of Food and Agricultural Sciences. Accessible on the Internet at URL: http://entomology.ifas.ufl.edu/pestalert/acne.htm.
Wozniacka et al. (2005) "Topical application of 1-methylnicotinamide in the treatment of rosacea: a pilot study," Clin Exp Dermatol. 30(6):632-5.
Zahavi et al. (1970) "Sensitivity of acetylcholinesterase in spider mites to organo-phosphorus compounds," Biochemical Pharmacology. 19:219-225.
Zhao et al. (2010) "Retrospective analysis of the association between demodex infestation and rosacea," Arch Dermatol. 146(8):896-902.
Zhao et al. (2011) "Facial dermatosis associated with Demodex: A case-control studu," Journal of Zhejiang University—Science B. 12(12):1008-1015.
Zhao et al. (2012) "A meta-analysis of association between acne vulgaris andinfestation," Journal of Zhejiang University—Science B. 13(3):192-202.
Zhao et al. (Aug. 2011) "Influence of temperature and medium on viability of Demodex folliculorum and Demodex brevis," Exp Appl Acarol. 54:421-425.
Aquilina et al. (2002) "Ivermectin-responsive Demodex infestation during human immunodeficiency virus infection. A case report and literature review," Dermatology (Basel) 205(4): 394-397.
Böni (2000) "Rosazea, Akne und weitere Erkran-kungen aus dem seborrhoischen Formenkreis" (English title: Rosacea, acne and other diseases of seborrhoic origin), Schweizerische Rundschau fur Medizin/Praxis 20000330 CH 89(14): 566-570, in German language (pp. 566-568 and 570 provided).
De Jaureguiberry et al. (1993) "Folliculite a Demodex: une cause de prurit au cours de l'infection par le virus de l'immunodeficienc humaine" (English title: Demodex folliculitis: A cause of pruritus during human immunodeficiency virus infection), Annales de Medicine Interne 144(1): 63-64, in French language.
European Office Action, dated Apr. 29, 2020, in counterpart EP Patent Application No. 14 832 600.2, 5 pp.
Jansen et al. (1996) "Demodex-Milben und ihre Bedeutung fur Gesichtsdermatosen" (English title: Demodex mites and their significance in facial dermatoses), Münchener Medizinische Wochenschrift 1996 DE 138(27): 483-487, in German language (p. 483 provided).

* cited by examiner

ORGANOPHOSPHATES FOR TREATING AFFLICTIONS OF THE SKIN

CROSS REFERENCE TO RELATED APPLICATION

This application claims the benefit of and priority to U.S. Provisional Patent App. Nos. 61/859,572, filed Jul. 29, 2013, 61/861,072, filed Aug. 1, 2013, 61/953,290, filed Mar. 14, 2014, each of which is hereby incorporated by reference to the extent not inconsistent herewith.

BACKGROUND

Provided herein are methods for treatment of various skin afflictions in humans employing topically applied or orally dosed organophosphates. By reducing or eliminating *Demodex* organisms from affected skin areas, this method reduces clinical signs of the skin afflictions which are primarily due to allergic and vasomotor responses of the body to the organism and bacteria that are carried by the organism.

Rosacea, originally termed acne rosacea, is a chronic inflammatory skin condition most commonly affecting the face and eyelids of middle-aged adults. Clinical signs include erythema (redness), dryness, papules, pustules, and nodules either singly or in combination in the involved skin areas. Eyelid involvement may be manifested by mild conjunctival irritation or inflammation of the meibomian (oil) glands on the eyelid margin. Chronic eyelid irritation can result in loss of eyelashes. No visual impairment accompanies the eyelid irritation. Chronic involvement of the nose with rosacea in men can cause a bulbous enlargement known as rhinophyma. In the classic situation, the condition develops in adults between the ages of 30 and 50. While certain lesions of rosacea may mimic lesions of acne *vulgaris*, the processes are separate and distinct, the principal differences being the presence of comedones (whiteheads and blackheads) only in acne *vulgaris* and not in rosacea, the characteristic midfacial localization and flushing of rosacea not seen in acne, and the potential for eyelid involvement in rosacea which never occurs in acne. In fact, the clinical observation has been made that persons who have classic acne *vulgaris* as teenagers rarely, if ever, develop full-blown rosacea as adults.

Rosacea develops in four stages over several years, in spasms aggravated by variations in various conditions such as temperature, alcohol, spices, exposure to sunlight and emotions. The various disease stages can be described in terms of the stages: Stage 1: stage of erythema episodes. The patients have erythrosis spasms due to the sudden dilation of the arterioles of the face, which then take on a congestive, red appearance. These spasms are caused by the emotions, meals and temperature changes; Stage 2: stage of couperosis, i.e., of permanent erythema with telangiectasia. Certain patients also have edema on the cheeks and the forehead; Stage 3: inflammatory stage with appearance of inflammatory papules and pustules, but without affecting the sebaceous follicles and thus with absence of cysts and comedones; and Stage 4: rhinophyma stage. This late phase essentially affects men. The patients have a bumpy, voluminous red nose with sebaceous hyperplasia and fibrous reordering of the connective tissue.

Conventionally, rosacea is treated orally or topically with antibiotics such as tetracyclines, erythromycin or clindamycin, but also with vitamin A, salicylic acid, antifungal agents, steroids, anti-infectious agents such as benzoyl peroxide, or with isotretinoin in severe cases or most commonly with metronidazole (an antibacterial agent).

Metronidazole is known for its antiparasitic, antiprotozoan and antibacterial properties. It is especially used for treating *Helicobacter pylori* infections. It is also prescribed in the treatment of rosacea, for its advantageous properties on the inflammatory lesions of rosacea, specifically on papules and pustules. Metronidazole exerts selective toxicity towards anaerobic microorganisms and also hypoxic cells. On the latter, metronidazole is reduced to various derivatives that are capable of changing the structure of their DNA.

U.S. Patent Application 2013/0095051 filed Dec. 6, 2012 describes a method of treating rosacea using avermectin/metronidazole in a topical application. U.S. Pat. No. 5,952,372 describes a method for treating rosacea using ivermectin orally or topically in order to reduce and eliminate the parasite *Demodex folliculorum* present on the skin of patients.

Ivermectin belongs to the avermectin family, a group of macrocyclic lactones produced by the bacterium *Streptomyces avermitilis*. The avermectins especially include ivermectin, invermectin, avermectin, abamectin, doramectin, eprinomectin and selamectin. Ivermectin is known for its antiparasitic and anthelmintic properties. The antiparasitic activity is thought to be due to the opening of a chlorine channel in the membrane of the neurons of the parasite under the effect of an increased release of the neuromediator GABA (gammaaminobutyric acid), inducing neuromuscular paralysis that may lead to the death of certain parasites. Ivermectin also interacts with other chlorine channels, especially those dependent on the neuromediator GABA (gammaaminobutyric acid).

Ivermectin is conventionally administered in the dermatological treatment of endoparasitic manifestations such as onchocerciasis and myiasis. U.S. Pat. No. 6,133,310 describes the use of ivermectin in the treatment of rosacea in order to reduce and eliminate the parasite *Demodex folliculorum* present on the skin of patients. U.S. Pat. No. 6,133,310 describes the use of ivermectin in the treatment of rosacea in order to reduce and eliminate the parasite *Demodex folliculorum* present on the skin of patients.

However, these treatments and compounds have drawbacks such as irritation and intolerance phenomena, especially when they are administered for a prolonged period. All current rosacea treatments seem only to be suppressive and not curative, acting especially on the pustulous spasms occurring during the inflammatory stage.

According to the National Rosacea Society an estimated 16 million Americans have rosacea, yet only a small fraction are being treated. Rosacea's etiology is currently under dispute in the dermatology community. Rosacea (roe-ZAY-she-uh) is a common skin condition that causes redness in your face and often produces small, red, pus-filled bumps. Left untreated, rosacea tends to worsen over time. Rosacea signs and symptoms may flare up for a period of weeks to months and then diminish before flaring up again. Rosacea can be mistaken for acne, an allergic reaction or other skin problems. While there's no cure for rosacea, current treatments can only help to control and reduce the signs and symptoms of the condition.

Rosacea is typically observed in individuals after the age of thirty as redness on the cheeks, nose, chin or forehead that may come and go. In some cases, rosacea may also occur on the neck, chest, scalp or ears. Over time the redness tends to become ruddier and more persistent, and visible blood vessels may appear. Left untreated, bumps and pimples often develop and in severe cases the nose may grow swollen and bumpy from excess tissue. This is the condition known as rhinophyma. In many rosacea patients the eyes are also affected, feeling irritated and appearing watery or bloodshot.

Although rosacea can affect all segments of the population, individuals with fair skin who tend to flush or blush easily are believed to be at greatest risk. The disease is more frequently diagnosed in women, but more severe symptoms tend to be seen in men. Rosacea can vary substantially from one individual to another and in most cases some rather than all of the potential signs and symptoms appear. According to a consensus committee and review panel of 17 medical experts worldwide, rosacea always includes at least one of the following primary signs, and various secondary signs and symptoms may also develop.

Primary Signs of rosacea include one or more of the following observable symptoms: (1) Flushing: Many people with rosacea have a history of frequent blushing or flushing. This facial redness may come and go, and is often the earliest sign of the disorder; (2) Persistent Redness Persistent facial redness is the most common individual sign of rosacea, and may resemble a blush or sunburn that does not go away; (3) Bumps and Pimples: Small red solid bumps or pus-filled pimples often develop. While these may resemble acne, blackheads are absent and burning or stinging may occur; (4) Visible Blood Vessels: In many people with rosacea, small blood vessels become visible on the skin.

Other Potential Signs and Symptoms include: (1) Eye Irritation. In many people with rosacea, the eyes may be irritated and appear watery or bloodshot, a condition known as ocular rosacea. The eyelids also may become red and swollen, and styes are common. Severe cases can result in corneal damage and vision loss without medical help. (2) Burning or Stinging. Burning or stinging sensations may often occur on the face. Itching or a feeling of tightness may also develop. (3) Dry Appearance. The central facial skin may be rough, and thus appear to be very dry. (4) Plaques. Raised red patches, known as plaques, may develop without changes in the surrounding skin. Skin (5) Thickening. The skin may thicken and enlarge from excess tissue, most commonly on the nose. This condition, known as rhinophyma, affects more men than women. (6) Swelling. Facial swelling, known as edema, may accompany other signs of rosacea or occur independently. (7) Signs Beyond the Face. Rosacea signs and symptoms may also develop beyond the face, most commonly on the neck, chest, scalp or ears.

Subtypes of rosacea: Subtype 1: (erythematotelangiectatic rosacea), characterized by flushing and persistent redness, and may also include visible blood vessels. Subtype 2: (papulopustular rosacea), characterized by persistent redness with transient bumps and pimples. Subtype 3: (phymatous rosacea), characterized by skin thickening, often resulting in an enlargement of the nose from excess tissue. Subtype 4: (ocular rosacea), characterized by ocular manifestations such as dry eye, tearing and burning, swollen eyelids, recurrent styes and potential vision loss from corneal damage.

Many patients experience characteristics of more than one subtype at the same time, and those often may develop in succession. While rosacea may or may not evolve from one subtype to another, each individual sign or symptom may progress from mild to moderate to severe. Early diagnosis and treatment are recommended.

As will be understood from the foregoing, methods of treating dermatological conditions, such as rosacea, are needed. Treatment methods are needed, for example, providing curative or long-term suppressive treatments capable of treating symptoms beyond the pustulous spasms which occur during the inflammation stage. Such treatment methods may be able to kill or inactivate the parasites or bacteria causing the allergic or vasomotor responses. Additionally, treatments exhibiting a combination enhanced efficacy and speed of treatment, low toxicity and reduced side effects would be useful and beneficial.

SUMMARY

Embodiments of the invention involve treatment of skin conditions by the topical and/or oral administration of organophosphate compounds. By effectively reducing or eliminating the population of *Demodex* mites in affected skin areas and areas where *Demodex* mites may exist, this treatment achieves a more complete remission of clinical signs and symptoms of the skin afflictions than conventional treatment approaches. In some embodiment, methods of the invention include treatment by administration of organophosphates so as to decrease the population of *Demodex* mites in afflicted regions of the skin and other regions of the skin not manifesting the conditions. Methods of the invention include treatment by repeated administration of organophosphates so as to maintain the population of *Demodex* mites in afflicted regions of the skin and other regions of the skin at levels low enough to prevent the skin affliction. Embodiments of the invention are useful for treating skin afflictions including common acne, seborrheic dermatitis, perioral dermatitis, an acneform rash, transient acantholytic dermatosis, acne necrotica milliaris, psoriasis, steroid induced dermatitis, primary irritation dermatitis, rosacea and any combination of these.

Aspects of the invention include therapeutic and prophylactic methods for treating, managing and/or preventing dermatological conditions, including rosacea, by administration of a therapeutic agent having an organophosphate active ingredient. In some embodiments, for example, the method comprises topically administering an organophosphate, such as dichlorvos or a prodrug thereof, to an individual afflicted with, or susceptible to, a dermatological condition such as rosacea, for example, by physically contacting regions of the skin and/or hair of the individual exhibiting symptoms of the dermatological condition with the organophosphate containing therapeutic agent and, optionally physically contacting regions of the skin and/or hair of the individual not manifesting symptoms with the organophosphate containing therapeutic agent. In an embodiment, for example, the organophosphate, such as diclorovos or a prodrug thereof, is topically administered to the individual by physically contacting at a dose and for an application period sufficient to significantly reduce the population of *demodex* mites on and in treated region(s) of the individual, for example, by reducing the *demodex* mite population on and in treated region(s) of the individual to a level equal to or less than 60%, optionally for some applications 90%, of the original population of *demodex* mites. In an embodiment, for example, therapeutic agent is administered via a delivery means providing effective surface coverage and/or subdermal penetration of the organophosphate active agent for a treatment period sufficient to significantly reduce the population of *demodex* mites on and in treated region(s) of the individual, for example, via topical administration via a body wash or shampoo, optionally applied to a significant portion (e.g., at least 50%) or substantially all (e.g., at least 90%) of the skin and hair of the individual.

The invention includes therapeutic and prophylactic methods including administering a therapeutic agent having an organophosphate active ingredient to an individual via a dosing regimen effective for controlling the population of *demodex* mites, such as *Demodex brevis* mites and/or *Demodex folliculorum* mites, in treated regions of the skin and/or hair, for example, so as to be low enough to prevent, or ameliorate symptoms associated with, a dermatological condition, such as rosacea. Dosing regimens useful for the present methods include selection of one or more of the following: (1) the amount of organophosphate containing therapeutic agent administered to the individual, (2) the application period (e.g., contact time) in which the organophosphate containing therapeutic agent is provided in contact with the skin and/or hair of the individual, (3) the extent of the individual topically contacted with the organophosphate containing therapeutic agent (e.g., afflicted regions exhibiting symptoms of the condition and/or nonafflicted regions no exhibiting symptoms of the condition), (4) the frequency and duration of repeated administration of organophosphate containing therapeutic agent administered to the individual, and (5) administration of organophosphate containing therapeutic agent to the environment of the individual and any combination of these. The dosing regimens of the present invention are effective at reducing, and optionally maintaining, the population of *demodex* mites on and in the individual at a level sufficient to prevent, manage or ameliorate the dermatological condition, for example, so as to reduce or eliminate symptoms of the dermatological condition.

In an aspect, the invention provides a method of treating a skin affliction comprising a step of orally administering or topically applying to an individual having the skin affliction an organophosphate in a dosage sufficient to inactivate *Demodex brevis* mites, *Demodex folliculorum* mites or both from hair follicles or skin of said individual, resulting in attenuation, amelioration and/or cessation of clinical symptoms associated with the skin affliction and caused, directly or indirectly, by the mites. In an aspect, a manifestation of the skin affliction may be an allergic and/or vasomotor responses to the mites that cause the skin affliction or symptoms thereof. In an embodiment, for example, afflicted regions and/or non-afflicted regions of the skin and/or hair follicles of the individual are physically contacted with the organophosphate, optionally in an amount to at least partially, or optionally entirely, fill pores in the skin and/or hair follicles of the treat.

In an embodiment, for example, said organophosphate is provided at said dosage sufficient to kill said *Demodex brevis* mites, *Demodex folliculorum* mites or both from hair follicles and/or skin of the individual contacted with said organophosphate. In an embodiment, for example, said organophosphate is provided to said individual at said dosage is sufficient to provide a reduction in the population of said *Demodex brevis* mites, *Demodex folliculorum* mites or both from said hair follicles or skin contacted with said organophosphate greater than or equal to 80%. In an embodiment, for example, said dosage of the organophosphate is sufficient to provide for said reduction in the population of said *Demodex brevis* mites, *Demodex folliculorum* mites or both over a time interval less than or equal to 1 month. In an embodiment, for example, the method further comprises re-applying or re-administering said organophosphate in a dosage sufficient to maintain said reduction in said population of said *Demodex brevis* mites, *Demodex folliculorum* mites or both over a time interval of between about 10 to 120 days, or greater than or equal to two months. In an aspect, the re-applying or re-administering is timed to a life cycle property of the mites being controlled. For example, the time period may be greater than a time for an egg to hatch but less than the time for an adult mite to provide a fertilized egg. In an aspect, the time between consecutive administrations may be between 3 and 10 days or may be between 3 and 7 days. In an aspect, the time between consecutive administrations is selected so that administration is about bi-weekly or is bi-weekly. In an embodiment, for example, said organophosphate is provide at said dosage sufficient to render said *Demodex brevis* mites, *Demodex folliculorum* mites or both incapable of reproducing on or in hair follicles and/or skin of the individual contacted with said organophosphate. In an embodiment, for example, said organophosphate is provided at said dosage sufficient to at least partially, and optionally completely, fill pores of said skin, hair follicles or both of the individual contacted with said organophosphate. In an aspect, the incapable of reproducing may reflect killing of adult mites. In an aspect, the incapable of reproducing may reflect killing of pre-adult mites, such as larvae. In an aspect, the incapable of reproducing may reflect making the eggs non-viable, so that larvae does not emerge from eggs or any emergent from the eggs cannot grow into a mite capable of reproducing.

The present methods are versatile and useful for treatment of a range of dermatological conditions, for example, skin conditions affecting the facial skin, eyelids or both. In an embodiment, for example, the skin affliction is one or more of common acne, seborrheic dermatitis, perioral dermatitis, an acneform rash, transient acantholytic dermatosis, acne necrotica milliaris, psoriasis, steroid induced dermatitis, primary irritation dermatitis or rosacea. In an embodiment, for example, the skin condition is rosacea. In an embodiment, for example, the skin affliction is erythematotelangiectatic rosacea, papulopustular rosacea, phymatous rosacea, ocular rosacea or rhinophyma.

A range of active ingredients are useful in the present methods, particularly those active agents exhibiting a combination of useful skin penetration, efficacy for inactivating *demodex* mites, and low toxicity. In an embodiment, for example, said organophosphate is a miticide or insecticide. In an embodiment, for example, said organophosphate kills *Demodex brevis* mites, *Demodex folliculorum* mites or both. In an embodiment, for example, said organophosphate kills larva or eggs of said *demodex brevis* mites, *Demodex folliculorum* mites or both.

Certain methods of the invention further comprise administration of the organophosphate to the individual in a manner providing delivery to tissue within and/or beneath the outer layer of the skin, such as delivery into the pores of the skin and/or to regions beneath the epidermis. In an embodiment, for example, said organophosphate is transported into an epidermis or a subdermal region upon contact with said hair follicles and/or skin of the individual, optionally exhibiting a transport rate into said epidermis or a subdermal region upon contact with said hair follicles and/or skin of the individual to provide organophosphate contact with the mite in a time interval that is less than or equal to 1 minute. In an embodiment, for example, the organophosphate is characterized by a biological half-life less than or equal to 30 minutes. Certain formulations of the topical organophosphates useful with the methods of the invention optionally comprise one or more compositions that increase a permeability of the skin, such as dimethyl sulfoxide (DMSO).

In an embodiment, for example, the organophosphate comprises one or more organophosphates selected from the group consisting of acephate, azamethiphos, azinphos ethyl, azinphos methyl, bromophos, bromophos ethyl, cadusofos, carbophenythion, chlormephos, chlorphoxim, chlorpyrifos, chlorpyrifos-methyl, chlorthiophos, chlorvinophos, croumaphos, crotoxyphos, crufomate, cyanofenphos, cyanophos, demephron-O, demephron-S, demeton-O, demeton-S, demeton-S-methyl, demeton-S-methylsulphon, dialifos, diazinon, dichlofenthion, dichlorvos, dicrotophos, dimefphox, dimethoate, dioxabenzophos, dioxathion, disulfoton, ditalmifos, edifenphos, EPBP, EPN, ESP, ethion, ethopropos, etrimfos, famphur, fenamiphos, fenchlorphos, fenitrothion, fensulfothion, fenthion, fenofos, formothion, fosmethilan, heptenophos, isazofos, isofenphos, isothioate, isoxathion, jodfenphos, leptophos, metrifonate, malathion, menazon, mephosfolan, methacrifos, methamidophos, methidathion, mevinphos, monocrotophos, naled, omethoate, oxydemeton-methyl, parathion, parathion-methyl, phenthoate, phorate, phosalone, phosmet, phosphamidon, phosphamidon amide, phospholan, phoxim, pirimiphos-ethyl, pirimiphos-methyl, profenofos, propaphos, propetamphos, prothiofos, prothoate, pyraclofos, pyridaphenthion, quinlphos, schradan, sulfotep, sulprofos, temephos, TEPP, terbufos, tetrachlorvinphos, thiometon, thionazin, triazophos, trichlorfon, vamidothion, a prodrug of these and a pharmaceutically acceptable salt or ester of these. In an embodiment, for example, the organophosphate is dichlorvos or a prodrug or pharmaceutically acceptable salt or ester thereof. In an embodiment, for example, the organophosphate is metrifonate or a prodrug or pharmaceutically acceptable salt or ester thereof.

Organophosphate active agents of the invention may be provided in a variety of forms useful for formulation, administration and delivery. In an embodiment, the organophosphate active ingredient is administered topically to the individual in need. In an embodiment, for example, the organophosphate topically applied as formulated in a carrier lotion, cream, soap, wash, shampoo or gel. In an embodiment, for example, the organophosphate has a concentration in the topically applied lotion, cream, soap, wash, shampoo or gel selected from the range 0.001 to 5 percent by weight, optionally for some applications selected from the range 0.001 to 5 percent by weight 0.01 to 1 percent by weight, 0.5% to 2% by weight, or about 1% by weight. In an embodiment, for example, the organophosphate in the topically applied lotion, cream, soap, wash, shampoo or gel is provided in a lowest concentration effective for killing the *demodex brevis* mites, *Demodex folliculorum* mites or both. In an embodiment, for example, a method of the invention further comprises providing a dosage of said organophosphate in the topically applied lotion, cream, soap, wash, shampoo or gel less than 150 mg/kg of body mass. In an embodiment, for example, a method of the invention further comprises providing a dosage of said organophosphate in the topically applied lotion, cream, soap, wash, shampoo or gel selected from the range of 0.01 mg per kg of body mass to 50 mg/kg of body mass, or about 0.1 mg/kg of body mass to 1.5 mg/kg of body mass, or about 0.6 mg/kg of body mass, including for an organophosphate that is dichlorvos.

In an embodiment, the therapeutic agent containing the organophosphate active ingredient is topically administered to the individual during an administration period sufficient to provide high coverage (e.g., 80% or greater) of the treated regions of the skin and hair and/or subdermal penetration of the organophosphate active ingredient to a least a portion of and optionally substantially all (e.g., 80% or greater) of the treated regions of the skin. In an embodiment, the therapeutic agent containing the organophosphate active ingredient is topically administered to the individual for an administration period selected from the range of 1 second to 10 minutes, and optionally for some embodiments 5 seconds to 5 minutes and optionally for some embodiments 10 seconds to 1 minute. In an embodiment, said dosage of organophosphate in the topically applied lotion, cream, soap, wash, shampoo or gel is a lowest dose effective for killing the *demodex* mites, for example, to an extent useful for preventing or ameliorating the affliction. In an embodiment, for example, the topically applied organophosphate is encapsulated, for example, in a vesicles, microliposomes or micelles. In an embodiment, for example, the topically applied organophosphate is provided as an emulsion, optionally a nanoemulsion, in said topically applied lotion, cream, soap, wash, shampoo or gel.

Methods of the invention include repeated treatment of the skin and/or hair follicles of the individual, for example, to systematically reduce and/or maintain the population of the *demodex* mites at a level resulting in prevention, elimination or amelioration of the affliction or symptoms thereof. In an embodiment, for example, a method of the invention further comprises topically applying said organophosphate to skin areas affected by the skin affliction. In an embodiment, for example, a method of the invention further comprises topically applying said organophosphate to skin areas not affected by the skin affliction. In an embodiment, for example, a method of the invention further comprises topically applying said organophosphate to skin and hair areas of the body where *Demodex brevis* mite or *Demodex folliculorum* mites are present. In an embodiment, for example, a method of the invention further comprises topically applying said organophosphate to all skin areas of said individual. In an embodiment, for example, a method of the invention further comprises topically applying said organophosphate to all hair areas of said individual.

Treatment methods of the invention may also include additional steps to avoid or reduce the extent of repopulation of *demodex* mites on the individual undergoing treatment. In an embodiment, for example, a method of the invention further comprises a step of applying the organophosphate to the individual's clothing, linens or both clothing and linens. In an embodiment, a method of the invention further comprises a step of orally administering or topically applying the organophosphate to others having contact with the individual in a dosage sufficient to inactivate *Demodex brevis* mites, *Demodex folliculorum* mites or both from hair follicles or skin of the others, for example, wherein such others include household members, children, spouses, partners, family members or pets.

In an embodiment, for example, the topically applied organophosphate is applied to the hair follicles and skin of the individual. In an aspect, for example, the topically applied organophosphate penetrates an outer layer of the skin of the individual, thereby exposing the *Demodex brevis* mites, *Demodex folliculorum* mites or both present below the outer layer of the skin to the organophosphate, for example, to a depth below the outer layer of the skin selected over the range of 1 µm to 3 mm. In an embodiment, for example, the topically applied organophosphate penetrates to a subdermal region of the skin of the individual, such as the dermis or subcutis regions, thereby exposing the *Demodex brevis* mites, *Demodex folliculorum* mites or both present in the subdermal region of the skin to the organophosphate.

Methods of the invention include dosing and re-administration regimens effective for reducing and maintaining the population of *demodex* mites to provide prevention, elimination or amelioration of the skin conditions or symptoms thereof. In an embodiment, for example, the organophosphate is orally administered or topically applied in a continued intermittent regime sufficient for prophylactic control of *demodex* mite population in the hair follicles and/or skin of the individual.

In an embodiment, for example, the topically applied organophosphate is applied to affected skin areas at least once and not more than twice daily for a period of two to six weeks. In an embodiment, for example, the topically applied organophosphate is applied to the affected skin areas and/or to non-affected skin areas during a first application period, thereby inactivating said *Demodex brevis* mites, *Demodex folliculorum* mites or both from the hair follicles in the skin of the individual. In an embodiment, for example, the topically applied organophosphate is further applied to the affected skin areas and/or to non-affected skin areas during a second application period, thereby inactivating said *Demodex brevis* mites, *Demodex folliculorum* mites or both from the hair follicles and/or skin of the individual that have matured from a larval form and/or an egg form present on and/or in the skin during or after the first application period. In an embodiment, for example, the topically applied organophosphate is further applied to the affected skin areas and/or to non-affected skin areas during a third application period, thereby inactivating said *Demodex brevis* mites, *demodex folliculorum* mites or both from the hair follicles and or skin of the individual *demodex brevis* and/or *Demodex folliculorum* mites that have matured from a larval form and/or an egg form present on and/or in the skin and/or the hair follicles during or after the first application period and/or the second application period.

In an embodiment, for example, the first application period and the second application period are separated by at least five days and not more than ten days, and optionally for some embodiments, the first application period and the second application period are separated by at least seven days. In an embodiment, for example, the first application period and the second application period are separated by a time sufficient to allow larva of said *Demodex brevis* mites, *Demodex folliculorum* mites or both to mature into an adult form and/or to allow eggs of said *Demodex brevis* mites, *demodex folliculorum* mites or both to mature into the adult form. In an embodiment, for example, the second application period and the third application period are separated by at least five days and not more than ten days, and optionally for some embodiments, the second application period and the third application period are separated by at least seven days. In an embodiment, for example, the second application period and the third application period are separated by a time sufficient to allow time sufficient to allow larva of said *Demodex brevis* mites, *Demodex folliculorum* mites or both to mature into an adult form and/or to allow eggs of said *Demodex brevis* mites, *Demodex folliculorum* mites or both to mature into the adult form.

In an aspect, the organophosphate active ingredient is administered orally to the individual in need. In an embodiment, for example, the orally administered organophosphate is administered as an oral dose equal to or less than 150 mg per kg of body mass. In an embodiment, for example, the orally administered organophosphate is administered as an oral dose selected from the range of 0.01 mg per kg of body mass and 50 mg per kg of body mass. In an embodiment, for example, the orally administered organophosphate is administered as an oral dose of a lowest dose effective for killing the *demodex* mites. In an embodiment, for example, the orally administered organophosphate is administered as a daily dose of 1 to 20 mg per kg of body mass, optionally 10 mg per kg of body mass. In an embodiment, for example, the orally administered organophosphate is administered as a daily dose 1 to 10 mg per kg of body mass, optionally of 7.5 mg per kg of body mass. In an embodiment, for example, the orally administered organophosphate is administered as a three times per day dose of 1 to 10 mg per kg of body mass, optionally 5 mg per kg of body mass. In an embodiment, for example, the orally administered organophosphate is repeated two to four times with spacing of three to seven days between them. In an embodiment, for example, the orally administered organophosphate is formulated as a prodrug or pharmaceutically acceptable salt or ester.

In an aspect, methods of the invention are useful for eliminating the presence and/or reducing population of bacteria originating from *demodex* mites on the skin and/or hair follicles of the individual, such as eliminating or reducing bacteria that result in allergic and/or vasomotor responses that cause the skin affliction in the individual and symptoms thereof. In an embodiment, for example, the inactivation of the *demodex brevis* and/or *Demodex folliculorum* mites from hair follicles and/or skin of the individual results in a reduction in population of one or more bacteria in the hair follicles and/or skin of the individual. In an embodiment, for example, the allergic and/or vasomotor responses to the mites result from a presence of one or more bacteria associated with the mites in the hair follicles and/or skin of the individual. In an embodiment, for example, the one or more bacteria comprise one or more bacteria from the genus *staphylococcus* or from the genus *bacillus*. In an embodiment, for example, the one or more bacteria comprise *Bacillus oleronius* bacteria. In an embodiment, for example, the one or more bacteria comprise *Staphylococcus epidermidis* bacteria. In an embodiment, for example, the one or more bacteria are present in a digestive system of the *Demodex brevis* and/or *Demodex folliculorum* mites.

In an aspect, the invention provides a method of treating a skin affliction comprising a step of topically applying an active ingredient in a dosage to an individual having the skin affliction to inactivate *Demodex brevis* mites, *Demodex folliculorum* mites or both from hair follicles or skin of said individual, resulting in cessation of the manifestations of allergic and/or vasomotor responses to the mites that cause symptoms and signs of the skin affliction in the individual resulting in amelioration or cessation of the manifestations of allergic and/or vasomotor responses to the mites that cause the skin affliction or symptoms thereof, wherein the topically applied active ingredient is applied to skin areas affected by the skin affliction and to skin areas not affected by the skin affliction. In an embodiment, for example, afflicted regions and/or non-afflicted regions of the skin and/or hair follicles of the individual are physically contacted with the active ingredient, optionally in an amount to at least partially fills pores in the skin and/or hair follicles.

In this manner, the treatment may correspond more to a whole-body treatmetn wherein the active ingredient is formulated in a shampoo or body-wash that can be applied to a large portion of the individuals skin in a rapid and effective manner. In an embodiment, the shampoo or body-wash is applied to at least 50% of the total surface area of skin of the individual, and may, therefore, include both skin areas exhibiting a symptom and other skin areas that are do not indicate a symptom. In an aspect, the total surface area is selected from a range that is greater than 50% and up to 100% of the total skin surface area.

In an embodiment, for example, the topically applied active ingredient is applied to all skin of the individual to inactivate *Demodex brevis* mites, *Demodex folliculorum* mites or both from all skin of the individual. In an embodiment, for example, the active ingredient comprises an organophosphate or an avermectin. In an embodiment, for example, active ingredient comprises dichlorvos or a prodrug or pharmaceutically acceptable salt or ester thereof. In an embodiment, for example, the active ingredient comprises one or more organophosphates selected from the group consisting of acephate, azamethiphos, azinphos ethyl, azinphos methyl, bromophos, bromophos ethyl, cadusofos, carbophenythion, chlormephos, chlorphoxim, chlorpyrifos, chlorpyrifos-methyl, chlorthiophos, chlorvinophos, croumaphos, crotoxyphos, crufomate, cyanofenphos, cyanophos, demephron-O, demephron-S, demeton-O, demeton-S, demeton-S-methyl, demeton-S-methylsulphon, dialifos, diazinon, dichlofenthion, dichlorvos, dicrotophos, dimefphox, dimethoate, dioxabenzophos, dioxathion, disulfoton, ditalmifos, edifenphos, EPBP, EPN, ESP, ethion, ethopropos, etrimfos, famphur, fenamiphos, fenchlorphos, fenitrothion, fensulfothion, fenthion, fenofos, formothion, fosmethilan, heptenophos, isazofos, isofenphos, isothioate, isoxathion, jodfenphos, leptophos, malathion, menazon, mephosfolan, methacrifos, methamidophos, methidathion, mevinphos, monocrotophos, naled, omethoate, oxydemeton-methyl, parathion, parathion-methyl, phenthoate, phorate, phosalone, phosmet, phosphamidon, phosphamidon amide, phospholan, phoxim, pirimiphos-ethyl, pirimiphos-methyl, profenofos, propaphos, propetamphos, prothiofos, prothoate, pyraclofos, pyridaphenthion, quinlphos, schradan, sulfotep, sulprofos, temephos, TEPP, terbufos, tetrachlorvinphos, thiometon, thionazin, triazophos, trichlorfon, vamidothion, any prodrug of these and any pharmaceutically acceptable salt or ester of these. In an embodiment, for example, the active ingredient comprises ivermectin, selamectin, doramectin, abamectin or prodrugs or pharmaceutically acceptable salts or esters thereof. In an embodiment, for example, the active ingredient comprises a miticide or insecticide. In an embodiment, for example, the organophosphate kills *Demodex brevis* mites, *Demodex folliculorum* mites or both. In an embodiment, for example, the organophosphate kills larva or eggs of said *Demodex brevis* mites, *demodex folliculorum* mites or both. In an embodiment, for example, the skin affliction comprises one or more of common acne, seborrheic dermatitis, perioral dermatitis, an acneform rash, transient acantholytic dermatosis, acne necrotica milliaris, psoriasis, steroid induced dermatitis, primary irritation dermatitis or rosacea.

Statements Regarding Chemical Compounds and Nomenclature

In an embodiment, a composition or compound used with the methods of the invention is isolated or purified. In an embodiment, an isolated or purified compound is at least partially isolated or purified as would be understood in the art. In an embodiment, the composition or compound of the invention has a chemical purity of 95%, optionally for some applications 99%, optionally for some applications 99.9%, optionally for some applications 99.99%, and optionally for some applications 99.999% pure.

Many of the compounds used in the methods of the invention contain one or more ionizable groups. Ionizable groups include groups from which a proton can be removed (e.g., —COOH) or added (e.g., amines) and groups which can be quaternized (e.g., amines). All possible ionic forms of such molecules and salts thereof are intended to be included individually in the disclosure herein. With regard to salts of the compounds herein, one of ordinary skill in the art can select from among a wide variety of available counterions that are appropriate for preparation of salts of this invention for a given application. In specific applications, the selection of a given anion or cation for preparation of a salt can result in increased or decreased solubility of that salt.

The term "organophosphate" refers generally to compounds having at least one organophosphate group, or a prodrug thereof. In some embodiments, for example, the organophosphate is an ester of phosphoric acid ($H_3PO_4$). In some embodiments, for example, the organophosphate is a halogenated ester of phosphoric acid ($H_3PO_4$), such as a chlorinated or brominated ester of phosphoric acid ($H_3PO_4$). In some embodiments, for example, the organophosphate is represented by the structure $PO_4R'R''R'''$, where each of R', R" and R''' is independently hydrogen or an organic group or substituted organic group, and wherein at least one of R', R" and R''' is not hydrogen. In an embodiment, for example, each of R', R" and R''' are independently hydrogen or a substituted or nonsubstituted alkyl group, alkenyl group, aryl group, heteroaryl group, arylalkyl group, acyl group, alkynyl group, alkoxycarbonyl, halo group, amino group or any combination of these. In an embodiment, for example, at least one of R', R" and R''' is a dichlorovinyl group, such as a group having the formula $CCl_2$=CH—, and optionally the other(s) of R', R" and R''' are independently hydrogen or a $C_1$-$C_5$ alkyl group, and optionally for some application a methyl group. In an embodiment, the organophosphate is 2,2-dichlorovinyl dimethyl phosphate, or a derivative or prodrug thereof. In an embodiment, the organophosphate is isolated or purified, for example, prior to formulation and/or administration.

Organophosphates useful in the methods and compositions of the invention include, but are not limited to acephate, azamethiphos, azinphos ethyl, azinphos methyl, bromophos, bromophos ethyl, cadusofos, carbophenythion, chlormephos, chlorphoxim, chlorpyrifos, chlorpyrifos-methyl, chlorthiophos, chlorvinophos, croumaphos, crotoxyphos, crufomate, cyanofenphos, cyanophos, demephron-O, demephron-S, demeton-O, demeton-S, demeton-S-methyl, demeton-S-methylsulphon, dialifos, diazinon, dichlofenthion, dichlorvos, dicrotophos, dimefphox, dimethoate, dioxabenzophos, dioxathion, disulfoton, ditalmifos, edifenphos, EPBP, EPN, ESP, ethion, ethopropos, etrimfos, famphur, fenamiphos, fenchlorphos, fenitrothion, fensulfothion, fenthion, fenofos, formothion, fosmethilan, heptenophos, isazofos, isofenphos, isothioate, isoxathion, jodfenphos, leptophos, malathion, menazon, mephosfolan, methacrifos, methamidophos, methidathion, mevinphos, monocrotophos, naled, omethoate, oxydemeton-methyl, parathion, parathion-methyl, phenthoate, phorate, phosalone, phosmet, phosphamidon, phosphamidon amide, phospholan, phoxim, pirimiphos-ethyl, pirimiphos-methyl, profenofos, propaphos, propetamphos, prothiofos, prothoate, pyraclofos, pyridaphenthion, quinlphos, schradan, sulfotep, sulprofos, temephos, TEPP, terbufos, tetrachlorvinphos, thiometon, thionazin, triazophos, trichlorfon, vamidothion, any prodrug of these, any pharmaceutically acceptable salt or ester of these and any combination thereof.

As used herein, the term "group" may refer to a functional group of a chemical compound. Groups of the present compounds refer to an atom or a collection of atoms that are a part of the compound. Groups of the present invention may be attached to other atoms of the compound via one or more covalent bonds. Groups may also be characterized with respect to their valence state. The present invention includes groups characterized as monovalent, divalent, trivalent, etc. valence states.

As used herein, the term "substituted" refers to a compound wherein a hydrogen is replaced by another functional group.

As used herein, the term "halo" refers to a halogen group such as a fluoro (—F), chloro (—Cl), bromo (—Br), iodo (—I) or astato (—At).

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. The term cycloalkyl specifically refers to an alky group having a ring structure such as ring structure comprising 3-30 carbon atoms, optionally 3-20 carbon atoms and optionally 2-10 carbon atoms, including an alkyl group having one or more rings. Cycloalkyl groups include those having a 3-, 4-, 5-, 6-, 7-, 8-, 9- or 10-member carbon ring(s) and particularly those having a 3-, 4-, 5-, 6-, or 7-member ring(s). The carbon rings in cycloalkyl groups can also carry alkyl groups. Cycloalkyl groups can include bicyclic and tricycloalkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxy group is an alkyl group that has been modified by linkage to oxygen and can be represented by the formula R—O and can also be referred to as an alkyl ether group. Examples of alkoxy groups include, but are not limited to, methoxy, ethoxy, propoxy, butoxy and heptoxy. Alkoxy groups include substituted alkoxy groups wherein the alky portion of the groups is substituted as provided herein in connection with the description of alkyl groups. As used herein MeO— refers to $CH_3O$—.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cycloalkenyl groups include those in which a double bond is in the ring or in an alkenyl group attached to a ring. The term cycloalkenyl specifically refers to an alkenyl group having a ring structure, including an alkenyl group having a 3-, 4-, 5-, 6-, 7-, 8-, 9- or 10-member carbon ring(s) and particularly those having a 3-, 4-, 5-, 6- or 7-member ring(s). The carbon rings in cycloalkenylgroups can also carry alkyl groups. Cycloalkenylgroups can include bicyclic and tricyclic alkenyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogen atoms replaced with one or more fluorine atoms.

Aryl groups include groups having one or more 5-, 6- or 7-member aromatic rings, including heterocyclic aromatic rings. The term heteroaryl specifically refers to aryl groups having at least one 5-, 6- or 7-member heterocyclic aromatic rings. Aryl groups can contain one or more fused aromatic rings, including one or more fused heteroaromatic rings, and/or a combination of one or more aromatic rings and one or more nonaromatic rings that may be fused or linked via covalent bonds. Heterocyclic aromatic rings can include one or more N, O, or S atoms in the ring. Heterocyclic aromatic rings can include those with one, two or three N atoms, those with one or two O atoms, and those with one or two S atoms, or combinations of one or two or three N, O or S atoms. Aryl groups are optionally substituted. Substituted aryl groups include among others those which are substituted with alkyl or alkenyl groups, which groups in turn can be optionally substituted. Specific aryl groups include phenyl, biphenyl groups, pyrrolidinyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms. Aryl groups include, but are not limited to, aromatic group-containing or heterocylic aromatic group-containing groups corresponding to any one of the following: benzene, naphthalene, naphthoquinone, diphenylmethane, fluorene, anthracene, anthraquinone, phenanthrene, tetracene, tetracenedione, pyridine, quinoline, isoquinoline, indoles, isoindole, pyrrole, imidazole, oxazole, thiazole, pyrazole, pyrazine, pyrimidine, purine, benzimidazole, furans, benzofuran, dibenzofuran, carbazole, acridine, acridone, phenanthridine, thiophene, benzothiophene, dibenzothiophene, xanthene, xanthone, flavone, coumarin, azulene or anthracycline. As used herein, a group corresponding to the groups listed above expressly includes an aromatic or heterocyclic aromatic group, including monovalent, divalent and polyvalent groups, of the aromatic and heterocyclic aromatic groups listed herein are provided in a covalently bonded configuration in the compounds of the invention at any suitable point of attachment. In embodiments, aryl groups contain between 5 and 30 carbon atoms. In embodiments, aryl groups contain one aromatic or heteroaromatic six-membered ring and one or more additional five- or six-membered aromatic or heteroaromatic ring. In embodiments, aryl groups contain between five and eighteen carbon atoms in the rings. Aryl groups optionally have one or more aromatic rings or heterocyclic aromatic rings having one or more electron donating groups, electron withdrawing groups and/or targeting ligands provided as substituents.

Arylalkyl groups are alkyl groups substituted with one or more aryl groups wherein the alkyl groups optionally carry additional substituents and the aryl groups are optionally substituted. Specific alkylaryl groups are phenyl-substituted alkyl groups, e.g., phenylmethyl groups. Alkylaryl groups are alternatively described as aryl groups substituted with one or more alkyl groups wherein the alkyl groups optionally carry additional substituents and the aryl groups are optionally substituted. Specific alkylaryl groups are alkyl-substituted phenyl groups such as methylphenyl. Substituted arylalkyl groups include fully halogenated or semihalogenated arylalkyl groups, such as arylalkyl groups having one or more alkyl and/or aryl groups having one or more hydrogens replaced with one or more fluorine atoms, chlorine atoms, bromine atoms and/or iodine atoms.

As to any of the groups described herein which contain one or more substituents, it is understood that such groups do not contain any substitution or substitution patterns which are sterically impractical and/or synthetically non-feasible. In addition, the compounds of this invention include all stereochemical isomers arising from the substitution of these compounds. Optional substitution of alkyl groups includes substitution with one or more alkenyl groups, aryl groups or both, wherein the alkenyl groups or aryl groups are optionally substituted. Optional substitution of alkenyl groups includes substitution with one or more alkyl groups, aryl groups, or both, wherein the alkyl groups or aryl groups are optionally substituted. Optional substitution of aryl groups includes substitution of the aryl ring with one or more alkyl groups, alkenyl groups, or both, wherein the alkyl groups or alkenyl groups are optionally substituted.

Optional substituents for any alkyl, alkenyl and aryl group includes substitution with one or more of the following substituents, among others: halogen, including fluorine, chlorine, bromine or iodine; pseudohalides, including —CN;

—COOR where R is a hydrogen or an alkyl group or an aryl group and more specifically where R is a methyl, ethyl, propyl, butyl, or phenyl group all of which groups are optionally substituted;

—COR where R is a hydrogen or an alkyl group or an aryl group and more specifically where R is a methyl, ethyl, propyl, butyl, or phenyl group all of which groups are optionally substituted;

—CON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—OCON(R)$_2$ where each R, independently of each other R, is a hydrogen or an alkyl group or an aryl group and more specifically where R is a methyl, ethyl, propyl, butyl, or phenyl group all of which groups are optionally substituted; and where R and R can form a ring which can contain one or more double bonds and can contain one or more additional carbon atoms;

—N(R)$_2$ where each R, independently of each other R, is a hydrogen, or an alkyl group, or an acyl group or an aryl group and more specifically where R is a methyl, ethyl, propyl, butyl, phenyl or acetyl group, all of which are optionally substituted; and where R and R can form a ring which can contain one or more double bonds and can contain one or more additional carbon atoms;

—SR, where R is hydrogen or an alkyl group or an aryl group and more specifically where R is hydrogen, methyl, ethyl, propyl, butyl, or a phenyl group, which are optionally substituted;

—SO$_2$R, or —SOR where R is an alkyl group or an aryl group and more specifically where R is a methyl, ethyl, propyl, butyl, or phenyl group, all of which are optionally substituted;

—OCOOR where R is an alkyl group or an aryl group;

—SO$_2$N(R)$_2$ where each R, independently of each other R, is a hydrogen, or an alkyl group, or an aryl group all of which are optionally substituted and wherein R and R can form a ring which can contain one or more double bonds and can contain one or more additional carbon atoms;

—OR where R is H, an alkyl group, an aryl group, or an acyl group all of which are optionally substituted. In a particular example R can be an acyl yielding —OCOR" where R" is a hydrogen or an alkyl group or an aryl group and more specifically where R" is methyl, ethyl, propyl, butyl, or phenyl groups all of which groups are optionally substituted.

Specific substituted alkyl groups include haloalkyl groups, particularly trihalomethyl groups and specifically trifluoromethyl groups. Specific substituted aryl groups include mono-, di-, tri, tetra- and pentahalo-substituted phenyl groups; mono-, di-, tri-, tetra-, penta-, hexa-, and hepta-halo-substituted naphthalene groups; 3- or 4-halo-substituted phenyl groups, 3- or 4-alkyl-substituted phenyl groups, 3- or 4-alkoxy-substituted phenyl groups, 3- or 4-RCO-substituted phenyl, 5- or 6-halo-substituted naphthalene groups. More specifically, substituted aryl groups include acetylphenyl groups, particularly 4-acetylphenyl groups; fluorophenyl groups, particularly 3-fluorophenyl and 4-fluorophenyl groups; chlorophenyl groups, particularly 3-chlorophenyl and 4-chlorophenyl groups; methylphenyl groups, particularly 4-methylphenyl groups; and methoxyphenyl groups, particularly 4-methoxyphenyl groups.

The compounds used in the methods of this invention can contain one or more chiral centers. Accordingly, this invention is intended to include racemic mixtures, diasteromers, enantiomers, tautomers and mixtures enriched in one or more stereoisomer. The scope of the invention as described and claimed encompasses the racemic forms of the compounds as well as the individual enantiomers and non-racemic mixtures thereof.

"Inactivate" in the context of the methods provided herein refers to a process by which an organism or microorganism is rendered incapable of reproducing, growing and/or surviving. In some embodiments, active agents of the present invention, such as organophosphates, inactivate *Demodex brevis* mites, *Demodex folliculorum* mites and/or larva and/or eggs thereof. In some embodiments, inactivation results in death or elimination of *Demodex brevis* mites, *Demodex folliculorum* mites and/or larva and/or eggs thereof. In other embodiments, the inactivation selectively targets one phase of the mite lifecycle. In this manner, multiple applications that are spaced in time can be beneficial in controlling mite population, so that mites at different stages of the life cycle may then be appropriately targeted. For example, an application that targets an adult mite may not effectively control larvae or eggs can be addressed by a subsequent therapeutic application of the organophosphate timed to ensure that a subsequent generation of mites from an earlier life cycle phase are targeted. Similarly, applications that target eggs or larvae may be timed to target subsequent generations of eggs or larvae. Accordingly, inactivate includes aspects where there is only partial inactivation of a mite population, but that a more complete inactivation occurs with subsequently timed treatments.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, -32-cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids, including but not limited to cysteine. Other pharmaceutically acceptable salts may be found, for example, in Stahl et al., Handbook of Pharmaceutical Salts: Properties, Selection, and Use, Wiley-VCH; Verlag Helvetica Chimica Acta, Zürich, 2002. (ISBN 3-906390-26-8). Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include among other halides (e.g., $Cl^-$, $Br^-$), sulfate, acetates (e.g., acetate, trifluoroacetate), ascorbates, aspartates, benzoates, citrates, and lactate.

DETAILED DESCRIPTION

Figure 1:
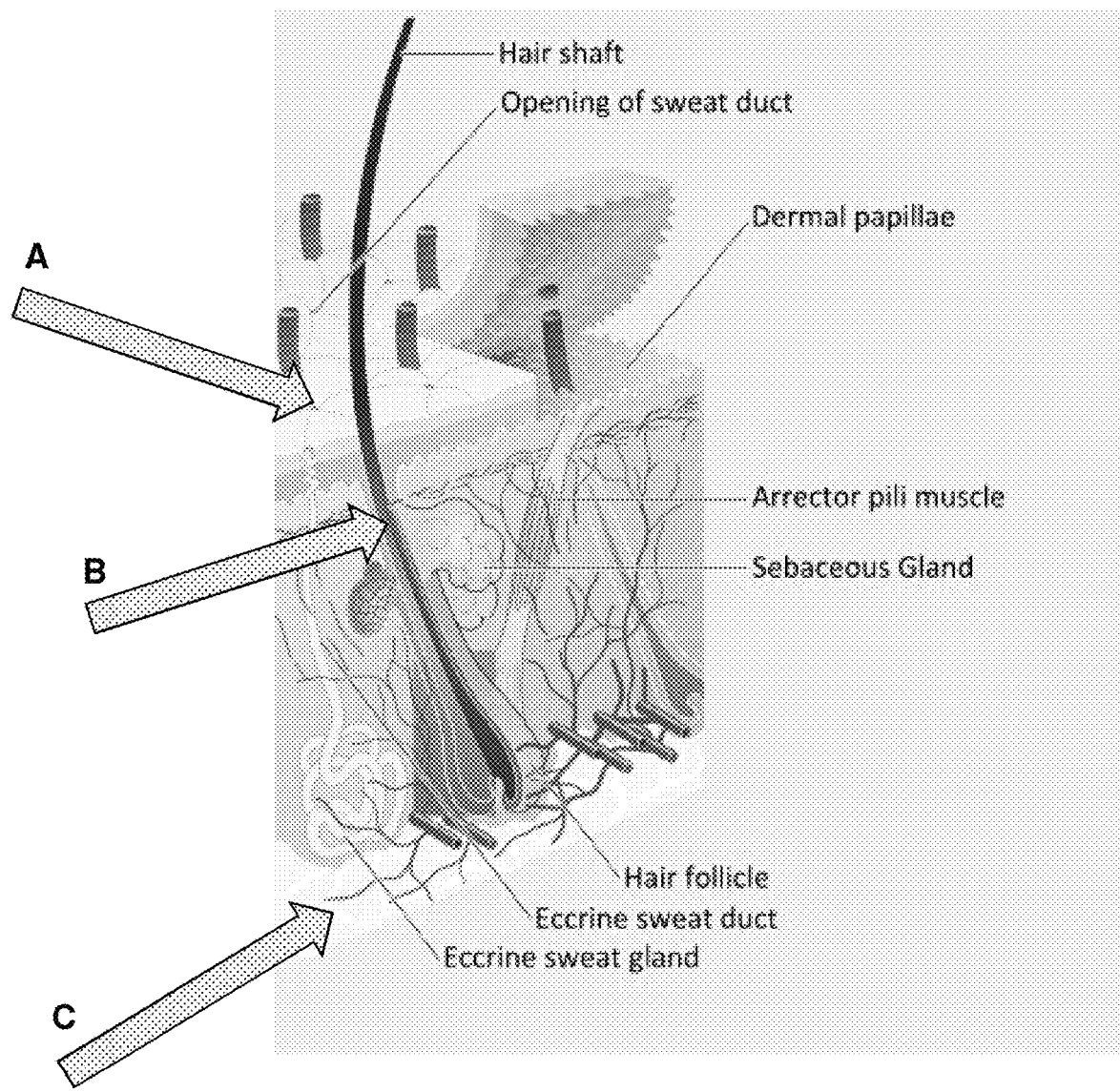
FIG. 1 is a schematic illustration of the various routes of administration: A. Topical administration to the epidermis; B. Subdermal administration; C. Oral administration.

In general, the terms and phrases used herein have their art-recognized meaning, which can be found by reference to standard texts, journal references and contexts known to those skilled in the art. The following definitions are provided to clarify their specific use in the context of the invention.

"Treating" refers to a therapeutic application of an organophosphate to at least decrease adverse symptoms caused by the presence of demodex bevis and/or folliculorum mites. As described herein, there are various observable symptoms, referred herein as "clinical symptoms", associated with the mites, particularly on the face. The treatment or treating methods described herein may alleviate or at least substantially attenuate any one or more of those clinical symptoms. Categories of those symptoms may not be directly caused by the mite, but instead may arise indirectly due to the presence of mites, and may include an immunological response such as an allergic response and/or a vasomotor response. For example, a response to mites may include a dilation of surface blood vessels to increase blood flow to the region of the face from which an immune signal is generated, thereby resulting in an observable appearance of flushing or redness of the skin. Similarly, an overly robust immune response can lead to typical symptoms related to immunological responses, including inflammation, itching, irritation, scarring, and the like. Other physical manifestations of those symptoms may further include acne and the like. The mites themselves may not directly cause the clinical symptom, but instead may trigger an immune response which then causes the clinical symptom. Similarly, a bacteria or other pathogen carried by the mite may cause the clinical symptom and the treatment that inactivates mite populations may alleviate the clinical symptom after a certain time post-application.

"Clinical symptom", therefore, refers to a physical, detectable, measurable or observable adverse or unwanted condition associated with the mite-responsible skin affliction. In an aspect, it is a skin condition that is observable. The clinical symptom may further be assessed by the individual, such as by a feeling of pain, burning sensation, itching, or other discomfort expressed by the individual. The methods provided herein are useful for attenuating, alleviating or cessation any such clinical symptoms.

"Attenuating" or "ameliorating" refers to a measurable or quantifiable reduction in the clinical symptom. For example, the individual can indicate whether the feeling of discomfort is reduced. Alternatively or in addition, the reduction may be measured, such as by a reduction in skin discoloration, scarring, or other skin abnormality. As desired, the attenuation may have a quantifiable decrease, such as a decrease of at least 50% compared to pre-treatment. An initial attenuation may then be followed by cessation of the clinical symptom. "Cessation" refers to essentially a disappearance of the clinical symptom such that there is no longer an observable symptom and/or the individual does not have a feeling of discomfort otherwise associate with the skin affliction.

As used herein, the term mite refers to a demodex mite, and more particularly for some embodiments a Demodex brevis (D. brevis) mite and/or a Demodex folliculorum (D. folliculorum) mite found in or on the skin of an individual. Because these mites are found in humans, an aspect of any of the treatment methods provided herein is for an individual that is a human.

As outlined herein, D. folliculorum and D. brevis mites play a role in the rosacea condition. An increased demodex population has been observed in rosacea patients. For most people, demodex mites live harmlessly in the skin as a result of either down-regulating host immunity or simply dodging host immune defenses. There is vociferous debate within the dermatology community as to whether or not they are the causative agents of such skin diseases as rosacea and blepharitis (inflammation of the eyelids) a common issue seen in rosacea patients.

Human beings are the one and only host of this ubiquitous mite [2]. In fact, these two mites are considered to be the most common ectoparasite of humans [5]. Women tend to have a higher rate of *demodex* infections [4]. The rate of infestation also seems to be correlated with age, with 84% of people at age 60 harboring mites and increasing to 100% in those 70 years and older [6]. Whether those that are immunocompromised are more susceptible to higher infestation rates is unknown, though some studies indicate that AIDs and leukemia patients may be more prone to greater than average numbers [4].

The mites are most commonly found in the scalp, face and upper chest area, with *D. folliculorum* exhibiting a predilection for the hair follicles and *D. brevis* for the sebaceous ducts and meibomian glands at the rim of the eyelids (the sebaceous ducts transfer the waxy sebum that lubricates the skin and hair from the sebum glands; the meibonmian glands are a special type of such gland) [3][4]. *D. folliculorum* are a communal bunch, tending to congregate in the follicle area of the hair or eyelashes with their posterior ends protruding from the follicular pores. *D. brevis*, on the other hand, tend to be more solitary and will occupy the sebaceous glands singly [5]. Both species are tiny, less than 0.4 mm, with elongated, clear bodies and four pairs of stout legs. *D. brevis* is usually a tad shorter, ~0.1 mm, than *D. folliculorum*. They both have ridged scales along their cephalothorax and sharp, piercing teeth[5].

Short-lived creatures, a mite's life cycle from egg to larva to adult typically lasts on the order of weeks depending on environmental conditions, such as from about 14-24 days, or from 14-18 days. Adults emerge from the follicles and ducts to reproduce at the surface of the skin where females will then deposit eggs in the sebaceous glands. Larva will mature via two nymphal stages in the glands until entering the follicles and ducts as adults to begin the cycle anew [5]. It is hypothesized that both species of mites feed upon sebum as a primary food source but may also feed on follicular and glandular epithelia. The mites are sometimes characterized as obligate ectoparasites, incapable of living outside their human host.

Studies indicate a greater than average mite density, such as greater than five mites per cm², play a role in these two diseases for patients [5]. Research suggests that blockage of the hair follicles and sebaceous ducts by mites may result in epithelial hyperplasia, elicit a phagocytic, granulomatous reaction or bring an inflammatory response due to their waste products [5]. The fact that treatment with certain antibiotics can reduce the severity of rosacea suggests a microbial component to mite-related diseases. For example, researchers isolated from *D. folliculorum* a bacterium *Bacillus oleronium* that provoked inflammatory responses in 73% of rosacea patients but only 29% of controls [20]. These results suggest that patients with rosacea are sensitized to the bacteria and may be immunologically sensitive to the mites, bacteria or both [20].

Two antigenic proteins found on the bacterium's cell surface in particular appear responsible for the inflammatory response by stimulating peripheral blood mononuclear cell proliferation; one 83 kDa protein showed similarity with heat-shock proteins while the other 62 kDa protein shared amino acid sequence homology with a protease enzyme found to be involved signal transduction as well as carbohydrate metabolism [20]. Additional indication of the pathogenic role of *B. oleronius* in rosacea may also be found in the sensitivity of the bacterium to many antibiotics shown to be effective in the treatment of rosacea, specifically tetracycline, doxycycline and minocycline[20].

Examples of classic rosacea symptoms include: persistent redness, flushing especially with common rosacea triggers (cosmetics, stress, alcohol, heat, sun exposure, exercise, spicy foods), telangiectasias on the nose and cheeks, bumps and pimples, dry appearance, tight or swollen skin, burning and itching skin.

According to the national Rosacea Society seborrheic (seb-oh-REE-ick) dermatitis may be the most common skin condition to occur at the same time as rosacea. Although the two disorders are thought to be unrelated, a recent clinical study found that 26 percent of patients with rosacea also had facial seborrheic dermatitis and 28 percent had seborrheic dermatitis of the scalp. Additionally, a survey by the National Rosacea Society of 1,099 rosacea patients found that 25 percent had also been diagnosed with this condition [1].

A study identified a *bacillus* bacterium inside Demodix mites, where the bacteria releases two proteins that trigger an inflammation in patients with facial rosacea." [37]. At least one type of bacteria is associated with *demodex* mites and rosacea. This bacteria is *Bacillus oleronius* according to an NRS press release[38] ("This indicates that the *Bacillus* bacteria found in the *Demodex* mite produce an antigen that could be responsible for the tissue inflammation associated with papulopustular rosacea.") Other studies state, "Antigenic proteins related to a bacterium (*B. oleronius*), isolated from a *D. folliculorum* mite, have the potential to stimulate an inflammatory response in patients with papulopustular rosacea." [39]; and "The strong correlation provides a better understanding of comorbidity between *Demodex* mites and their symbiotic *B oleronius* in facial rosacea and blepharitis." [40]

Potential causes of rosacea include increased facial bloodflow, altered response patterns of facial bloodflow, photo damage, oxygen free radical, UV light exposure, heat exposure, the proliferation of *Demodex* mites, *Helicobacter pylori* infection, differences in bacterial proteins found in association with inflammatory lesions of rosacea, and the proinnflammatory bacterium *Bacillus oleronius* found in the gut of the *demodex* mites more commonly in rosacea-affected facial skin.[64] Due to limited basic science research on rosacea, the validity and/or magnitude of the role of these potential causes in the pathogenisis of rosacea has been debated.[64]

The pathophysiologic mechanisms of rosacea are difficult to research because there are major pitfalls in laboratory techniques used to study the disease. With gene array expression analysis as a rough indicator of change in mRNA levels of multiple genes, results may or may not correlate with a protein of interest. Similarly RT-PCR a more specific indicator of changes in mRNA, but results may or may not correlate with production or activity of a protein of interest. Using Immunohistochemistry the immunoreactivity may not be uniform within a specimen and data presented may be subject to selection bias or lack of specificity depending on the quality of the antibody. Zymography results depend on proper incubation and digestion techniques. No robust animal models exist for rosacea; assays used in animals are surrogates for some putative aspects of rosacea pathophysiology. Finally, cell culture is difficult because multiple cell types within and surrounding the follicle are involved in rosacea; interactions between cell types cannot be modeled with current cell culture techniques.[64]

*Demodex folliculorum* and *D. brevis* are cosmopolitan, obligatory parasites. Epidemiological studies have established a clear association between these species and various facial diseases in humans. However, not much is known of the ecology of these mites. One reason for this is because it is difficult to culture the mites.[65] There are few studies on the ecology of *D. folliculorum* and *D. brevis*, and maintenance in vitro has not been successfully achieved. Empirical studies lack large numbers of standard *D. folliculorum* and *D. brevis*, which critically restricts further study of their pathogenicity. For a long time, the only means to obtain *D. folliculorum* and *D. brevis* samples was to conduct a census using the cellophane tape method, which is time-consuming and labor-intensive. In addition, the *D. folliculorum* and *D. brevis* obtained in this manner may not meet the requirements for standard experiments and cannot be kept for long due to their aptness to die. [66] Because animal and in vitro models are not available for D. *Folliculorum* and *D. brevis* mites, with the mites tending to die off after about 60 to 80 hours at most, basic research with the mites is difficult and not practical.

The fundamental understanding that *demodex* may be a systemic cause of rosacea indicates a natural treatment with a known miticide, such as tea tree oil [43], may assist with symptom alleviation. Tea tree oil may be applied using several formulations, including 100%. The tea tree oil assists with blepharitis but is not well tolerated by skin, especially in higher concentrations. The redness, scaling and erythema associated with demodatic skin afflictions will persist post treatment even with 100% tea trea oil. To better understand the efficacy of the treatments provided herein, it is useful to understand the current state of the art with respect to other treatments.

Example 1

Prescription Drugs Used to Treat Rosacea. Table 3 summarizes drugs prescribed by dermatologists for the treatment of rosacea, and further explanation is provided below.

1. Antibiotics: Antibiotics are the most common rosacea drugs. Antibiotics are prescribed in the form of pills or creams. If the condition is severe, pills are prescribed along with cream. Oral antibiotics work faster than topical creams, so oral antibiotics are usually prescribed for relatively quick relief. Erythromycin, doxycycline, minocycline, and tetracycline are examples of commonly prescribed oral antibiotics. Examples of oral and topical antibiotics are provided in Table 1 and 2.

2. Isotretinoin: Isotretinoin is usually prescribed for severe cases of rosacea. Isotretinoin treatment is generally prescribed only if the disease fails to respond to an antibiotic treatment course. Isotretinoin is a strong oral medication that hampers the production of oil by sebaceous glands. Pregnant women should avoid taking isotretinoin, as it has severe side effects resulting in miscarriage or birth defects.

3. Tretinoin: Tretinoin, also known as Renova, Retin-A or Avita, is a topical medicine used as a rosacea drug. It is a common medication for acne. Use of tretinoin reduces fine wrinkles and smoothes rough facial skin. Also known as vitamin A acid or retinoic acid, tretinoin comprises vitamin A and comes in three forms—liquid, gel, and cream.

4. Benzoyl peroxide: This medication is usually used to treat acne and is also used for rosacea. Benzoyl peroxide reduces the amount of bacteria on the skin.

5. Finacea: (azelaic acid) gel, 15% is another topical drug for rosacea, which is again used topically on the skin.

6. Mirvaso: (brimonidine) topical gel, 0.33%*Galderma the manufacturer of Oracea one of the most popular rosacea drugs just recently cleared the vasoconstrictor brimonidine a drug used by Manufacture Allergan for the treatment of glaucoma.

Example 2: Organophosphates

In an embodiment of this invention, organophosphates, such as dichlorvos, are administered topically to a patient with an active skin condition in which the underlying cause is a *demodex* mite, such as a *Demodex brevis* and/or *Demodex folliculorum* mite. Because the target organisms, *Demodex brevis* and *Demodex folliculorum*, are ectoparasites in the mite family, an effective treatment must be capable of inactivating or eradicating substantially the entire lifecycle of such a microscopic insect, including egg, larval, and adult stages, for long-term efficacy. For this reason, this embodiment treats such patients with several doses. Such spacing allows time for *demodex* eggs that may not inactivate as a result of the organophosphate application, to hatch into immature mites that are killed before they can mature into egg-producing adults. After the organophosphate carries out its miticidal activity on skin *Demodex brevis* and *Demodex folliculorum* organisms, inflammatory responses to them begin to diminish but remnants of the dead mites still elicit responses observed as clinical symptoms, such as some flushing and lesion formation, until the cleanup processes of the body remove them, a process requiring six to eight weeks. During this initial phase of organophosphate administration, conventional anti-rosacea medications such as oral tetracycline and topical metronidazole can optionally be employed to suppress early flareups and to provide early clinical improvement and response. No such medications are needed to treat manifestations of rosacea after six to eight weeks have elapsed. After prolonged intervals of freedom from rosacea symptoms, should classic signs begin to reappear, treatment can be repeated. The organophosphate is formulated into a cosmetically-acceptable topical lotion, cream, shampoo, or gel and applied especially to skin affected by rosacea and any area possibly inhabited by *Demodex brevis* and *Demodex folliculorum*. Because of the barrier effect the skin presents to the penetration of topical medications, such a route of treatment with organophosphate is anticipated to require once or twice daily applications for as long as six weeks to achieve sufficient follicle penetration and effective miticidal activity. A topical formulation that could achieve this effect may contain 5% or less of the organophosphates. Lower percentages of organophosphate that retains sufficient miticidal effect and successful skin condition treatment is preferred so as to limit or minimize potential side effects of the organophosphate. Further, full body treatment is optionally useful for preventing reintroduction of the mites onto skin, such as facial skin, from other body locations that may not present clinical symptoms.

FIG. 1 is an illustration of the different administration routes, as indicated by arrows labelled A, B and C. In an aspect, the treatment is by topical administration to the skin (A). The topical administration may be to an afflicted region showing clinical symptoms, to an unafflicted region that does not show a clinical symptom, or to both. The reason for application to an unafflicted region is that there may likely be mites present but no clinical symptom appears. Those mites, however, may reproduce and repopulate the previously treated regions, thereby potentially decreasing the treatment efficacy or overall length that the treatment remains effective. B reflects a subdermal treatment, such as administration to hair follicles or into pores. The subdermal application may be into a dermis layer, a subcutaneous layer, or a hypodermis layer. C represents the results of oral or rectal administration where the active agent of the treatment is delivered to the skin via the bloodstream.

Figure 2:
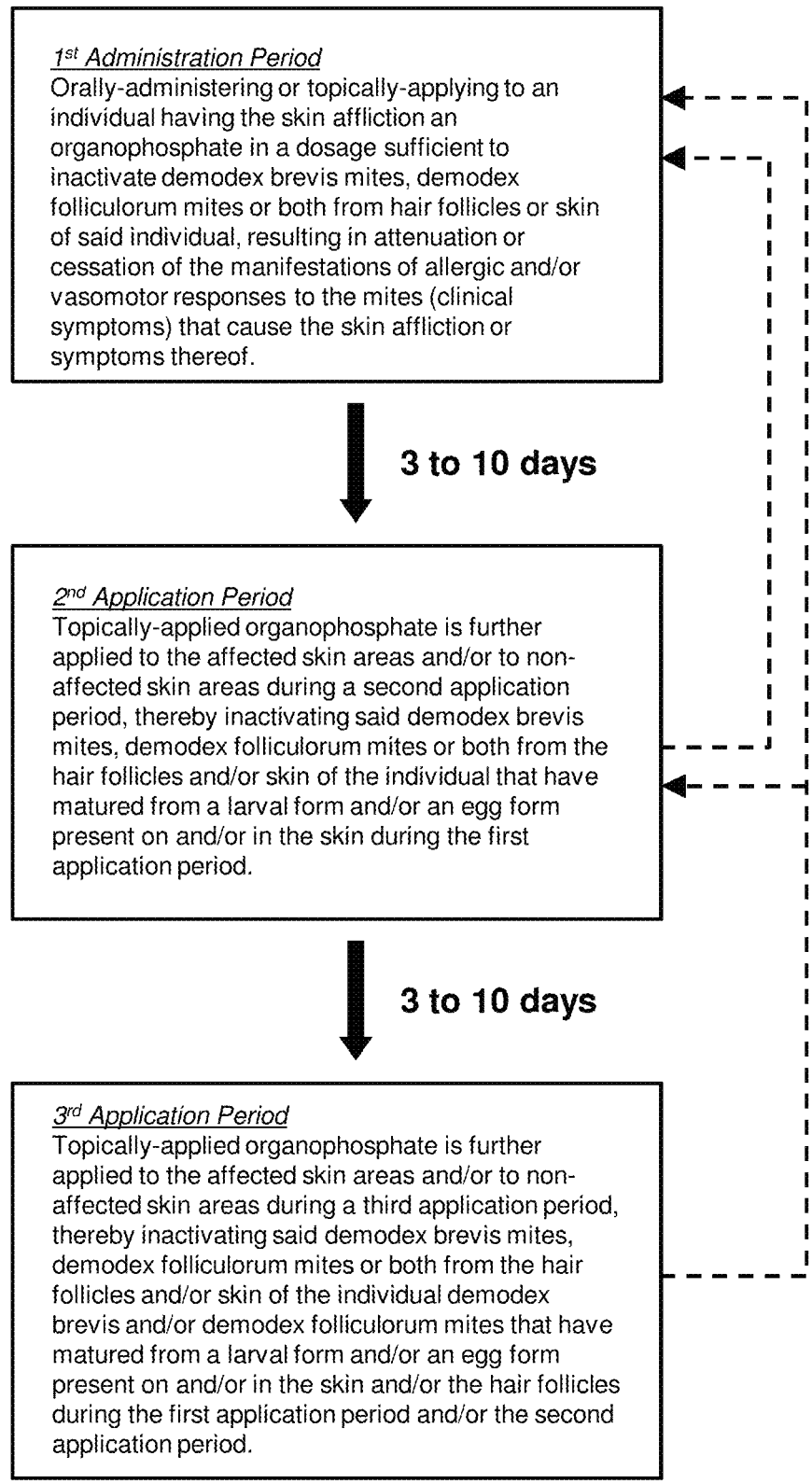
FIG. 2 is a schematic illustration of the method of treatment.

FIG. 2 is a process flow diagram showing repeated application steps to ensure more complete treatment and control of mites. Each of the steps may be separated by a time period of between about 5 to 10 days. Each administration, however, may have multiple applications, such as two topical applications and washes within a day to ensure adequate dose over the individual's skin surface. The repeated administrations, in contrast, recognize that the organophosphate may not reliably kill non-adult mites. For examples, the administration may not prevent fertilized eggs from hatching. Accordingly, even if an entire population of adult mites is incapacitated or killed, one application may be insufficient if mites hatch from eggs after the first application. Accordingly, a follow-up application after about 5 to 10 days from the first may inactivate this second generation of mites. A third application may provide even more reliable population control, such as for eggs that may have been laid by the second generation mites before the second application was effective, or mites that otherwise escaped the initial applications.

Figure 3:
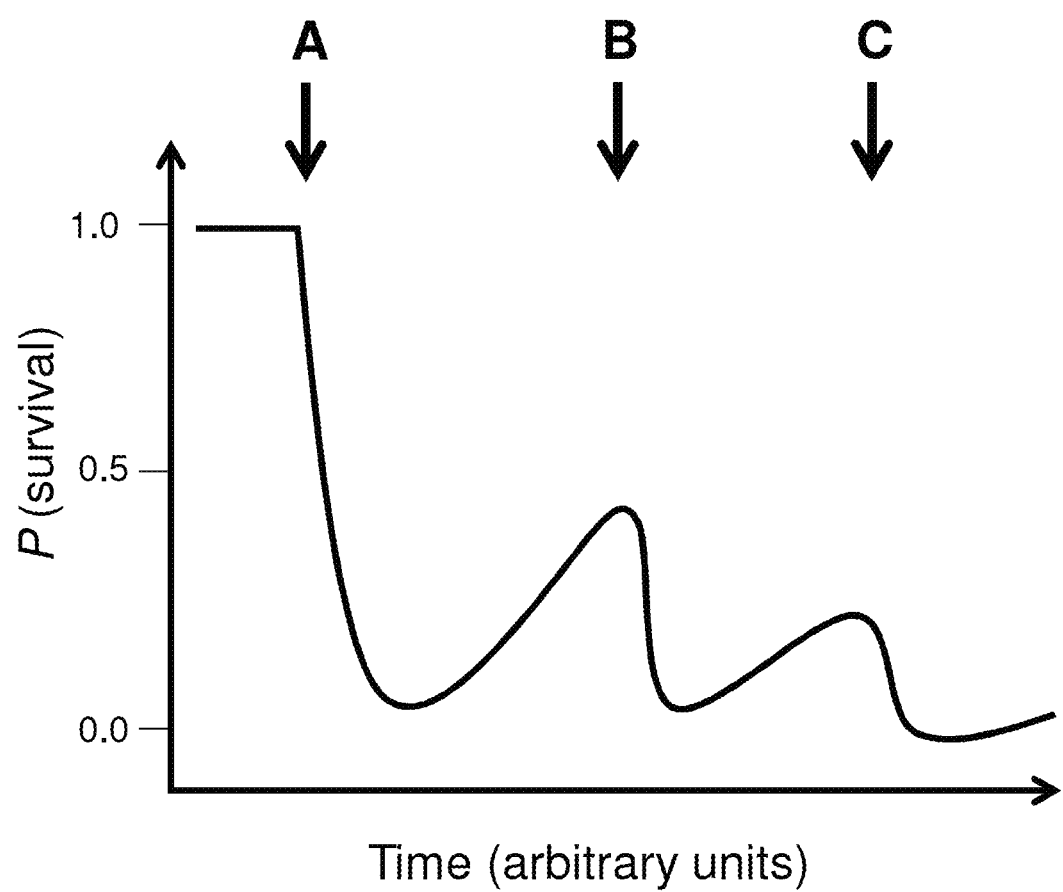
FIG. 3 is a schematic diagram representing a dosing regimen of the present therapeutic methods including repeated, and optionally periodic, administration of a therapeutic agent containing an organophosphate active ingredient to an individual afflicted by, or susceptible to, a dermatological condition such as Rosecea.

FIG. 3 is a schematic diagram representing a dosing regimen of the present therapeutic methods including repeated, and optionally periodic, administration of a therapeutic agent containing an organophosphate active ingredient to an individual afflicted by, or susceptible to, a dermatological condition such as rosacea. In the plot shown in this figure, the population of *demodex* mites (P(survival)) corresponding to treated regions of the skin and/or hair of the individual is plotted as a function of time (arbitrary units). Arrows A, B and C indicate times wherein the therapeutic agent containing the organophosphate active ingredient is administered to regions of the skin and/or hair of the individual displaying symptoms of the condition, and optionally for some embodiments, regions of the skin and/or hair of the individual wherein symptoms of the condition are absent or to be prevented.

A first rapid and large drop in the population of *demodex* mites occurs upon a first administration of the therapeutic agent containing the organophosphate active ingredient as represented by arrow A. The first administration results in a significantly reduced population of *demodex* mites (P(survival)) corresponding to treated regions of the skin and/or hair of the individual and is followed by a gradual increase of the population of *demodex* mites as a function of time which may occur via maturation of eggs present on, or in, the individual and/or infestation of mites from another source of mites (e.g., contact with another individual, pet, or other environmental factor). A second rapid and large drop in the population of *demodex* mites occurs upon the second administration of the therapeutic agent containing the organophosphate active ingredient as represented by arrow B, thereby, preventing the population of mites to reach the original levels. This second drop is also followed by a gradual increase of the population of *demodex* mites as a function of time which may occur via maturation of eggs present on, or in, the individual and/or infestation of mites from another source of mites (e.g., contact with another individual, pet, or other environmental factor). However, the recovery of the mite population occurs to a level less than the original level or the first recovery level. A third rapid and large drop in the population of *demodex* mites occurs upon the third administration of the therapeutic agent containing the organophosphate active ingredient as represented by arrow C. As shown in FIG. 3, periodic readministration of the therapeutic agent containing the organophosphate active ingredient provides an effective means of lowering, and maintaining, the population of mites to a significantly reduced level, for example, to a level sufficiently reduced to prevent, or ameliorate symptoms associated with, a dermatological conditions such as rosacea.

Example 3: Topical Dichlorvos Treatment

One example of an organophosphate useful in addressing mite infestations in plants is dichlorvos (DDVP) and is capable of completely wiping out a heavy spider mite infestation, especially within a greenhouse. DDVP is also known as the drug metrifonate, is an irreversible organophosphate acetylcholinesterase inhibitor. Metrifonate is a prodrug which is activated non-enzymatically into 2,2-dichlorovinyl dimethyl phosphate.

A 1% dichlorvos (DDVP) treatment to skin is applied as a wash every 3 days. DDVP may be left on the skin for a time period, such as about 2-3 minutes, and subsequently washed. Initial flare up is observed, followed very quickly by resolution of many clinical symptoms after using the wash on both the entire body and face. To clear an infestation, it is beneficial to treat the entire body and not too confine the treatment to those skin portions having the clinical symptoms.

Patient 1. A 30 year old Caucasian male, weighing about 83 kg, exhibiting clinical evidence of rosacea for 3 years and had been treated with limited success with oral tetracycline and topical metronidazole and topical cortisones. Facial skin exhibits midfacial erythema and flushing with papule and pustule formation. In addition, eyelids exhibit chronic blepharitis. Skin scaling and flaking, such as on the ears, is one clinical symptom. This is a rosacea symptom that may not go away with any treatment regimen. It is important to understand that seborrheic dermatitis much like rosacea has no clear etiology. Examples of prior treatments include topical corticosteroids, topical retiniods, topical benzyl peroxide, topical clindamycin, oral tetracycline, oral doxycycline, topical metronidazole, topical erythromycin, 595 pulsed dye laser surgery. The steroids made the condition worse or more aggravated. Topically with clindamycin, little sign of clinical symptom improvement occurred, but there was favorable reaction to metronidazole and even better reaction to erythromycin. With multiple (e.g., four) cycles of oral antibiotics, good response was observed with the first two cycles, but the third was less effective in treating facial redness and swelling, and the fourth was generally ineffective. Side effects of oral antibiotics include moderate to severe stomach issues with the last cycle requiring discontinued use towards the end of the cycle. The 595 pulsed dye laser helped correct the telangiectasias and temporarily helped with inflammation but was painful and costly. Instant treatment comprises topical application with the organophosphate dichlorvos, 1% solution by weight with a volumetric application of between about 5 mL to 10 mL so as to provide about 0.6 mg/kg of body weight to about 1.2 mg/kg of body weight. The application can be for an application time, such as about 2 minutes, after which the topical treatment areas are rinsed. The treatment may be biweekly, such as application to the dermis every 3 to 4 days for about 12 weeks. After an initial flareup of midfacial papules, the condition improves rapidly to the point that by 12 weeks no papules are present and no more flushing with heat, spicy foods or other reported rosacea flare triggers occurred. Long term symptoms expressed over the course of years cleared and completely disappeared with dichlorvos treatment wash. Most notably the pores on the nose and the nose as a whole seemed to shrink. Scaling on the chin and inside the ears disappeared completely. Finally, redness, erythema and postules cleared from cheeks and chin. The most relieving part of the treatment is the cessation of the itching and burning; after just a few treatments skin has a different feel and look. Of all available treatment options, the DDVP wash treatment regimen was the fastest acting and most effective for the condition that had plagued the patient for years. Symptoms had not returned after 6 months post-treatment.

Metrifonate/Dichlorvos (DDVP) Properties: I. Efficacy. Important Pests Controlled: Ants, aphids, mites, mealybugs, ticks, *Drosophila*, centipedes, moths, cockroaches, crickets, fleas, flies, gnats, mosquitoes, sowbugs, spiders, wasps and many others [7]; Extremely fast knock-down effects. Residual control of 2-3 weeks may be obtained [7].

II. Physical properties. MOLECULAR FORMULA: $C_4H_7Cl_2O_4P$ [8]; MOLECULAR WEIGHT: 221.0 [8]; PHYSICAL STATE: Colorless to amber liquid (pure compound) [8]; ODOR: Aromatic odor (pure compound) [8]; BOILING POINT: 35 C/0.05 mmHg (pure compound) [8]; VAPOR PRESSURE: 1.6 Pa at 20 C (pure compound) [8]; SOLUBILITY: c.10 g/l water at 20 C (pure compound) [8].

III. Health Hazard Information. OSHA STANDARD: 1 mg/m$^3$ averaged over an 8-hr work shift [9]; NIOSH RECOMMENDED LIMIT: None established; ACGIH RECOMMENDED LIMIT: TWA (Time Weighted Average)=0.1 ppm, 1 mg/m3; STEL (Short Term Exposure Limit)=0.3 ppm (deleted), 3 mg/m3 (deleted); skin notation [10].

IV. Toxicology. A. ACUTE TOXICITY. DERMAL: LD50=70.4 to 250 mg/kg (rat); 107 mg/kg (rabbit) [11]; LD50=75-210 mg/kg (rat) [8]; ORAL: LD50=56-108 mg/kg (rat) [8], 61 to 175 mg/kg in mice, 100 to 1090 mg/kg in dogs, 157 mg/kg in pigs, 11 to 12.5 mg/kg in rabbits; LD50=; INHALATION: LC50 (4-hr): 13.2 mg/m$^3$ (mouse); 14.8 mg/m$^3$ (rat) [8]; EYES: Not known to be an eye irritant [9].

B. SUBACUTE AND CHRONIC TOXICITY: Daily exposure to concentrations which are insufficient to produce symptoms following a single exposure may result in the onset of symptoms. Continued daily exposure may be followed by increasingly severe effects.

In a study of 13 workers exposed for 12 months to an average concentration of 0.7 mg/m$^3$, the erythrocyte cholinesterase activity was reduced by approximately 35%, and the serum cholinesterase activity was reduced by 60%; the results of other tests and of thorough medical examinations conducted at regular intervals were entirely normal[9]. In 90-day feeding trials rats receiving 1000 mg/kg diet showed no intoxication[8].

Relatively extensive toxicity studies on dichlorvos is available. See, for example, Sekizawa et al. International Programme on Chemical Safety. Environment Health Criteria 79. Dichlorvos "Environmental Health Criteria for Dichlorvos" WHO. Geneva (1989).

Example 4: Treatment with Organophosphates Having Insecticidal Activity

While the DDVP example illustrates one embodiment of this invention, the treatment of rosacea using topical organophosphates, exposure of *Demodex* mites to organophosphates from any route of administration will result in the elimination of the organisms and secondary amelioration of the signs of inflammation that are typical of rosacea. Therefore, the topical use of organophosphates in any vehicle that allows it to adequately penetrate into skin follicles to reach the level occupied by *demodex folliculorum* will be an effective treatment for rosacea and, therefore, is within the scope of this invention. Changes to dosage, dosing schedule, concentration, vehicle, and frequency of repetition of dichlorvos regimen, is similarly encompassed within the scope of the invention. Based on clinical evidence, rosacea and its subtypes and other skin conditions, such as common acne, seborrheic dermatitis, perioral dermatitis, an acneform rash, transient acantholytic dermatosis, acne necrotica milliaris, psoriasis, steroid induced dermatitis, and primary irritation dermatitis, may have, at least in part, a common etiology of *Demodex brevis* and *Demodex folliculorum* and immune responses associated with the bacteria specifically related to the *demodex* mites. Accordingly, the discovery herein of the fundamental treatment pathway for the skin affliction rosacea, caused by mites, indicates use of organophosphates having insecticide capability to lower the populations of and eradicate *Demodex brevis* and *Demodex folliculorum* mites from the skin. The following are known organophosphates and may be used with any of the instant treatment methods provided herein.

Useful organophosphates include, but are not limited to: acephate, azamethiphos, azinphos ethyl, azinphos methyl, bromophos, bromophos ethyl, cadusofos, carbophenythion, chlormephos, chlorphoxim, chlorpyrifos, chlorpyrifos-methyl, chlorthiophos, chlorvinphos, croumaphos, crotoxyphos, crufomate, cyanofenphos, cyanophos, demephron-O, demephron-S, demeton-O, demeton-S, demeton-S-methyl, demeton-S-methylsulphon, dialifos, diazinon, dichlofenthion, dichlorvos, dicrotophos, dimefphox, dimethoate, dioxabenzophos, dioxathion, disulfoton, ditalmifos, edifenphos, EPBP, EPN, ESP, ethion, ethopropos, etrimfos, famphur, fenamiphos, fenchlorphos, fenitrothion, fensulfothion, fenthion, fenofos, formothion, fosmethilan, heptenophos, isazofos, isofenphos, isothioate, isoxathion, jodfenphos, leptophos, malathion, menazon, mephosfolan, methacrifos, methamidophos, methidathion, mevinphos, monocrotophos, naled, omethoate, oxydemeton-methyl, parathion, parathion-methyl, phenthoate, phorate, phosalone, phosmet, phosphamidon, phosphamidon amide, phospholan, phoxim, pirimiphos-ethyl, pirimiphos-methyl, profenofos, propaphos, propetamphos, prothiofos, prothoate, pyraclofos, pyridaphenthion, quinlphos, schradan, sulfotep, sulprofos, temephos, TEPP, terbufos, tetrachlorvinphos, thiometon, thionazin, triazophos, trichlorfon and vamidothion.

Example 5: *Demodex* and Rosacea

The etiology of rosacea is still not fully understood, although many theories have been advanced. It has been a frequently discussed topic in medical circles but a full consensus has not ever been reached. The prominent presence of erythema (redness) and flushing of the face of affected persons with aggravation from heat, sunshine, and alcohol has focused attention on this aspect of the disease. The newest and most common hypothesis is based on the characteristic presence of the parasite *Demodex folliculorum* in the case of patients suffering from rosacea. This organism is absent in the other forms of acne such as common acne. Other factors have been described as possibly contributing towards the development of rosacea, such as hormonal factors and especially endocrine factors, climatic and immunological factors, and bacterial factors via the presence of *Helicobacter pylori*, a bacterium associated with gastrointestinal disorders.

Treatment with medications to block such vasomotor flushing have no effect on other aspects of the disease such as papules and pustules. Treatment with oral and topical antibiotics has been shown to effectively block progression of rosacea through a poorly understood anti-inflammatory mechanism or by destroying bacteria associated *Demodex folliculorum* mites. Antibiotics have to be continually administered and are in many cases only marginally effective. Many times patients cannot tolerate the side effects related to the oral antibiotics.

Although hypothesized as a root cause of rosacea, many rosacea subtypes and seborheic dermatitis, *Demodex brevis* and *Demodex folliculorum* there is not consensus regarding the root cause and no commercially viable pharmacological solutions are available for treating *Demodex brevis* and *Demodex folliculorum*. Democodosis presents like rosacea or seborheic dermatitis but is confirmed as being caused by *demodex* mites. Reaction to the presence or metabolic activity of *demodex* mites in facial follicles has long been discussed as a cause of rosacea but previous studies where topical miticides other than organophosphates have been used have shown inconsistent and marginal results.

A study has found that the bacterium *Bacillus oleronius* stimulates an immune system response, inducing high levels of T-cell proliferation, in 79 percent of patients with subtype 2 rosacea, compared with only 29 percent of patients without the disorder. T-cell proliferation induces an inflammatory response, evident as papules and pustules. This suggests that the *Bacillus* bacteria found in the *Demodex* mite produces an antigen that could be responsible for the tissue inflammation associated with papulopustular rosacea. Many current antibiotic treatments for rosacea are theorized to be effective based on their ability to effectively combat *Bacillus oleronius*.

Demodectic rosacea is without question a variant of rosacea when treatment for *demodex* mites improves rosacea. But most rosacea patients are never treated for *demodex* mite and, hence they cannot be ruled out of a rosacea case unless a rosacea patient is treated for *demodex* and does not respond. There is much controversy when a discussion about demodectic rosacea is introduced. While some assert this a theory, the facts are that there are more clinical reports on *demodex* mites and rosacea than any other topic (other than prescription drug treatment). [13] It is an established fact that demodectic rosacea happens since in some cases treatment for *demodex* improves rosacea. Therefore, it is important to rule out demodectic rosacea in a differential diagnosis if you have a red face. One report characterizes it may be a 'missing link' in the understanding of rosacea. [41]

Another report states, "Because *Demodex* mites are ubiquitous, their potential as human pathogens has often been ignored. This contribution focuses on the growing body of evidence linking *Demodex* mites with various skin disorders. Histologically, spongiosis and lymphoid inflammation are regularly seen in follicles containing *Demodex* mites. In animals, they are well established as a cause of mange, and a human counterpart-demodectic alopecia-appears to exist. There is also a statistical association between *Demodex* mite density and rosacea, facial itching, and chronic blepharitis. Papulovesicular rosacea like lesions and spiny blepharitis often respond to agents that reduce *Demodex* numbers. Although these observations are not sufficient to fulfill Koch's postulates, Koch's postulates are also not fulfilled for the association between brown recluse spiders and dermal necrosis or the association between streptococci and guttate psoriasis. The evidence linking *Demodex* mites to human disease has implications regarding treatment." [12]

While there is doubt regarding *demodex*'s role in rosacea (some characterize *demodex* as an 'innocent by-stander') there is growing evidence that demodectic rosacea should be ruled out in every case of rosacea.

*Demodex* and its connection with rosacea is a heavily researched and reported topic. Other relevant topics include clinical reports on metronidazole or other prescription treatments for rosacea. [13] *Demodex* continues to be debated not only by rosaceans but also in the medical community. Some characterize this issue as *demodex* mites being incidental parasites that prey on compromised skin causing secondary symptoms, not unlike bacteria and fungi. Based on this characterization, their opinion is that the *demodex* mites are not the primary cause of rosacea and that not all rosaceans have *demodex* as a relevant factor. Clinicians and researchers further characterize *Demodex folliculorum* as being mentioned as an aggravating factor to rosaceans for many decades and yet, but that no formal double blind studies have addressed this topic. Generally the debate centers on whether *demodex* plays an active role in rosacea or is passive, with the issue being distilled down to which comes first, the rosacea or *demodex*. If *Demodex* is the cause of rosacea, than why don't current miticides work is also a reason the *Demodex* theory is dismissed by many dermatologists. See, e.g., [14] ("Rosacea experts all agree that this mite plays no real role in the development of progression of rosacea."); [15] ("I have always pushed the line that *demodex* mites have thus far only been proven to be innocent bystanders in rosacea symptoms."); and [43] ("The status of *Demodex folliculorum* and its role in rosacea is still an open area of study. It has been difficult to prove that there is or isn't a link between the mite and rosacea. In my mind, *demodex* mites remain as an innocent bystander."). In contrast, see [42] ("We do need more research. *Demodex* have been the subject of an enormous amount of rosacea research, so it pains me to say this!" (describing a study by [Forton F M] which is described in [42] as "in the pure speculation category.")); [59] (titled, "More *Demodex* Dreaming: Mites are the Chicken?"); and [60] (referring to an article published by the NRS, "The Chicken, not the Egg?").

From the above examples, the medical community as well as others view demodectic rosacea as a passive player in rosacea, but there is conflicting evidence.

The methods provided herein recognize demodectic rosacea as an established fact that should be included in any differential diagnosis of rosacea. More and more reports confirm the need to rule out demodectic rosacea. Other possible causes of facial redness include SIBO, hypertension, hyperthyroidism, carciniods, adult acne, allergic reaction and lupus.

Because intense pulsed light (IPL) kills mites [45], in an aspect any of the methods provided herein may further comprise administration of an organophosphate along with co- or post-administration of light, including intense light or intense pulsed light.

Testing for Demodectic rosacea—*Demodex* Density Counts: Techniques are available to non-invasively detect, image and quantify *Demodex* mites in facial skin of patients with rosacea, including confocal laser scanning microscopy. See, e.g., [54] ("With the help of CLSM it is possible to non-invasively detect, image and quantify *Demodex* mites in facial skin of patients with rosacea."). There are, however, "limitations to the use of this method to accurately detect absolute numbers of mites in human skin." [61]

Two other tests include density count and empirical tests by applying a cream like permethrin or crotamiton daily for 2-3 weeks and see if anything unusual happens. The first test, counting mite densities, is not too helpful. A person may have many mites or only a few, but the density test provides no indication if you have a problem with the *demodex*. The test merely counts mites in a random column of extracted skin. A nice number can be produced for a graph for some research papers. The major issue here is a physician may deny treatment if the number does not pass some arbitrary threshold. The second test, the empirical test, is more helpful. If something unusual and significant happens when applying the cream, like a sudden improvement or worsening, then the problem is likely to be linked to the death of *demodex*. If nothing happens, then *demodex* is not a problem and can be excluded.

Papulopustular rosacea (PPR) is similar to demodectic rosacea. It may be an allergy to *demodex* or to a bacteria associated with *demodex*. Some people are allergic, others are not. Unlike other common allergies, this allergen is stuck in the skin as you cannot just choose to avoid *demodex*. It becomes necessary to kill all the mites to bring relief or to suppress the symptoms with a perpetual course of antibiotics. The symptoms of PPR, the red skin, dry skin, blepharitis, and the relentless onslaught of mosquito bite-like papules that sting/tickle are classic allergy symptoms. Once all the mites are dead and are out of the skin, these symptoms stop and the skin returns to normal.

Example 6: Administration and Formulation

Dosing: With respect to treatment with DDVP, a top end of the dosing range can be about 4.5 g or 4500 mg of DDVP. For example, it is reported that humans have ingested 4.5 g of DDVP in a single dose, with few adverse effects, limited to usual cholinergic symptoms but no polyneuritis. Schneider et al. CNS Drug Reviews 5(1):13-26 (1999). Alternatively, the top end of the dosing range may be described in terms of the LD50 in a mammalian animal model, such as rats, pigs or hens.

With respect to lowest effective doses, concentration of DDVP for 50% (ID50) and 80% (ID80) inhibition of AChE in homogenates of mites is reported as $3.4 \times 10^{-8}$ and $10^{-7}$M, respectively. Zahavi et al. Biochemical Pharmacology 19:219-225 (1970). Although the associated relevant topical doses applied to a patient will be correspondingly higher in that the therapeutic needs to penetrate the skin to the location of the mites and traverse the mite exoskeleton to the mite interior to act on AChE, the reported molarity for ID50 or ID80 is a good lowest effective dose amount. In an aspect, the lowest effective dose may be between about $10^{-7}$ M to about $10^{-5}$ M DDVP, to account for DDVP inactivation or inability to all hit the desired mite target AChE. In an aspect the dose of a topically applied formulation comprising DDVP as the active ingredient, may be about 0.01% to about 2% weight by volume. The lowest effective dose may also be determined in terms of mite survival time post-application. Walton et al. ("Studies in vitro on the relative efficacy of current acaricides for *Sarcoptes scabiei* var. *hominis*." Trans Royal Soc. Trop. Med. Hygiene (2000) 94:92-96) describes in vitro scabies mite kill times for various miticides, and Ditrich ("Synergestic effect between vapors of C-8514/Schering 36263 and dichlorvos against the carmine spider mite." J. Econ. Ent. 59(4): 893-896(4) (1966)) provides an LT50 for adults is 28 seconds for dichlorvos. Accordingly, an aspect of the invention is use of an organophosphate having a kill time that is better than 1 minute or better than 30 seconds, with at least half the mite population, expressed as LT50. In combination with the empirical evidence of the instant studies, this indicates that dichlorvos has an LT50 that is 120 times that of ivermectin.

Salts and Prodrugs: The invention contemplates pharmaceutically active compounds either chemically synthesized or formed by in vivo biotransformation to compounds set forth herein.

Compounds of this invention and compounds useful in the methods of this invention include those of the compounds and formula(s) described herein and pharmaceutically-acceptable salts and esters of those compounds. In embodiments, salts include any salts derived from the acids and bases of the formulas herein which are acceptable for use in human or veterinary applications. In embodiments, the term ester refers to hydrolyzable esters of compounds of the names and formulas herein. In embodiments, salts and esters of the compounds of the formulas herein can include those which have the same or better therapeutic, diagnostic, or pharmaceutical (human or veterinary) general properties as the compounds of the formulas herein. In an embodiment, a composition of the invention is a compound or salt or ester thereof suitable for pharmaceutical formulations.

Compounds of the invention and used in the methods of the invention can have prodrug forms. Prodrugs of the compounds of the invention are useful in embodiments including compositions and methods. Any compound that will be converted in vivo to provide a biologically, pharmaceutically, diagnostically, or therapeutically active form of a compound of the invention is a prodrug. Various examples and forms of prodrugs are well known in the art. Examples of prodrugs are found, inter alia, in: Design of Prodrugs, edited by H. Bundgaard, (Elsevier, 1985); Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191 (1991); H. Bundgaard, Advanced Drug Delivery Reviews, Vol. 8, p. 1-38 (1992); H. Bundgaard, et al., Journal of Pharmaceutical Sciences, Vol. 77, p. 285 (1988); and Nogrady (1985) Medicinal Chemistry A Biochemical Approach, Oxford University Press, New York, pages 388-392). A prodrug, such as a pharmaceutically acceptable prodrug, can represent prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention can be rapidly transformed in vivo to a parent compound of a compound described herein, for example, by hydrolysis in blood or by other cell, tissue, organ, or system processes. Further discussion is provided in: T. Higuchi and V. Stella, Pro-drugs as Novel Delivery Systems, V. 14 of the A.C.S. Symposium Series; and in Edward B. Roche, ed., Bioreversible Carriers in Drug Design, American Pharmaceutical Association and Pergamon Press (1987).

Active ingredients of the invention can be formulated with pharmaceutically-acceptable anions and/or cations. Pharmaceutically-acceptable cations include among others, alkali metal cations (e.g., $Li^+$, $Na^+$, $K^+$), alkaline earth metal cations (e.g., $Ca^{2+}$, $Mg^{2+}$), non-toxic heavy metal cations and ammonium ($NH_4^+$) and substituted ammonium ($N(R')_4^+$, where R' is hydrogen, alkyl, or substituted alkyl, i.e., including, methyl, ethyl, or hydroxyethyl, specifically, trimethyl ammonium, triethyl ammonium, and triethanol ammonium cations). Pharmaceutically-acceptable anions include, among others, halides (e.g., $F^-$, $Cl^-$, $Br^-$, $At^-$), sulfate, acetates (e.g., acetate, trifluoroacetate), ascorbates, aspartates, benzoates, citrates, and lactate.

Pharmaceutically acceptable salts comprise pharmaceutically-acceptable anions and/or cations. As used herein, the term "pharmaceutically acceptable salt" can refer to acid addition salts or base addition salts of the compounds in the present disclosure. A pharmaceutically acceptable salt is any salt which retains at least a portion of the activity of the parent compound and does not impart significant deleterious or undesirable effect on a subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalacturonic, propionic, salicylic, stearic, succinic, sulfamic, sulfanlic, sulfonic, sulfuric, tannic, tartaric, teoclic, toluenesulfonic, and the like. Pharmaceutically acceptable salts can be derived from amino acids, including, but not limited to, cysteine. Other pharmaceutically acceptable salts can be found, for example, in Stahl et al., Handbook of Pharmaceutical Salts: Properties, Selection, and Use, Wiley-VCH, Verlag Helvetica Chimica Acta, Zürich, 2002. (ISBN 3-906390-26-8).

5.b: Efficacy: Typically, a compound of the invention, or pharmaceutically acceptable salt thereof, is administered to a subject in a diagnostically or therapeutically effective amount.

Compositions for oral administration can be, for example, prepared in a manner such that a single dose in one or more oral preparations contains at least about 20 mg of the present compound per square meter of subject body surface area, or at least about 50, 100, 150, 200, 300, 400, or 500 mg of the present compound per square meter of subject body surface area (the average body surface area for a human is, for example, 1.8 square meters). In particular, a single dose of a composition for oral administration can contain from about 20 to about 600 mg, and in certain aspects from about 20 to about 400 mg, in another aspect from about 20 to about 300 mg, and in yet another aspect from about 20 to about 200 mg of the present compound per square meter of subject body surface area. Compositions for parenteral administration can be prepared in a manner such that a single dose contains at least about 20 mg of the present compound per square meter of subject body surface area, or at least about 40, 50, 100, 150, 200, 300, 400, or 500 mg of the present compound per square meter of subject body surface area. In particular, a single dose in one or more parenteral preparations contains from about 20 to about 500 mg, and in certain aspects from about 20 to about 400 mg, and in another aspect from about 20 to about 450 mg, and in yet another aspect from about 20 to about 350 mg of the present compound per square meter of subject body surface area. It should be recognized that these oral and parenteral dosage ranges represent generally preferred dosage ranges, and are not intended to limit the invention. The dosage regimen actually employed can vary widely, and, therefore, can deviate from the generally preferred dosage regimen. It is contemplated that one skilled in the art will tailor these ranges to the individual subject.

Toxicity and therapeutic efficacy of such compounds and bioconjugates can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds and bioconjugates that exhibit large therapeutic indices are preferred. While compounds and bioconjugates exhibiting toxic side effects can be used, care should be taken to design a delivery system that targets such compounds and bioconjugates to the site affected by the disease or disorder in order to minimize potential damage to unaffected cells and reduce side effects.

Data obtained from the cell culture assays and animal studies can be used in formulating a range of dosages for use in humans and other mammals. The dosage of such compounds and bioconjugates lies preferably within a range of circulating plasma or other bodily fluid concentrations that include the $ED_{50}$ and provides clinically efficacious results (i.e., reduction in disease symptoms). The dosage can vary within this range depending upon the dosage form employed and the route of administration utilized. For any compound and bioconjugate of the present invention, the therapeutically effective amount can be estimated initially from cell culture assays. A dosage can be formulated in animal models to achieve a circulating plasma concentration range that includes the $ED_{50}$ (the concentration of the test compound that achieves a half-maximal inhibition of symptoms) as determined in cell culture. Such information can be used to more accurately determine useful dosages in humans and other mammals. Compound and bioconjugate levels in plasma can be measured, for example, by high performance liquid chromatography.

An amount of a compound or bioconjugate that can be combined with a pharmaceutically acceptable carrier to produce a single dosage form will vary depending upon the patient treated and the particular mode of administration. It will be appreciated by those skilled in the art that the unit content of a compound/bioconjugate contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage and dosage regime for treating a disease or condition can be selected in accordance with a variety of factors, including the type, age, weight, sex, diet and/or medical condition of the patient, the route of administration, pharmacological considerations such as activity, efficacy, pharmacokinetic and/or toxicology profiles of the particular compound/bioconjugate employed, whether a compound/bioconjugate delivery system is utilized, and/or whether the compound/bioconjugate is administered as a pro-drug or part of a drug combination. Thus, the dosage regime actually employed can vary widely from subject to subject, or disease to disease and different routes of administration can be employed in different clinical settings.

The identified compounds/bioconjugates monitor, treat, inhibit, control and/or prevent, or at least partially arrest or partially prevent, diseases and conditions of interest and can be administered to a subject at therapeutically effective amounts and optionally diagnostically effective amounts. Compositions/formulations of the present invention comprise a therapeutically effective amount (which can optionally include a diagnostically effective amount) of at least one compound or bioconjugate of the present invention. Subjects receiving treatment that includes a compound/bioconjugate of the invention are preferably animals (e.g., mammals, reptiles and/or avian), more preferably humans, horses, cows, dogs, cats, sheep, pigs, and/or chickens, and most preferably humans.

5.c: Administration: The preferred composition depends on the route of administration. Any route of administration can be used as long as the target of the compound or pharmaceutically acceptable salt is available via that route. Suitable routes of administration include, for example, oral, intravenous, parenteral, inhalation, rectal, nasal, topical (e.g., transdermal and intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual, and intestinal administration.

In an embodiment, the invention provides a method for treating a medical condition comprising administering to a subject (e.g. patient) in need thereof, a therapeutically effective amount of a composition of the invention, such as an organophosphate composition. In an embodiment, the invention provides a method for diagnosing or aiding in the diagnosis of a medical condition comprising administering to a subject in need thereof, a diagnostically effective amount of a composition of the invention. In an embodiment, the medical condition is a skin condition or dermatological diseases.

The diagnostic and therapeutic formulations of this invention can be administered alone, but can be administered with a pharmaceutical carrier selected upon the basis of the chosen route of administration and standard pharmaceutical practice.

Any suitable form of administration can be employed in connection with the diagnostic and therapeutic formulations of the invention. The diagnostic and therapeutic formulations of this invention can be administered intravenously, in oral dosage forms, intraperitoneally, subcutaneously, or intramuscularly, all using dosage forms well known to those of ordinary skill in the pharmaceutical arts.

The present compositions, preparations and formulations can be formulated into diagnostic or therapeutic compositions for enteral, parenteral, topical, aerosol, inhalation, or cutaneous administration. Topical or cutaneous delivery of the compositions, preparations and formulations can also include aerosol formulation, creams, gels, solutions, etc. The present compositions, preparations and formulations are administered in doses effective to achieve the desired diagnostic and/or therapeutic effect. Such doses can vary widely depending upon the particular compositions employed in the composition, the organs or tissues to be examined, the equipment employed in the clinical procedure, the efficacy of the treatment achieved, and the like. These compositions, preparations and formulations contain an effective amount of the composition(s), along with conventional pharmaceutical carriers and excipients appropriate for the type of administration contemplated. These compositions, preparations and formulations can also optionally include stabilizing agents and skin penetration enhancing agents.

(i) Parenteral Administration: Compounds and bioconjugates of the present invention can be formulated for parenteral administration by injection (e.g., by bolus injection or continuous infusion). Formulations for injection can be presented in unit dosage form in ampoules or in multi-dose containers with an optional preservative added. The parenteral preparation can be enclosed in ampoules, disposable syringes or multiple dose vials made of glass, plastic or the like. The formulation can take such forms as suspensions, solutions or emulsions in oily or aqueous vehicles, and can contain formulatory agents such as suspending, stabilizing and/or dispersing agents.

For example, a parenteral preparation can be a sterile injectable solution or suspension in a nontoxic parenterally acceptable diluent or solvent (e.g., as a solution in 1,3-butanediol). Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid can be used in the parenteral preparation.

Alternatively, compounds and bioconjugates of the present invention can be formulated in powder form for constitution with a suitable vehicle, such as sterile pyrogen-free water, before use. For example, a compound/bioconjugate suitable for parenteral administration can include a sterile isotonic saline solution containing between 0.1 percent and 90 percent weight per volume of the compound/bioconjugate. By way of example, a solution can contain from about 5 percent to about 20 percent, more preferably from about 5 percent to about 17 percent, more preferably from about 8 to about 14 percent, and still more preferably about 10 percent weight per volume of the compound/bioconjugate. The solution or powder preparation can also include a solubilizing agent and a local anesthetic such as lignocaine to ease pain at the site of the injection. Other methods of parenteral delivery of compounds/bioconjugates will be known to the skilled artisan and are within the scope of the invention.

(ii) Oral Administration: For oral administration, a compound/bioconjugate of the invention can be formulated to take the form of tablets or capsules prepared by conventional means with one or more pharmaceutically acceptable carriers (e.g., excipients such as binding agents, fillers, lubricants and disintegrants).

(iii) Controlled-Release Administration: Controlled-release (or sustained-release) preparations can be formulated to extend the activity of a compound/bioconjugate and reduce dosage frequency. Controlled-release preparations can also be used to effect the time of onset of action or other characteristics, such as blood levels of the compound/bioconjugate, and consequently affect the occurrence of side effects.

Controlled-release preparations can be designed to initially release an amount of a compound/bioconjugate that produces the desired therapeutic effect, and gradually and continually release other amounts of the compound/bioconjugate to maintain the level of therapeutic effect over an extended period of time. In order to maintain a near-constant level of a compound/bioconjugate in the body, the compound/bioconjugate can be released from the dosage form at a rate that will replace the amount of compound/bioconjugate being metabolized and/or excreted from the body. The controlled-release of a compound/bioconjugate can be stimulated by various inducers, e.g., change in pH, change in temperature, enzymes, water, and/or other physiological conditions or molecules.

Controlled-release systems can include, for example, an infusion pump which can be used to administer the compound/bioconjugate in a manner similar to that used for delivering insulin or chemotherapy to the body generally, or to specific organs or tumors. Typically, using such a system, the compound/bioconjugate is administered in combination with a biodegradable, biocompatible polymeric implant that releases the compound/bioconjugate over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target (e.g., organ, tissue, or group of cells), thus requiring only a fraction of a systemic dosage.

Compounds/bioconjugates of the invention can be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds/bioconjugates will be known to the skilled artisan and are within the scope of the invention.

(iv) Inhalation Administration: Compounds/bioconjugates of the invention can be administered directly to the lung of a patient/subject by inhalation. For administration by inhalation, a compound/bioconjugate can be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas can be used to deliver a compound/bioconjugate directly to the lung. MDI devices are available from a number of suppliers such as 3M Corporation, Aventis, Boehringer Ingleheim, Forest Laboratories, GlaxoSmithKline, Merck & Co. and Vectura.

Alternatively, a Dry Powder Inhaler (DPI) device can be used to administer a compound/bioconjugate to the lung. DPI devices typically use a mechanism such as a burst of gas to create a cloud of dry powder inside a container, which can then be inhaled by the patient. DPI devices are also well known in the art and can be purchased from a number of vendors which include, for example, GlaxoSmithKline, Nektar Therapeutics, Innovata and Vectura. A popular variation is the multiple dose DPI ("MDDPI") system, which allows for the delivery of more than one therapeutic dose. MDDPI devices are available from companies such as AstraZeneca, GlaxoSmithKline, TEVA, Merck & Co., SkyePharma and Vectura. For example, capsules and cartridges of gelatin for use in an inhaler or insufflator can be formulated containing a powder mix of the compound/bioconjugate and a suitable powder base such as lactose or starch for these systems.

Another type of device that can be used to deliver a compound/bioconjugate to the lung is a liquid spray device supplied, for example, by Aradigm Corporation. Liquid spray systems use extremely small nozzle holes to aerosolize liquid compound/bioconjugate formulations that can then be directly inhaled into the lung. For example, a nebulizer device can be used to deliver a compound/bioconjugate to the lung. Nebulizers create aerosols from liquid compound/bioconjugate formulations by using, for example, ultrasonic energy to form fine particles that can be readily inhaled. Examples of nebulizers include devices supplied by Aventis and Battelle.

In another example, an electrohydrodynamic ("EHD") aerosol device can be used to deliver a compound/bioconjugate to the lung. EHD aerosol devices use electrical energy to aerosolize liquid compound/bioconjugate solutions or suspensions. The electrochemical properties of the compound/bioconjugate formulation are important parameters to optimize when delivering this compound/bioconjugate to the lung with an EHD aerosol device. Such optimization is routinely performed by one of skill in the art. Other methods of intra-pulmonary delivery of compounds/bioconjugates will be known to the skilled artisan and are within the scope of the invention.

Liquid compound/bioconjugate formulations suitable for use with nebulizers and liquid spray devices and EHD aerosol devices will typically include the compound/bioconjugate with a pharmaceutically acceptable carrier. In one exemplary embodiment, the pharmaceutically acceptable carrier is a liquid such as alcohol, water, polyethylene glycol or a perfluorocarbon. Optionally, another material can be added to alter the aerosol properties of the solution or suspension of the compound/bioconjugate. For example, this material can be a liquid such as an alcohol, glycol, polyglycol or a fatty acid. Other methods of formulating liquid compound/bioconjugate solutions or suspensions suitable for use in aerosol devices are known to those of skill in the art.

(v) Depot Administration: A compound/bioconjugate of the invention can be formulated as a depot preparation. Such long-acting formulations can be administered by implantation (e.g., subcutaneously or intramuscularly) or by intramuscular injection. Accordingly, the compound/bioconjugate can be formulated with suitable polymeric or hydrophobic materials such as an emulsion in an acceptable oil or ion exchange resin, or as sparingly soluble derivatives such as a sparingly soluble salt. Other methods of depot delivery of compounds/bioconjugates will be known to the skilled artisan and are within the scope of the invention.

(vi) Topical Administration: For topical application, a compound/bioconjugate can be combined with a pharmaceutically acceptable carrier so that an effective dosage is delivered, based on the desired activity ranging from an effective dosage, for example, of 0.1 µM to 20 M, and any sub-ranges thereof. In one aspect of the invention, a topical formulation of a compound/bioconjugate can be applied to the skin. The pharmaceutically acceptable carrier can be in the form of, for example, and not by way of limitation, a body wash, shampoo, ointment, cream, gel, paste, foam, aerosol, suppository, pad or gelled stick.

A topical formulation can include a therapeutically effective amount of a compound/bioconjugate in an ophthalmologically acceptable excipient such as buffered saline, mineral oil, vegetable oils such as corn or *arachis* oil, petroleum jelly, Miglyol 182, alcohol solutions, or liposomes or liposome-like products. Any of these formulations of such compounds/bioconjugates can include preservatives, antioxidants, antibiotics, immunosuppressants, and other biologically or pharmaceutically effective agents that do not exert a significant detrimental effect on the compound/bioconjugate. Other methods of topical delivery of compounds/bioconjugates will be known to the skilled artisan and are within the scope of the invention. Topical formulations of the invention further include those comprising one or more compositions useful for penetrating the skin, such as dimethyl sulfoxide (DMSO).

(vii) Rectal Administration: Compounds/bioconjugates of the invention can be formulated in rectal formulations such as suppositories or retention enemas that include conventional suppository bases such as cocoa butter or other glycerides and/or binders and/or carriers such as triglycerides, microcrystalline cellulose, gum tragacanth or gelatin. Rectal formulations can contain a compound/bioconjugate in the range of 0.5% to 10% by weight, for example. Other methods of rectal delivery of compounds/bioconjugates will be known to the skilled artisan and are within the scope of the invention.

(viii) Other Systems of Administration: Various other delivery systems are known in the art and can be used to administer the compounds/bioconjugates of the invention. Moreover, these and other delivery systems can be combined and/or modified to promote optimization of the administration of compounds/bioconjugates of the present invention. Exemplary formulations that include compounds/bioconjugates of the present invention are described elsewhere herein (the compounds/bioconjugates of the present invention are indicated as the active ingredient, but those of skill in the art will recognize that pro-drugs and compound combinations are also meant to be encompassed by this term).

5.d: Formulation: In an embodiment, the invention provides a medicament which comprises a therapeutically effective amount of one or more compositions of the invention, such as an organophosphate compound. In an embodiment, the invention provides a medicament which comprises a diagnostically effective amount of one or more compositions of the invention. In an embodiment, the invention provides a method for making a medicament for treatment of a condition described herein, such as the treatment of a skin condition or dermatological disease. In an embodiment, the invention provides a method for making a medicament for diagnosis or aiding in the diagnosis of a condition described herein, such as the diagnosis of a skin condition or dermatological disease. In an embodiment, the invention provides the use of one or more compositions set forth herein for the making of a medicament for the treatment of a skin condition or dermatological disease. In an embodiment, the invention provides the use of one or more compositions set forth herein for the treatment of a disease. In an embodiment, the invention provides the use of one or more compositions set forth herein for the diagnosis of a disease. Compositions of the invention include formulations and preparations comprising one or more of the present organophosphates provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

In an embodiment, the invention provides a pharmaceutical formulation having an active ingredient comprising a composition of the invention, such as an organophosphate compound. In an embodiment, the invention provides a method of synthesizing a composition of the invention or a pharmaceutical formulation thereof, such as an organophosphate compound. In an embodiment, a pharmaceutical formulation comprises one or more excipients, carriers, diluents, and/or other components as would be understood in the art. Preferably, the components meet the standards of the National Formulary ("NF"), United States Pharmacopoeia ("USP"; United States Pharmacopeial Convention Inc., Rockville, Md.), or Handbook of Pharmaceutical Manufacturing Formulations (Sarfaraz K. Niazi, all volumes, ISBN: 9780849317521, ISBN 10: 0849317525; CRC Press, 2004). See, e.g., United States Pharmacopeia and National Formulary (USP 30-NF 25), Rockville, Md.: United States Pharmacopeial Convention (2007 and 2008), and each of any earlier editions; The Handbook of Pharmaceutical Excipients, published jointly by the American Pharmacists Association and the Pharmaceutical Press (Pharmaceutical Press (2005) (ISBN-10: 0853696187, ISBN-13: 978-0853696186)); Merck Index, Merck & Co., Rahway, N.J.; and Gilman et al., (eds) (1996); Goodman and Gilman's: The Pharmacological Bases of Therapeutics, 8th Ed., Pergamon Press. In embodiments, the formulation base of the formulations of the invention comprises physiologically acceptable excipients, namely, at least one binder and optionally other physiologically acceptable excipients. Physiologically acceptable excipients are those known to be usable in the pharmaceutical technology sectors and adjacent areas, particularly, those listed in relevant pharmacopeias (e.g. DAB, Ph. Eur., BP, NF, USP), as well as other excipients whose properties do not impair a physiological use.

This invention also is directed, in part, to pharmaceutical compositions including a therapeutically effective amount of a compound or salt of this invention, as well as processes for making such compositions. Such compositions generally include one or more pharmaceutically acceptable carriers (e.g., excipients, vehicles, auxiliaries, adjuvants, diluents) and can include other active ingredients. Formulation of these compositions can be achieved by various methods known in the art. A general discussion of these methods can be found in, for example, Hoover, John E., Remington's Pharmaceutical Sciences (Mack Publishing Co., Easton, Pa.: 1975). See also, Lachman, L., eds., Pharmaceutical Dosage Forms (Marcel Decker, New York, N. Y., 1980).

The diagnostic and therapeutic formulations of this invention and medicaments of this invention can further comprise one or more pharmaceutically acceptable carriers, excipients, buffers, emulsifiers, surfactants, electrolytes or diluents. Such compositions and medicaments are prepared in accordance with acceptable pharmaceutical procedures, such as, for example, those described in Remingtons Pharmaceutical Sciences, 17th edition, ed. Alfonoso R. Gennaro, Mack Publishing Company, Easton, Pa. (1985).

Compositions of the invention include formulations and preparations comprising one or more of the present compounds provided in an aqueous solution, such as a pharmaceutically acceptable formulation or preparation. Optionally, compositions of the invention further comprise one or more pharmaceutically acceptable surfactants, buffers, electrolytes, salts, carriers, binders, coatings, preservatives and/or excipients.

Compounds and bioconjugates of the present invention can be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. An individual compound/bioconjugate can be administered in combination with one or more additional compounds/bioconjugates of the present invention and/or together with other biologically active or biologically inert agents. Such biologically active or inert agents can be in fluid or mechanical communication with the compound(s)/bioconjugate(s) or attached to the compound(s)/bioconjugate(s) by ionic, covalent, Van der Waals, hydrophobic, hydrophilic or other physical forces. It is preferred that administration is localized in a subject, but administration can also be systemic.

Compounds and bioconjugates of the present invention can be formulated by any conventional manner using one or more pharmaceutically acceptable carriers. Thus, the compound(s)/bioconjugate(s) and their pharmaceutically acceptable salts and solvates can be specifically formulated for administration, e.g., by inhalation or insufflation (either through the mouth or the nose) or oral, buccal, parenteral or rectal administration. The compounds/bioconjugates can take the form of charged, neutral and/or other pharmaceutically acceptable salt forms. Examples of pharmaceutically acceptable carriers include, but are not limited to, those described in REMINGTON'S PHARMACEUTICAL SCIENCES (A.R. Gennaro, Ed.), 20th edition, Williams & Wilkins Pa., USA (2000).

Compounds and bioconjugates of the present invention can be formulated in the form of solutions, suspensions, emulsions, tablets, pills, capsules, powders, controlled- or sustained-release formulations and the like. Such formulations will contain a therapeutically effective amount of the compound/bioconjugate, preferably in purified form, together with a suitable amount of carrier so as to provide the form for proper administration to the patient. The formulation should suit the mode of administration.

Pharmaceutically acceptable carriers that can be used in conjunction with the compounds of the invention are well known to those of ordinary skill in the art. Carriers can be selected based on a number of factors including, for example, the particular compound(s) or pharmaceutically acceptable salt(s) used; the compound's concentration, stability, and intended bioavailability; the condition being treated; the subject's age, size, and general condition; the route of administration; etc. A general discussion related to carriers can be found in, for example, J. G. Nairn, Remington's Pharmaceutical Science, pp. 1492-1517 (A. Gennaro, ed., Mack Publishing Co., Easton, Pa. (1985)).

Solid dosage forms for oral administration include, for example, capsules, tablets, gel-caps, pills, dragees, troches, powders, granules, and lozenges. In such solid dosage forms, the compounds or pharmaceutically acceptable salts thereof can be combined with one or more pharmaceutically acceptable carriers. The compounds and pharmaceutically acceptable salts thereof can be mixed with carriers including, but not limited to, lactose, sucrose, starch powder, corn starch, potato starch, magnesium carbonate, microcrystalline cellulose, cellulose esters of alkanoic acids, cellulose alkyl esters, talc, stearic acid, magnesium stearate, magnesium oxide, sodium and calcium salts of phosphoric and sulfuric acids, sodium carbonate, agar, mannitol, sorbitol, sodium saccharin, gelatin, *acacia* gum, alginic acid, sodium alginate, tragacanth, colloidal silicon dioxide, croscarmellose sodium, polyvinylpyrrolidone, and/or polyvinyl alcohol, and then tableted or encapsulated for convenient administration. Such capsules or tablets can contain a controlled-release formulation, as can be provided in a dispersion of the compound or salt in hydroxypropylmethyl cellulose. In the case of capsules, tablets, and pills, the dosage forms also can include buffering agents, such as sodium citrate, or magnesium or calcium carbonate or bicarbonate. Tablets and pills additionally can, for example, include a coating (e.g., an enteric coating) to delay disintegration and absorption. The concentration of the present compounds in a solid oral dosage form can be from about 5 to about 50% for example, and in certain aspects from about 8 to about 40%, and in another aspect from about 10 to about 30% by weight based on the total weight of the composition.

Liquid dosage forms of the compounds of the invention for oral administration include, for example, pharmaceutically acceptable emulsions, solutions, suspensions, syrups, and elixirs containing inert diluents commonly used in the art (e.g., water). Such compositions also can include adjuvants, such as wetting, emulsifying, suspending, flavoring (e.g., sweetening), and/or perfuming agents. The concentration of the present compounds in the liquid dosage form can be from about 0.01 to about 5 mg, and in certain aspects from about 0.01 to about 1 mg, and in another aspect from about 0.01 to about 0.5 mg per ml of the composition. Low concentrations of the compounds of the invention in liquid dosage form can be prepared in the case that the compound is more soluble at low concentrations. Techniques for making oral dosage forms useful in the invention are generally described in, for example, Modern Pharmaceutics, Chapters 9 and 10 (Banker & Rhodes, Editors (1979)). See also, Lieberman et al., Pharmaceutical Dosage Forms: Tablets (1981). See also, Ansel, Introduction to Pharmaceutical Dosage Forms (2nd Edition (1976)).

In some aspects of the invention, tablets or powders for oral administration can be prepared by dissolving the compound in a pharmaceutically acceptable solvent capable of dissolving the compound to form a solution and then evaporating when the solution is dried under vacuum. A carrier can also be added to the solution before drying. The resulting solution can be dried under vacuum to form a glass. The glass can then be mixed with a binder to form a powder. This powder can be mixed with fillers or other conventional tableting agents, and then processed to form a tablet. Alternatively, the powder can be added to a liquid carrier to form a solution, emulsion, suspension, or the like.

In some aspects, solutions for oral administration are prepared by dissolving the compound in a pharmaceutically acceptable solvent capable of dissolving the compound to form a solution. An appropriate volume of a carrier is added to the solution while stirring to form a pharmaceutically acceptable solution for oral administration.

In some embodiments, a liposome or micelle can be utilized as a carrier or vehicle for the composition. For example, in some embodiments, the compound can be a part of the lipophilic bilayers or micelle, and the targeting ligand, if present, can be on the external surface of the liposome or micelle. As another example, a targeting ligand can be externally attached to the liposome or micelle after formulation for targeting the liposome or micelle (which contains the organophosphate agents) to the desired tissue, organ, or other site in the body.

Injectable preparations (e.g., sterile injectable aqueous or oleaginous suspensions) can be formulated according to the known art using suitable dispersing, wetting agents, and/or suspending agents. Acceptable vehicles for parenteral use include both aqueous and nonaqueous pharmaceutically-acceptable solvents. Suitable pharmaceutically acceptable aqueous solvents include, for example, water, saline solutions, dextrose solutions (such as DW5), electrolyte solutions, etc.

In one embodiment, the present compounds are formulated as nanoparticles or microparticles. Use of such nanoparticle or microparticle formulations can be beneficial for some applications to enhance delivery, localization, target specificity, administration, etc. of the compound. Potentially useful nanoparticles and microparticles include, but are not limited to, micelles, liposomes, microemulsions, nanoemulsions, vesicles, tubular micelles, cylindrical micelles, bilayers, folded sheets structures, globular aggregates, swollen micelles, inclusion complex, encapsulated droplets, microcapsules, nanocapsules or the like. As will be understood by those having skill in the art, the present compounds can be located inside the nanoparticle or microparticle, within a membrane or wall of the nanoparticle or microparticle, or outside of (but bonded to or otherwise associated with) the nanoparticle or microparticle. The agent formulated in nanoparticles or microparticles can be administered by any of the routes previously described. In a formulation applied topically, the compound is slowly released over time. In an injectable formulation, the liposome, micelle, capsule, etc., circulates in the bloodstream and is delivered to the desired site (e.g., target tissue).

Preparation and loading of nanoparticles and microparticles are well known in the art. As one example, liposomes can be prepared from dipalmitoyl phosphatidylcholine (DPPC) or egg phosphatidylcholine (PC) because this lipid has a low heat transition. Liposomes are made using standard procedures as known to one skilled in the art (e.g., Braun-Falco et al., (Eds.), Griesbach Conference, Liposome Dermatics, Springer-Verlag, Berlin (1992), pp. 69 81; 91 117. Polycaprolactone, poly(glycolic) acid, poly(lactic) acid, polyanhydride or lipids can be formulated as microspheres. As an illustrative example, the present compounds can be mixed with polyvinyl alcohol (PVA), the mixture then dried and coated with ethylene vinyl acetate, then cooled again with PVA. In a liposome, the present compounds can be within one or both lipid bilayers, in the aqueous between the bilayers, or within the center or core. Liposomes can be modified with other molecules and lipids to form a cationic liposome. Liposomes can also be modified with lipids to render their surface more hydrophilic which increases their circulation time in the bloodstream. The thus-modified liposome has been termed a "stealth" liposome, or a long-lived liposome, as described in U.S. Pat. No. 6,258,378, and in Stealth Liposomes, Lasic and Martin (Eds.) 1995 CRC Press, London. Encapsulation methods include detergent dialysis, freeze drying, film forming, injection, as known to one skilled in the art and disclosed in, for example, U.S. Pat. No. 6,406,713. Optionally, the present compositions and methods include a micelle delivery system, for example, involving one or more PEG-based amphiphilic polymers developed for drug delivery including: PEG-poly(ε-caprolactone), PEG-poly(amino acid), PEG-polylactide or PEG-phospholipid constructs; a cross linked poly(acrylic acid) polymer system, a phospholipid-based system and/or block copolymer systems comprising one or more of the following polymer blocks: a poly(lactic acid) polymer block; a poly(propylene glycol) polymer block; a poly(amino acid) polymer block; a poly(ester) polymer block; a poly (ε-caprolactone) polymer block; a poly(ethylene glycol) block, a poly(acrylic acid) block; a polylactide block; a polyester block; a polyamide block; a polyanhydride block; a polyurethane block; a polyimine block; a polyurea block; a polyacetal block; a polysaccharide block; and a polysiloxane block.

Suitable pharmaceutically-acceptable nonaqueous solvents include, but are not limited to, the following (as well as mixtures thereof):

(i) Alcohols (these include, for example, σ-glycerol formal, δ-glycerol formal, 1,3-butyleneglycol, aliphatic or aromatic alcohols having from 2 to about 30 carbons (e.g., methanol, ethanol, propanol, isopropanol, butanol, t-butanol, hexanol, octanol, amylene hydrate, benzyl alcohol, glycerin (glycerol), glycol, hexylene, glycol, tetrahydrofuranyl alcohol, cetyl alcohol, and stearyl alcohol), fatty acid esters of fatty alcohols (e.g., polyalkylene glycols, such as polypropylene glycol and polyethylene glycol), sorbitan, sucrose, and cholesterol);

(ii) Amides, which include, for example, dimethylacetamide (DMA), benzyl benzoate DMA, dimethylformamide, N-hydroxyethyO-lactamide, N, N-di methylacetamideamides, 2-pyrrolidinone, 1-methyl-2-pyrrolidinone, and polyvinylpyrrolidone;

(iii) Esters, which include, for example, acetate esters (e.g., monoacetin, diacetin, and triacetin), aliphatic and aromatic esters (e.g., ethyl caprylate or octanoate, alkyl oleate, benzyl benzoate, or benzyl acetate), dimethylsulfoxide (DMSO), esters of glycerin (e.g., mono, di, and triglyceryl citrates and tartrates), ethyl benzoate, ethyl acetate, ethyl carbonate, ethyl lactate, ethyl oleate, fatty acid esters of sorbitan, glyceryl monostearate, glyceride esters (e.g., mono, di, or tri-glycerides), fatty acid esters (e.g., isopropyl myristrate), fatty acid derived PEG esters (e.g., PEG-hydroxyoleate and PEG-hydroxystearate), N-methyl pyrrolidinone, pluronic 60, polyoxyethylene sorbitol oleic polyesters (e.g., poly(ethoxylated)$_{30-60}$ sorbitol poly(oleate)$_{2-4}$, poly (oxyethylene)$_{15-20}$ monooleate, poly(oxyethylene)$_{15-20}$ mono 12-hydroxystearate, and poly(oxyethylene)$_{15-20}$ mono ricinoleate), polyoxyethylene sorbitan esters (e.g., polyoxyethylene-sorbitan monooleate, polyoxyethylene-sorbitan monopalmitate, polyoxyethylene-sorbitan monolaurate, polyoxyethylene-sorbitan monostearate, and POLYSORBATE 20, 40, 60, and 80 (from ICI Americas, Wilmington, Del.)), polyvinylpyrrolidone, alkyleneoxy modified fatty acid esters (e.g., polyoxyl 40 hydrogenated castor oil and polyoxyethylated castor oils, such as CREMOPHOR EL solution or CREMOPHOR RH 40 solution), saccharide fatty acid esters (i.e., the condensation product of a monosaccharide (e.g., pentoses, such as, ribose, ribulose, arabinose, xylose, lyxose, and xylulose; hexoses, such as glucose, fructose, galactose, mannose, and sorbose; trioses; tetroses; heptoses; and octoses), disaccharide (e.g., sucrose, maltose, lactose, and trehalose), oligosaccharide, or a mixture thereof with one or more $C_4$-$C_{22}$ fatty acids (e.g., saturated fatty acids, such as caprylic acid, capric acid, lauric acid, myristic acid, palmitic acid, and stearic acid; and unsaturated fatty acids, such as palmitoleic acid, oleic acid, elaidic acid, erucic acid, and linoleic acid), and steroidal esters;

(iv) Ethers, for example, alkyl, aryl, and cyclic ethers having from 2 to about 30 carbons. Examples include diethyl ether, tetrahydrofuran, di methyl isosorbide, diethylene glycol monoethyl ether), and glycofurol (tetrahydrofurfuranyl alcohol polyethylene glycol ether);

(v) Ketones which typically have from about 3 to about 30 carbons. Examples include acetone, methyl ethyl ketone, and methyl isobutyl ketone;

(vi) Hydrocarbons which are typically aliphatic, cycloaliphatic, or aromatic hydrocarbons having from about 4 to about 30 carbons. Examples include benzene, cyclohexane, dichloromethane, dioxolanes, hexane, n-decane, n-dodecane, n-hexane, sulfolane, tetramethylenesulfone, tetramethylenesulfoxide, toluene, di methylsulfoxide (DMSO); and tetramethylene sulfoxide;

(vii) Oils which include, for example, oils of mineral, vegetable, animal, essential, or synthetic origin. These include: mineral oils, such as aliphatic and wax-based hydrocarbons, aromatic hydrocarbons, mixed aliphatic and aromatic based hydrocarbons, and refined paraffin oil; vegetable oils, such as linseed, tung, safflower, soybean, castor, cottonseed, groundnut, rapeseed, coconut, palm, olive, corn, corn germ, sesame, persic, and peanut oil; glycerides, such as mono-, di-, and triglycerides; animal oils, such as fish, marine, sperm, cod-liver, haliver, squalene, squalane, and shark liver oil; oleic oils; and polyoxyethylated castor oil;

(viii) Alkyl, alkenyl, or aryl halides which include, for example, alkyl or aryl halides having from 1 to about 30 carbons and one or more halogen substituents. Examples include: methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (SOLUTOL HS-15, from BASF, Ludwigshafen, Germany); polyoxyethylene glycerol; sodium laurate; sodium oleate; and sorbitan monooleate.

Other pharmaceutically acceptable solvents for use in the invention are well known to those of ordinary skill in the art. General discussion relating to such solvents can be found in, for example, The Chemotherapy Source Book (Williams & Wilkens Publishing), The Handbook of Pharmaceutical Excipients, (American Pharmaceutical Association, Washington, D.C., and The Pharmaceutical Society of Great Britain, London, England, 1968), Modern Pharmaceutics 3d ed., (G. Banker et. al., eds., Marcel Dekker, Inc., New York, N.Y. (1995)), The Pharmacological Basis of Therapeutics, (Goodman & Gilman, McGraw Hill Publishing), Pharmaceutical Dosage Forms, (H. Lieberman et. al., eds., Marcel Dekker, Inc., New York, N.Y. (1980)), Remington's Pharmaceutical Sciences, 19th ed., (A. Gennaro, ed., Mack Publishing, Easton, Pa., (1995)), The United States Pharmacopeia 24, The National Formulary 19, (National Publishing, Philadelphia, Pa. (2000)); Spiegel, A. J., et al., "Use of Nonaqueous Solvents in Parenteral Products," J. Pharma. Sciences, Vol. 52, No. 10, pp. 917-927 (1963).

Solvents useful in the invention include, but are not limited to, those known to stabilize present compounds or pharmaceutically acceptable salts thereof. These can include, for example, oils rich in triglycerides, such as safflower oil, soybean oil, and mixtures thereof; and alkyleneoxy-modified fatty acid esters, such as polyoxyl 40 hydrogenated castor oil and polyoxyethylated castor oils (e.g., CREMOPHOR EL solution or CREMOPHOR RH 40 solution). Commercially available triglycerides include INTRALIPID emulsified soybean oil (Kabi-Pharmacia Inc., Stockholm, Sweden), NUTRALIPID emulsion (McGaw, Irvine, Calif.), LIPOSYN II 20% emulsion (a 20% fat emulsion solution containing 100 mg safflower oil, 100 mg soybean oil, 12 mg egg phosphatides, and 25 mg glycerin per ml of solution; Abbott Laboratories, Chicago, Ill.), LIPOSYN III 2% emulsion (a 2% fat emulsion solution containing 100 mg safflower oil, 100 mg soybean oil, 12 mg egg phosphatides, and 25 mg glycerin per ml of solution; Abbott Laboratories, Chicago, Ill.), natural or synthetic glycerol derivatives containing the docosahexaenoyl group at levels of from about 25 to about 100% (by weight based on the total fatty acid content) (DHASCO from Martek Biosciences Corp., Columbia, Md.; DHA MAGURO from Daito Enterprises, Los Angeles, Calif.; SOYACAL; and TRAVEMULSION). Ethanol in particular is a useful solvent for dissolving a compound or pharmaceutically acceptable salt thereof to form solutions, emulsions, and the like.

Additional components can be included in the compositions of this invention for various purposes generally known in the pharmaceutical industry. These components tend to impart properties that, for example, enhance retention of the present compounds or salt thereof at the site of administration, protect the stability of the composition, control the pH, and facilitate processing of the compound or salt thereof into pharmaceutical formulations, and the like. Specific examples of such components include cryoprotective agents; agents for preventing reprecipitation of the compound or salt surface; active, wetting, or emulsifying agents (e.g., lecithin, polysorbate-80, TWEEN 80, pluronic 60, and polyoxyethylene stearate); preservatives (e.g., ethyl-p-hydroxybenzoate); microbial preservatives (e.g., benzyl alcohol, phenol, m-cresol, chlorobutanol, sorbic acid, thimerosal, and paraben); agents for adjusting pH or buffering agents (e.g., acids, bases, sodium acetate, sorbitan monolaurate, etc.); agents for adjusting osmolarity (e.g., glycerin); thickeners (e.g., aluminum monostearate, stearic acid, cetyl alcohol, stearyl alcohol, guar gum, methyl cellulose, hydroxypropylcellulose, tristearin, cetyl wax esters, polyethylene glycol, etc.); colorants; dyes; flow aids; non-volatile silicones (e.g., cyclomethicone); clays (e.g., bentonites); adhesives; bulking agents; flavorings; sweeteners; adsorbents; fillers (e.g., sugars such as lactose, sucrose, mannitol, sorbitol, cellulose, calcium phosphate, etc.); diluents (e.g., water, saline, electrolyte solutions, etc.); binders (e.g., gelatin; gum tragacanth; methyl cellulose; hydroxypropyl methylcellulose; sodium carboxymethyl cellulose; polyvinylpyrrolidone; sugars; polymers; *acacia*; starches, such as maize starch, wheat starch, rice starch, and potato starch; etc.); disintegrating agents (e.g., starches, such as maize starch, wheat starch, rice starch, potato starch, and carboxymethyl starch; cross-linked polyvinyl pyrrolidone; agar; alginic acid or a salt thereof, such as sodium alginate; croscarmellose sodium; crospovidone; etc); lubricants (e.g., silica; talc; stearic acid and salts thereof, such as magnesium stearate; polyethylene glycol; etc.); coating agents (e.g., concentrated sugar solutions including gum arabic, talc, polyvinyl pyrrolidone, carbopol gel, polyethylene glycol, titanium dioxide, etc.); and antioxidants (e.g., sodium metabisulfite, sodium bisulfite, sodium sulfite, dextrose, phenols, thiophenols, etc.).

Techniques and compositions for making parenteral dosage forms are generally known in the art. Formulations for parenteral administration can be prepared from one or more sterile powders and/or granules having a compound or salt of this invention and one or more of the carriers or diluents mentioned for use in the formulations for oral administration. The powder or granule typically is added to an appropriate volume of a solvent (typically while agitating (e.g., stirring) the solvent) that is capable of dissolving the powder or granule. Particular solvents useful in the invention include, for example, water, polyethylene glycol, propylene glycol, ethanol, corn oil, cottonseed oil, peanut oil, sesame oil, benzyl alcohol, sodium chloride, and/or various buffers.

Emulsions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the emulsion. Solutions for parenteral administration can be prepared by, for example, dissolving a compound or salt of this invention in any pharmaceutically acceptable solvent capable of dissolving the compound to form a solution; and adding an appropriate volume of a carrier to the solution while stirring to form the solution.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, cocoa butter; synthetic mono-, di-, or triglycerides; fatty acids; and/or polyethylene glycols.

Every formulation or combination of components described or exemplified herein can be used to practice the invention, unless otherwise stated.

(i) Binding Agents: Binding agents include, but are not limited to, corn starch, potato starch, or other starches, gelatin, natural and synthetic gums such as *acacia*, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

(ii) Fillers: Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

(iii) Lubricants: Lubricants include, but are not limited to, calcium stearate, magnesium stearate, mineral oil, electromagnetic radiation mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

(iv) Disintegrants: Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Tablets or capsules can optionally be coated by methods well known in the art. If binders and/or fillers are used with a compound/bioconjugate of the invention, they are typically formulated as about 50 to about 99 weight percent of the compound/bioconjugate. In one aspect, about 0.5 to about 15 weight percent of disintegrant, and particularly about 1 to about 5 weight percent of disintegrant, can be used in combination with the compound. A lubricant can optionally be added, typically in an amount of less than about 1 weight percent of the compound/bioconjugate. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other formulations are known in the art.

Liquid preparations for oral administration can take the form of solutions, syrups or suspensions. Alternatively, the liquid preparations can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or *acacia*); non-aqueous vehicles (e.g., almond oil, oily esters, ethyl alcohol or fractionated vegetable oils); and/or preservatives (e.g., methyl or propyl-p-hydroxybenzoates or sorbic acid). The preparations can also contain buffer salts, flavoring, coloring, perfuming and sweetening agents as appropriate. Preparations for oral administration can also be formulated to achieve controlled release of the compound/bioconjugate. Oral formulations preferably contain 10% to 95% compound/bioconjugate. In addition, a compound/bioconjugate of the present invention can be formulated for buccal administration in the form of tablets or lozenges formulated in a conventional manner. Other methods of oral delivery of compounds/bioconjugates of the invention will be known to the skilled artisan and are within the scope of the invention.

Formulation 1 Hard gelatin capsules are prepared using the ingredients of Table F1. The ingredients of Table F1 are mixed and filled into hard gelatin capsules in 560 mg quantities.

Formulation 2: A tablet formula is prepared using the ingredients of Table F2. The components are blended and compressed to form tablets, each weighing 665 mg.

Formulation 3: A dry powder inhaler formulation is prepared containing the components of Table F3. The active ingredient is mixed with the lactose and the mixture is added to a dry powder inhaling appliance.

Formulation 4: Tablets, each containing 60 mg of active ingredient, are prepared as outlined in Table F4. The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5: Capsules, each containing 80 mg of active ingredient are made as indicated in Table F5. The active ingredient, cellulose, starch, and magnesium stearate are blended, passed through a No. 20 mesh U.S. sieve, and filled into hard gelatin capsules in 190 mg quantities.

Formulation 6: Suppositories, each containing 225 mg of active ingredient, are made as shown in Table F6. The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7 Suspensions, each containing 50 mg of active ingredient per 5.0 ml dose are made as shown in Table F7. The active ingredient, sucrose and xantham gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8: Capsules, each containing 150 mg of active ingredient, are made as shown in Table F8. The active ingredient, cellulose, starch, and magnesium stearate are blended, passed through a No. 20 mesh U.S. sieve, and filled into hard gelatin capsules in 560 mg quantities.

4.e: Kits: Various embodiments of the present invention include kits. Such kits can include a compound/bioconjugate of the present invention, optionally one or more ingredients for preparing a pharmaceutically acceptable formulation of the compound/bioconjugate, and instructions for use (e.g., administration). When supplied as a kit, different components of a compound/bioconjugate formulation can be packaged in separate containers and admixed immediately before use. Such packaging of the components separately can, if desired, be presented in a pack or dispenser device which can contain one or more unit dosage forms containing the compound/bioconjugate. The pack can, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

It is further contemplated that the compounds and salts of this invention can be used in the form of a kit that is suitable for use in performing the methods described herein, packaged in a container. The kit can contain the compound or compounds and, optionally, appropriate diluents, devices or device components suitable for administration and instructions for use in accordance with the methods of the invention. The devices can include parenteral injection devices, such as syringes or transdermal patch or the like. Device components can include cartridges for use in injection devices and the like. In one aspect, the kit includes a first dosage form including a compound or salt of this invention and a second dosage form including another active ingredient in quantities sufficient to carry out the methods of the invention. The first dosage form and the second dosage form together can include a therapeutically effective amount of the compounds for treating the targeted condition(s).

In certain embodiments, kits can be supplied with instructional materials. Instructions can be printed on paper or other substrate, and/or can be supplied as an electronic-readable medium, such as a floppy disc, mini-CD-ROM, CD-ROM, DVD-ROM, Zip disc, videotape, audio tape, and the like. Detailed instructions cannot be physically associated with the kit; instead, a user can be directed to an Internet web site specified by the manufacturer or distributor of the kit, or supplied as electronic mail.

If desired, the emulsions or solutions described above for oral or parenteral administration can be packaged in IV bags, vials, or other conventional containers in concentrated form, and then diluted with a pharmaceutically acceptable liquid (e.g., saline) to form an acceptable compound concentration before use.

Kits can include reagents in separate containers such as, for example, sterile water or saline to be added to a lyophilized active component packaged separately. For example, sealed glass ampules can contain lyophilized superoxide dismutase mimetics and in a separate ampule, sterile water, sterile saline or sterile each of which has been packaged under a neutral non-reacting gas, such as nitrogen. Ampules can consist of any suitable material, such as glass, organic polymers, such as polycarbonate, polystyrene, ceramic, metal or any other material typically employed to hold reagents. Other examples of suitable containers include bottles that can be fabricated from similar substances as ampules, and envelopes that can consist of foil-lined interiors, such as aluminum or an alloy. Other containers include test tubes, vials, flasks, bottles, syringes, and the like. Containers can have a sterile access port, such as a bottle having a stopper that can be pierced by a hypodermic injection needle. Other containers can have two compartments that are separated by a readily removable membrane that upon removal permits the components to mix. Removable membranes can be glass, plastic, rubber, and the like.

Example 7: Treatment of Acne *Vulgaris*

Any of the methods of treating provided herein may be used to treat acne *vulgaris*. This is example is based in part on a recognition that acne *vulgaris* appears associated with *demodex* mites. See, e.g., Zhao et al. J. Zhejiang Univ-Sci B (Biomed & Biotechnol. 2012 13(3):192-202. Accordingly, any of the compounds and compositions described herein that kill demodex mites may be used in a method of treating acne *vulgaris*.

Example 8

Diagnostic tests for skin affliction caused by Demodix mites. Interestingly, initial treatment applications with an organophosphate results in an observable flare-up response in certain applied areas. After initial treatment, not observable flare-up occurs. Similarly, patients that do not have the skin affliction do not have an observable flare-up response after organophosphate application. A reason for these results is that patients that do not have a Demodix mite infestation, or that are not sensitized to a bacteria carried by the Demodix mites, do not have an initial adverse response to organophosphate treatment. This difference in response to organophosphate may be employed as a tool to diagnose a skin affliction. For example, a skin affliction that is rosacea may be diagnosed by initial short-term application of an organophosphate. If there is an observable flare-up response, such as substantial flushing, redness, bloating, discoloration, itching or other irritation, a diagnosis of a mite-related skin affliction, such as rosacea, may be made. Alternatively, if there is no observable flare-up response, a negative diagnosis may be made. The application can be by any reliable means to the skin, similar to a skin allergy test. The organophosphate may be applied to a surface of an application substrate having an adhesive side that supports the active agent that is applied to the skin for an application time, such as an application time that is greater than 10 seconds and less than about 5 minutes. The application substrate is removed and the skin observed for a flare-up response. A positive flare-up response indicates the presence of a skin affliction, including presence of mites that are susceptible to the organophosphate. In contrast, if no flare-up response is observed, the patient is characterized as not having the skin affliction and/or not having the mites that are susceptible to the organophosphate. Other types of application steps are compatible in the diagnostic methods of the instant invention, including swabbing, or self-application. The diagnostic test may further comprise the step of rinsing the skin to remove the organophosphate prior to the observation step. Controls may be used, with an identical application except without the organophosphate to control for other allergic responses associated with the diagnostic test (e.g., latex and/or adhesive sensitivity). The application area may be selected to be a localized area, such as less than about 100 $cm^2$, less than 10 $cm^2$, or less than 1 $cm^2$. Preferably, the area corresponds to regions where the mites tend to favor, including certain facial areas.

For patients having an observable flare-up response, the patient may then be treated with a full course of organophosphate treatment. For patients not having an observable flare-up response, a treatment that is not an organophosphate treatment may be indicated.

Statements Regarding Incorporation by Reference and Variations

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and method steps set forth in the present description. As will be obvious to one of skill in the art, methods and devices useful for the present methods can include a large number of optional composition and processing elements and steps.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

TABLES

TABLE 1

Oral antibiotics:

| Generic Name | Brand Name |
|---|---|
| doxycycline | Doryx, Oracea, Vibramycin |
| erythromycin | Akne-mycin |
| minocycline | Minocin |
| tetracycline | Sumycin |
| trimethoprim-sulfamethoxazole | Bactrim, Septra |

TABLE 2

Topical antibiotics

| Generic Name | Brand Name |
|---|---|
| Metronidazole | MetroCream, MetroGel, Noritate |

TABLE 3

Drugs prescribed by dermatologists for the treatment of rosacea.

| | | |
|---|---|---|
| doxycycline hyclate Oral | Off Label | RX |
| doxycycline calcium Oral | Off Label | RX |
| Doryx Oral | Off Label | RX |
| Metrogel Top | On Label | RX |
| Finacea Top | On Label | RX |
| tetracycline Oral | Off Label | RX |
| clindamycin phosphate Top | Off Label | RX |
| Vibramycin Oral | Off Label | RX |
| Adoxa Oral | Off Label | RX |
| PRASCION Top | Off Label | RX |
| doxycycline monohydrate Oral | Off Label | RX |
| Monodox Oral | Off Label | RX |
| Sumaxin Top | Off Label | RX |
| Clarifoam EF Top | Off Label | RX |
| Cleocin T Top | Off Label | RX |
| Evoclin Top | Off Label | RX |
| metronidazole Top | On Label | RX |
| Avar-E Top | Off Label | RX |
| Noritate Top | On Label | RX |
| Clindagel Top | Off Label | RX |
| sulfacetamide sodium-sulfur Top | Off Label | RX |
| PRASCION FC Top | Off Label | RX |
| azelaic acid Top | On Label | RX |
| MetroCream Top | On Label | RX |
| Avar Top | Off Label | RX |
| Avar-E LS Top | Off Label | RX |
| Avar-E Green Top | Off Label | RX |
| SE 10-5 SS Top | Off Label | RX |
| Sumadan Top | Off Label | RX |
| Claris Clarifying Wash Top | Off Label | RX |
| BP 10-1 Top | Off Label | RX |
| Sumaxin TS Top | Off Label | RX |
| Clindacin P Top | Off Label | RX |
| clindamycin phos-skin clnsr 19 Top | On Label | RX |
| Clindacin Pac Top | On Label | RX |
| Rosanil Top | On Label | RX |
| sulfacetamide sod-sulfur-urea Top | Off Label | RX |
| Cleansing Wash Top | Off Label | OTC/RX |
| sulfacet sod-sulfur-witch haz Top | Off Label | RX |
| Avidoxy Oral | Off Label | RX |
| Cerisa Top | Off Label | RX |
| Avar LS Top | Off Label | RX |
| Zencia Top | Off Label | RX |
| Morgidox Oral | Off Label | RX |
| SulfaCleanse 8-4 Top | Off Label | RX |
| SSS 10-4 Top | Off Label | RX |
| sulfacetamide-sulfur-cleansr23 Top | Off Label | RX |
| Sumaxin CP Top | Off Label | RX |
| Virti-Sulf Top | Off Label | RX |
| SSS 10-5 Top | Off Label | RX |
| sulfacetamide-sulfur-cleansr32 Top | Off Label | RX |
| Clindacin ETZ Top | Off Label | RX |
| MetroLotion Top | Off Label | RX |
| Rosadan Top | Off Label | RX |
| metronidazole-skin cleansr #23 Top | Off Label | RX |

TABLE F1

| Ingredients | (mg/capsule) |
|---|---|
| Active Ingredient | 250.0 |
| Starch | 305.0 |
| Magnesium stearate | 5.0 |

TABLE F2

| Ingredients | (mg/tablet) |
|---|---|
| Active Ingredient | 250.0 |
| Cellulose, microcrystalline | 400.0 |
| Colloidal silicon dioxide | 10.0 |
| Stearic acid | 5.0 |

TABLE F3

| Ingredients | Weight % |
|---|---|
| Active ingredient | 5 |
| Lactose | 95 |

TABLE F4

| Ingredients | Milligrams |
|---|---|
| Active ingredient | 60.0 |
| Starch | 45.0 |
| Microcrystalline cellulose | 35.0 |
| Polyvinylpyrrolidone (as 10% solution in water) | 4.0 |

TABLE F4-continued

| Ingredients | Milligrams |
| --- | --- |
| Sodium carboxymethyl starch | 4.5 |
| Magnesium stearate | 0.5 |
| Talc | 1.0 |
| Total | 150.0 |

TABLE F5

| Ingredients | Milligrams |
| --- | --- |
| Active ingredient | 80.0 |
| Starch | 109.0 |
| Magnesium stearate | 1.0 |
| Total | 190.0 |

TABLE F6

| Ingredients | Milligrams |
| --- | --- |
| Active Ingredient | 225 |
| Saturated fatty acid glycerides to | 2000 |

TABLE F7

| Ingredients | Milligrams |
| --- | --- |
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

TABLE F8

| Ingredients | Milligrams |
| --- | --- |
| Active ingredient | 150.0 |
| Starch | 407.0 |
| Magnesium stearate | 3.0 |
| Total | 560.0 |

TABLE OF REFERENCES

[1] Nat'l Rosacea Soc.: www.rosacea.org/patients/allaboutrosacea.php

[2] Kligman A M & Christensen M S. (2011) *Demodex folliculorum*: Requirements for Understanding Its Role in Human Skin Disease. *Journal of Investigative Dermatology.* 131: 8-10

[3] Despommier, D, Gwadz R W, Hotez P J and Knirsch C A. Parasitic Diseases. 5th ed. New York: Apple Trees Production, LLC. 2006

[4] Hsu C K, Hsu M M, Lee J Y. (2009) Demodicosis: a clinicopathological study. *J Am Acad Dermatol.* 60(3): 453-62

[5] Lacey N, Kavanagh K, Tseng S C. (2009) Under the lash: *Demodex* mites in human diseases. *Biochem (Lond).* 31(4): 2-6

[6] Liva J, Sheha H, & Tsenga S C G. (2010) Pathogenic role of *Demodex* mites in blepharitis. *Curr Opin Allergy Clin Immunol.* 10(5): 505-510.

[7] Thomson, W. T. 1976. Agricultural chemicals—book 1: insecticides, acaricides, and ovicides. Revised ed. Thomson Publ., Indianapolis, Ind. 232 pp.

[8] The Pesticide Manual: A World Compendium, 7th ed. 1983. C.R. Worthing, ed. The British Crop Protection Council, Croydon, England. 695 pp.

[9] U. S. Department of Health and Human Services, National Institute for Occupational Safety and Health. 1981. Occupational health guidelines for chemical hazards. F. W. Mackinson, R. S. Stricoff, L. J. Partridge, Jr., and A. D. Little, Inc., eds. DHHS (NIOSH) Publ. No. 81-123. Washington, DC.

[10]. American Conference of Governmental Industrial Hygienists. 1984. TLVs: threshold limit values for chemical substances and physical agents in the work environment and biological exposure indices with intended changes for 1984-85. Cincinnati, Ohio 116 pp.

[11] Farm Chemicals Handbook, 70th ed. 1984. R. T. Meister, G. L. Berg, C. Sine, S. Meister, and J. Poplyk, eds. Meister Publishing Co., Willoughby, Ohio.

[12] *Demodex* mites: Facts and controversies. Elston D M. Department of Dermatology, Geisinger Medical Center, 100 N Academy Ave, Danville, Danville, Pa. 17822-5206, USA. Clin Dermatol. 2010 September-October; 28(5): 502-504.

[13] For a partial list of research articles on demodectic rosacea www.irosacea.org/htmlidemodex_rosacea_research_papers.html

[14] Beating Rosacea Vascular, Ocular Acne Forms, page 110 Geoffrey Nase, Ph.D. Nase Publications 2001

[15] Mar. 28, 2007 R-S post by David Pascoe

[16] Rosacea Review, Fall 2010, NRS-Funded Studies Advance Knowledge of Rosacea's Causes

[17] Rosaceam Like Demodicidosis, SAMUEL AYRES, JR., M.D., Los AngelesCalifornia Medicine, June 1963

[18] Something to Blush About, Medical Breakthoughs, Ivanhoe Newswire, Dec. 11, 2007

[19] Rosacea Diagnosis and Management, pages 69, 70 by Frank C. Powell, Informa Healthcare, 2008

[20] Empirical treatment is key to identifying rosacea, other dermatoses, Modern Medician, John Jesitus, Nov. 1, 2007

[21] Demodicosis and rosacea: epidemiology and significance in daily dermatologic practice. Forton F, Germaux M A, Brasseur T, De Liever A, Laporte M, Mathys C, Sass U, Stene J J, Thibaut S, Tytgat M, Seys B. J Am Acad Dermatol. 2005 January; 52(1):74-87.

[22] A clinico-pathological approach to the classification of human demodicosis. Akilov O E, Butov Y S, Mumcuoglu K Y. J Dtsch Dermatol Ges. 2005 August; 3(8):607-14.

[23] Could matrix metalloproteinase-9 be a link between *Demodex folliculorum* and rosacea? R R Bonamigo, L Bakos1, M Edelweiss, A Cartell Journal of the European Academy of Dermatology & Venereology, Volume 19 Issue 5 Page 646—September 2005

[24] Is *demodex* really non-pathogenic? Pena G P, Andrade Filho J S Rev Inst Med Trop Sao Paulo. 2000 May-June; 42(3):171-3.

[25] Facial demodicosis. Zomorodian K, Geramishoar M, Saadat F, Tarazoie B, Norouzi M, Rezaie S. Eur J Dermatol. 2004 March-April; 14(2):121-2.

[26] Demodicidosis revisited. Baima B, Sticherling M. Acta Derm Venereol. 2002; 82(1):3-6

[27] Rosacea, eMedicine from WebMD Author: Agnieszka Kupiec Banasikowska, M D, Consulting Staff, George-

[28] Rosacea and the pilosebaceous follicle. Powell F C. Cutis. 2004 September; 74(3 Suppl):9-12, 32-4.

[29] Mite-related bacterial antigens stimulate inflammatory cells in rosacea. Lacey N, Delaney S, Kavanagh K, Powell F C. Br J Dermatol. 2007 September; 157(3):474-81. Epub 2007 Jun. 26

[30] New Study Shows Role for Bacteria in Development of Rosacea Symptoms National Rosacea Society, May 3, 2004

[31] Frequency of the appearance of *Demodex* sp. in various patient and age groups Aycan O M, Otlu G H, Karaman U, Daldal N, Atambay M. Turkiye Parazitol Derg. 2007; 31(2):115-8.

[32] Electronmicroscopic investigation into the possible etiology of rosacea and the implication for treatment Journal of the American Academy of Dermatology February 2007 (Vol. 56, Issue 2 (Supplement 2), Page AB44) Richard Burroughs, MD, National Capital Consortium (Walter Reed Army Medical Center), Washington, DC, United States; Kurt Maggio, MD, Walter Reed Army Medical Center, Washington, DC, United States

[33] A study on *Demodex folliculorum* in rosacea. Abd-EI-AI A M, Bayoumy A M, Abou Salem E A. J Egypt Soc Parasitol. 1997 April; 27(1):183-95.

[34] The pathogenesis of *Demodex folliculorum* (hair follicular mites) in females with and without rosacea. el-Shazly A M, Ghaneum B M, Morsy T A, Aaty H E. J Egypt Soc Parasitol. 2001 December; 31(3):867-75.

[35] *Demodex* mites in acne rosacea. Roihu T, Kariniemi A L. J Cutan Pathol. 1998 November; 25(10):550-2.

[36] The possible role of skin surface lipid in rosacea with epitheloid granulomas. Basta-Juzbasić A, Marinović T, Dobrić I, Bolanca-Bumber S, Sencar J. Acta Med *Croatica*. 1992; 46(2):119-23.

[37] Study finds cause of rosacea Claire O'Connell The Irish Times—Tuesday, Jul. 14, 2009

[38] New Study Shows Role for Bacteria in Development of Rosacea Symptoms NRS Press Release, May 3, 2004, Suzanne Corr/Barbara Palombo

[39] Mite-related bacterial antigens stimulate inflammatory cells in rosacea. Lacey N, Delaney S, Kavanagh K, Powell F C. Department of Biology, National University of Ireland, Maynooth, Co. Kildare, Ireland Br J Dermatol. 2007 September; 157(3):474-81

[40] Correlation between Ocular *Demodex* Infestation and Serum Immunoreactivity to *Bacillus* Proteins in Patients with Facial Rosacea, Li J, O'Reilly N, Sheha H, Katz R, Raju V K, Kavanagh K, Tseng S C. Ophthalmology. 2010 Jan. 14, Papulopustular rosacea, skin immunity and *Demodex: pityriasis folliculorum* as a missing link. Forton F M. J Eur Acad Dermatol Venereol. 2011 Oct. 24. doi: 10.1111/j.1468-3083.2011.04310.x. © 2011 The Author. Journal of the European Academy of Dermatology and Venereology © 2011 European Academy of Dermatology and Venereology. PMID: 22017468 [PubMed—as supplied by publisher]

[42] *Demodex* Infestation: the Missing Link ? Oct. 27, 2011, by David Pascoe

[43] *Demodex* Mites, Ivermectin (Stromectol) and its use in Dermatology Feb. 2, 2006, by David Pascoe

[44] Rosacea: Diagnosis and Management Frank Powell, MD, Informa Healthcare, 2008

[45] Intense Pulsed Light Eradicates *Demodex* Mites Timothy F. Kirn Sacramento Bureau, Sharon Worcester, Tallahassee bureau, contributed this story • Another source

[46] Rejecting common wisdom: Red, scaly faces not always rosacea or seborrheic dermatitis Dermatology Times, Modern Medicine, Jane Schwanke, Jun. 1, 2009

[47] Treatment of human *Demodex folliculorum* by camphor oil and metronidazole. EI-Shazly A M, Hassan A A, Soliman M, Morsy G H, Morsy T A. J Egypt Soc Parasitol. 2004 April; 34(1):107-16.

[48] *Eucalyptus globulus* (camphor oil) in the treatment of human demodicidosis. Morsy T A, Morsy G H, Sanad E M. J Egypt Soc Parasitol. 2002 December; 32(3):797-803

[49] Read the report in footnote [10] above

[50] Ivermectin: pharmacology and application in dermatology International Journal of Dermatology, Volume 44 Page 981—December 2005. Pharmacology and therapeutics; Assen L. Dourmishev, Lyubomir A. Dourmishev, and Robert A. Schwartz

[51] Natural remedies aid rosacea management, doctor says Dietary changes, supplements can lead to clearer skin Lisette Hilton, Dermatology Times, Modern Medicine, Dec. 1, 2004

[52] In vitro and in vivo killing of ocular *Demodex* by tea tree oil. Gao Y Y, Di Pascuale M A, Li W, Baradaran-Rafii A, Elizondo A, Kuo C L, Raju V K, Tseng S C Br J Ophthalmol. 2005 November; 89(11):1468-73.

[53] Lavender and Tea Tree Oils May Cause Breast Growth in Boys NIH News, Wednesday, Jan. 31, 2007

[54] Non-invasive in vivo detection and quantification of *Demodex* mites by confocal laser scanning microscopy. Sattler E C, Maier T, Hoffmann V S, Hegyi J, Ruzicka T, Berking C. Br J Dermatol. 2012 Jun. 20. doi: 10.1111/j.1365-2133.2012.11096.x.

[55] Counting *Demodex* Mites with a Confocal Laser Microscope David Pascoe Rosacea Support Group

[56] Wistar's comment on *demodex* testing post #4 Apr. 10, 2011 at 10:01 PM

[57] Unilateral demodectic rosacea. Shelley W B, Shelley E D, Burmeister V. J Am Acad Dermatol. 1989 May; 20(5 Pt 2):915-7.

[58] *Demodex* Dermatitis A Retrospective Analysis of Clinical Diagnosis and Successful Treatment with Topical Crotamiton Joseph B. Bikowski, MD, FAAD and James Q. Del Rosso, DO, FAOCD Journal List>J Clin Aesthet Dermatol>v.2(1); January 2009>PMC2958185

[59] The Chicken, not the Egg? National Rosacea Society, Thursday, Jul. 5, 2012

[60] More *Demodex* Dreaming: Mites are the Chicken? by David Pascoe, Jul. 24, 2012

[61] Br J Dermatol. 2013 Feb. 16. doi: 10.1111/bjd.12280. *Demodex* quantification methods: Limitations of Confocal Laser Scanning Microscopy (CLSM). Lacey N, Forton F M, Powell F C.

[62] Indian J Dermatol. 2013 March; 58(2):157. doi: 10.4103/0019-5154.108069. Evaluation of *Demodex folliculorum* as a Risk Factor for the Diagnosis of Rosacea In Skin Biopsies. Mexico's General Hospital (1975-2010). Rios-Yuil J M, Mercadillo-Perez P.

[63] The Quality of Life Impact of Acne and Rosacea Compared to Other Major Medical Conditions. Nicole D. Cresce B S, Scott A. Davis M A, William W. Huang MD MPH, Steven R. Feldman MD PhD. Journal of Drugs and Dermatology June 2014.

[64] An Evaluation of the Potential Correlations Between Pathophysiologic Mechanisms, Clinical Manifestaions, and Managemant of Rosacea. James Q. Del Rosso, DO; Richard L Gallo, MD, PhD; Emil Tanghetti, MD; Guy Webster, MD, PhD; Diane Thiboutot, MD. Cutanous Medicine For The Practicioner. vol. 91 no. 3s March 2013.

[65] Influence of temperature and medium on viability of *Demodex folliculorum* and *Demodex brevis*. Ya-E Zhao; Na Guo; Li-Ping Wu; Exp Appl Acarol (2011) 54:421-425

[66] The effect of temperature on the viability of *Demodex folliculorum* and *Demodex brevis*. Ya-E Zhao; Na Guo; Li-Ping Wu; Parasitol Research (2009) 105: 1623-1628 www.youtube.com/watch?v=r1-L79szJ6QMeature=related www.youtube.com/watch?feature=endscreen&NR=1&v=pZof6KvD88g www.youtube.com/watch?v=3LLk7CNIYdQ www.psmicrographs.co.uk/follicle-mite-*demodex-folliculorum*-/science-image/80016342

Are Mites Causing Your Rosacea?: http://www.webmd.com/skin-problems-and-treatments/news/20120830/are-mites-causing-your-rosacea Mites May Cause Rosacea and Botox May Cure Acne in Alluring Links: http://www.allure.com/beauty-trends/blogs/daily-beauty-reporter/2012/08/beauty-news-week-of-august-31.html Rosacea May Be Caused By Bacteria Released By Tiny Mites Living On The Skin: http://www.medicalnewstoday.com/releases/249664.php Could Bacteria in Skin Mites Help Cause Rosacea?: http://health.usnews.com/health-news/news/articles/2012/08/30/could-bacteria-in-skin-mites-help-cause-rosacea Bacterial Cause Found for Skin Condition Rosacea: http://members.rosacea-research-and-development-institute.org/topic/1297-demodectic-rosacea-in-the-media/

Tiny mites on your face may cause rosacea: http://vitals.nbcnews.comLnews/2012/08/29/13554038-tiny-mites-on-your-face-may-cause-rosacea?lite Rosacea: Caused by Mite Poop in Your Facial Pores?: http://healthland.time.com/2012/09/04/rosacea-caused-by-mite-poop-in-your-facial-pores/

Rosacea may be caused by mite faeces in your pores: http://www.newscientist.com/article/dn22227-rosacea-may-be-caused-by-mite-faeces-in-your-pores.html Bacteria-laden mites may cause rosacea: http://dermatologytimes.modernmedicine.com/dermatologytimes/Modern+Medicine+Ne ws/Bacteria-laden-mites-may-cause-rosacea/ArticleStandard/Article/detail/787502?ref=25

New discovery may hold clues to rosacea cure; Red bumps may be linked to mites living on the face: http://www.nydailynews.com/life-style/health/new-discovery-hold-clues-rosacea-cure-red-bumps-linked-mites-living-face-article-1.1152511#ixzz25klcWNDW Rosacea caused by bacteria from tiny mites?: http://abclocal.go.com/w1s/story?section=news/health&id=8792589

Health & Beauty: Could These Tiny Mites Be Causing Your Rosacea?: http://www.glamour.com/health-fitness/blogs/vitamin-g/2012/08/health-beauty-could-these-tiny.html#ixzz25kK66pNH Rosacea Comes From Mite Feces: http://www.theatlanticwire.com/technology/2012/08/strange-heartland-virus-discovered-rosacea-comes-mite-feces/56390/

That Rose in Your Cheeks Could Be Bacteria: http://abcnews.go.com/blogs/health/2012/08/29/that-rose-in-your-cheeks-could-be-bacteria/

Rosacea may be caused by skin bacteria: study: http://www.business-standard.com/generalnews/news/rosacea-may-be-caused-by-skin-bacteria-study/49985/

Researchers Claim to be Closer Towards Effective Treatment of Rosacea: http://www.business-standard.com/generalnews/news/rosacea-may-be-caused-by-ski n-bacteria-study/49985/

Face Bacteria Only Cause Deadly Skin Disease: http://frenchtribune.com/teneur/1213176-face-bacteria-only-cause-deadly-skin-disease The secret to rosacea: mite poop in you pores: http://www.smartplanet.com/blog/rethinking-healthcare/the-secret-to-rosacea-mite-poop-in-you-pores/9936

Rosacea caused by mite poop: http://www.theatlanticwire.com/technology/2012/08/strange-heartland-virus-discovered-rosacea-comes-mite-feces/56390/

Could Bacteria in Skin Mites Help Cause Rosacea?: http://www.newsday.com/news/health/could-bacteria-in-skin-mites-help-cause-rosacea-1.3938011

Rosacea may be caused by mite faeces in your pores: www.newscientist.com/article/dn22227-rosacea-may-be-caused-by-mite-faeces-in-your-pores.html Red skin condition rosacea may be due to bacteria in skin mites: www.cbsnews.com/8301-504763162-57503771-10391704/red-skin-condition-rosacea-may-be-due-to-bacteria-in-skin-mites/

Rosacea: A product of bacteria from mites?: http://www.foxnews.com/health/2013/02/05/rosacea-product-bacteria-from-mites/

Scientists Find Cause Of Rosacea, And It's Terrifying: http://www.buzzfeed.com/jtes/scientists-find-cause-of-rosacea-and-its-ter Indian J Dermatol. 2013 March; 58(2):157. doi: 10.4103/0019-5154.108069. Evaluation of *Demodex folliculorum* as a Risk Factor for the Diagnosis of Rosacea In Skin Biopsies. Mexico's General Hospital (1975-2010). Rios-Yuil J M, Mercadillo-Perez P.x.

Positive correlation between serum immuno-reactivity to *Demodex*-associated *Bacillus* proteins and Erythematotelangiectic Rosacea. O'Reilly N, Menezes N, Kavanagh K. Br J Dermatol. 2012 Jun. 18. doi: 10.1111/j.1365-2133.2012.11114.x.

Quantification of *Demodex folliculorum* by PCR in rosacea and its relationship to skin innate immune activation. Román-Curto C, Meseguer-Yebra C, Cañueto J, Fraile-Alonso C, Santos-Briz A, Vázquez L, Fernández-López E. Transpl Infect Dis. 2012 Apr. 9. doi: 10.1111/j.1399-3062.2012.00729.x Demodicidosis simulating acute graft-versus-host disease after allogeneic stem cell transplantation in one patient with acute lymphoblastic leukemia. Casas C, Paul C, Lahfa M, Livideanu B, Lejeune O, Alvarez-Georges S, Saint-Martory C, Degouy A, Mengeaud V, Ginisty H, Durbise E, Schmitt A M, Redoules D. Exp Dermatol. 2012 December; 21(12):906-10. doi: 10.1111/exd.12030

Risk factors and prevalence of *Demodex* mites in young adults. Horváth A, Neubrandt D M, Ghidán A, Nagy K Acta Microbiol Immunol Hung. 2011 June; 58(2):145-55.

*Demodex*-associated bacterial proteins induce neutrophil activation. O'Reilly N, Bergin D, Reeves E P, McElvaney N G, Kavanagh K. Br J Dermatol. 2011 Nov. 19. doi: 10.1111/j.1365-2133.2011.10746.x Papulopustular rosacea, skin immunity and *Demodex: pityriasis folliculorum* as a missing link. Forton F M. J Eur Acad Dermatol Venereol. 2011 Oct. 24. doi: 10.1111/j.14683083.2011.04310.x Retrospective analysis of the association between *demodex* infestation and rosacea. Zhao Y E, Wu L P, Peng Y, Cheng H. Arch Dermatol. 2010 August; 146(8):896-902.

Comparison of the two techniques for measurement of the density of *Demodex folliculorum*: standardized skin surface biopsy and direct microscopic examination. Askin U, Seçkin D. Br J Dermatol. 2010 Feb. 25

Correlation between Ocular *Demodex* Infestation and Serum Immunoreactivity to *Bacillus* Proteins in Patients with Facial Rosacea Li J, O'Reilly N, Sheha H, Katz R, Raju V K, Kavanagh K, Tseng S C. Ophthalmology. 2010 Jan. 14.

Pathogenic role of *Demodex* mites in blepharitis Jingbo Liu, Hosam Sheha, and Scheffer C. G. Tsegn Curr Opin Allergy Clin Immunol. 2010 October; 10(5): 505-510.

Demodicosis: a clinicopathological study. Hsu C K, Hsu M M, Lee J Y. J Am Acad Dermatol. 2009 March; 60(3): 453-62.

Under the lash *Demodex* mites in human diseases Noreen Lacey, Kevin Kavanagh, and Scheffer C. G. Tseng Biochem (Lond). 2009 August 1; 31(4): 2-6.

Facial *Demodex* infection among college students in Tangshan Cao Y S, You Q X, Wang L, Lan H B, Xu J, Zhang X H, Yang H, Xiong Y J, Tian X F. Laboratory of Medical Examination, Biosciences Department of North China Coal Medical University, Tangshan 063000, China. Zhongguo Ji Sheng Chong Xue Yu Ji Sheng Chong Bing Za Zhi. 2009 June; 27(3):271-3.

Rosacea-Like Demodicosis Induced by Topical Pimecrolimus: Immunohistochemical Evaluation of Inflammatory Infiltrate Efi Pasmatzi, MD, Maria Melachrinou, MD, Alexandra Monastirli1, MD, Anastasia Tzouma1, MD, Dionysios Tsambaosl, MD, PhD HOSPITAL CHRONICLES 2009, 4(4): 172-174

Rosacea-like demodicidosis. Larios G, Alevizos A, Perimeni D, Rigopoulos D, Katsambas A. Department of Dermatology, University of Athens Medical School, Andreas Sygros Hospital, Athens, Greece. Lancet Infect Dis. 2008 December; 8(12):804.

Clinical importance of *Demodex folliculorum* in patients receiving phototherapy. Kulac M, Ciftci I H, Karaca S, Cetinkaya Z Int J Dermatol. 2008 January; 47(1):72-7

Mite-related bacterial antigens stimulate inflammatory cells in rosacea. Lacey N, Delaney S, Kavanagh K, Powell F C. Department of Biology, National University of Ireland, Maynooth, Co. Kildare, Ireland. Br J Dermatol. 2007 Jun. 26

Rosacea. Author: Agnieszka Kupiec-Banasikowska, MD, Consulting Staff, Division of Dermatology, Georgetown University Medical Center Coauthor(s): Mana Ogholikhan, MD, Staff Physician, Division of Dermatology, Georgetown University Hospital; Ravi Ratnavel, MD, Consulting Staff, Department of Dermatology, Stoke Mandeville, Thames Valley Nuffield, Paddocks Hospitals, UK—2007

Association of rosacea with demodicosis. Moravvej H, Dehghan-Mangabadi M, Abbasian M R, Meshkat-Razavi G: Arch Iran Med. 2007 April; 10(2):199-203.

Corneal manifestations of ocular *demodex* infestation Kheirkhah A, Casas V, Li W, Raju V K, Tseng S C. Am J Ophthalmol. 2007 May; 143(5):743-749. Epub 2007 Mar. 21

Demoodex *folliculorum* and *Demodex brevis* as a cause of chronic marginal blepharitis. Czepita D, Ku?na-Grygiel W, Czepita M, Grobelny A. Ann Acad Med Stetin. 2007; 53(1):63-7; discussion 67.

Granulomatous rosacea-like demodicidos Julia Yu-Yun Lee MD, Chao-Kai Hsu MD Dermatology Online Journal 13 (4): 9; 2007, Vol 13, No. 1

Standardized skin surface biopsy: method to estimate the *Demodex folliculorum* density, not to study the *Demodex folliculorum* prevalence. Forton F. J Eur Acad Dermatol Venereol. 2007 October; 21(9):1301-2

Density of *Demodex folliculorum* in rosacea: a case-control study using standardized skin-surface biopsy. F. FORTON 1 B. SEYS. Clinic of Dermatology, Saint Pierre University Hospital, Université Libre de Bruxetles, Brussels, Belgium, Unit of Medical Sciences Pedagogy, Faculty of Medicine, Université Catholique de Louvain, Brussels, Belgium British Journal of Dermatology, Volume 128 Issue 6, Pages 650-659. Published Online: 29 Jul. 2006

Demodicosis and rosacea: Epidemiology and significance in daily dermatologic practice, Journal of the American Academy of Dermatology, Volume 52, Issue 1, January 2005, Pages 74-87, Forton F, Germaux M A, Brasseur T, De Liever A, Laporte M, Mathys C, Sass U, Stene J J, Thibaut S, Tytgat M, Seys B.

Structural and biological changes in rosacea skin induced by the 595 nm long-pulse dye laser and intense pulsed light. Dr. Payam Tristani-Firouzi, assistant professor, and Dr. Nancy Samolitis, visiting professor, department of dermatology, University of Utah. This study being done in 2005 by a grant from the NRS will study among other things and "assess the size of the oil glands and the presence of *Demodex* mites, normal inhabitants of human skin that have been observed in greater numbers in rosacea patients."

Demodecidosis in a patient infected by HIV: successful treatment with ivermectin. Clyti E, Sayavong K, Chanthavisouk K: Ann Dermatol Venereol. 2005 May; 132(5): 459-61. Service de Dermatologie, Institut Guyanais de Dermatologie Tropicale, Hopital de Cayenne, Guyane Francaise.

Density of *Demodex folliculorum* in perioral dermatitis. Dolenc-Voljc M, Pohar M, Lunder T: Acta Derm Venereol. 2005; 85(3):211-5: Department of Dermatovenereology, University Medical Centre Ljublana, Zaloska 2, SI-1525 Ljubluna, Slovenia.

Demodicidosis in humans as a current problem in dermatology: Wiad Parazytol. 2005; 51(3):253-6.

In vitro and in vivo killing of ocular *Demodex* by tea tree oil. Gao Y Y, Di Pascuale M A, Li W, Baradaran-Rafii A, Elizondo A, Kuo C L, Raju V K, Tseng S C: Br J Ophthalmol. 2005 November; 89(11):1468-73.

*Demodex* mites as a cause of human disease. Elston D M; Cutis. 2005 November; 76(5):294-6.

*Demodex* as an etiological factor in chronic blepharitis Czepita D, Ku?na-Grygiel W, Kosik-Bogacka D. Klin Oczna. 2005; 107(10-12):722-4.

Biochemical and immunological characterization of the role of bacterial antigens in the induction of papulopustular rosacea. Dr. Kevin Kavanagh, Department of biology, National University of Ireland, Maynooth, and Dr. Frank Powell, Consultant Dermatologist, Mater Misericordiae Hospital, Dublin. 2004. Dr. Kevin Kavanagh was awarded $25,000 to pursue further research on the potential role of bacterial antigens in papulopustular (subtype 2) rosacea. In an earlier NRS-funded study, he and his colleagues succeeded in isolating a bacterium from *Demodex folliculorum*, microscopic mites that are a common inhabitant of facial skin. The bacteria produced antigens that induced an inflammatory response in significantly more rosacea patients than controls. In the new study, they will determine whether the presence of the antigens is predictive of the onset of rosacea, in order to establish whether they play a significant role.

Relationship between the *Demodex* and bacteria infection in human rosacea. Hu Q, Wang Y, Tong L: Zhongguo Ji Sheng Chong Xue Yu Ji Sheng Chong Bing Za Zhi. 2004 Feb. 28; 22(1):50-3. Department of Parasitology, Medical college of Inner Mongolia National University, Tongliao 028041, China.

New Study Shows Role for Bacteria in Development of Rosacea Symptoms. Suzanne Corr/Barbara Palombo; PROVIDENCE, R.I. (May 3, 2004): National Rosacea Society Studies of di-n-butyl phthalate-OP emulsion in the treatment of demodicidosis. Xia H, Hu S F, Ma W J, Ge J H: Zhongguo Ji Sheng Chong Xue Yu Ji Sheng Chong Bing Za Zhi. 2004 August; 22(4):248-9. Department of Microbiology and Parasitology, Bengbu Medical College, Bengbu 233003, China.

Rosacea: a clinicopathological approach. Aroni K, Tsagroni E, Lazaris A C, Patsouris E, Agapitos E; Dermatology. 2004; 209(3):177-82. Department of Dermatopathology, School of Medicine, National and Kapodistrian University of Athens Immune response in demodicosis. Akilov O E, Mumcuoglu K Y; J Eur Acad Dermatol Venereol. 2004 July; 18(4): 440-4. Department of Dermatology, Cosmetology Hospital 'Aesthetics', Ekaterinburg, Russian Federation.

*Demodex* abscesses: clinical and therapeutic challenges. Schaller M, Sander C A, Plewig G: J Am Acad Dermatol. 2003 November; 49(5 Suppl):S272-4. Department of Dermatology and Allergology, University of Munich, Germany Some aspects of the skin infestation by *Demodex folliculorum* n; Wiad Parazytol. 2004; 50(1):41-54

*Demodex* abscesses: clinical and therapeutic challenges. Schaller M, Sander C A, Plewig G: J Am Acad Dermatol. 2003 November; 49(5 Suppl):S272-4. Department of Dermatology and Allergology, University of Munich, Germany.

Association between human demodicosis and HLA class I. Akilov O E, Mumcuoglu K Y: Clin Exp Dermatol. 2003 January; 28(1):70-3. Department of Dermatology, Cosmetology Hospital Aesthetics, Ekaterinburg, Russian Federation.

Rosaceiform dermatitis with follicular *Demodex* after treatment of facial atopic dermatitis with 1% pimecrolimus cream. Lubbe J, Stucky L, Saurat J H; Dermatology. 2003; 207(2):204-5

The role of bacterial antigen(s) in the etiology and persistence of papulopustular bacteria. Dr. Kevin Kavanagh, Department of Biology, National University of Ireland—Maynooth, and Dr. Frank Powell, consultant dermatologist, Mater Misericordiae Hospital, Dublin. 2002. Bacteria associated with microscopic mites known as *Demodex folliculorum* may play a role in the development of papulopustular (subtype 2) rosacea, according to the results of a study funded by a National Rosacea Society grant and reported at the 2004 annual meeting of the Society for Investigative Dermatology.

*Eucalyptus globulus* (camphor oil) in the treatment of human demodicidosis. Morsy T A, Morsy G H, Sanad E M: J Egypt Soc Parasitol. 2002 December; 32(3):797-803. Department of Parasitology, Faculty of Medicine, Ain Shams University, Cairo 11566, Egypt Rosacea and the pilosebaceous follicle. Powell F C: Cutis. 2004 September; 74(3 Suppl):9-12, 32-4. Regional Centre of Dermatology, Mater Misercordiae Hospital, Dublin, Ireland Demodicidosis revisited. Baima B, Sticherling M: Acta Derm Venereol. 2002; 82(1):3-6. Department of Dermatology, University of Leipzig, Germany.

Intense pulsed light eradicates *demodex* mites. (Improves Acne, Rosacea). Timothy F. Kirn, Skin & Allergy News, Jun. 1, 2002

Increased density of *Demodex folliculorum* and evidence of delayed hypersensitivity reaction in subjects with papulopustular rosacea. Georgala S, Katoulis A C, Kylafis G D, Koumantaki-Mathioudaki E, Georgala C, Aroni K; J Eur Acad Dermatol Venereol. 2001 September; 15(5):441-4; National University of Athens, Department of Dermatology and Venereology, A. Sygros' Hospital, Greece. 2001

Rosacea-like demodicidosis associated with acquired immunodeficiency syndrome. Jansen T, Kastner U, Kreuter A, Altmeyer P: Br J Dermatol. 2001 January; 144(1):139-42. Department of Dermatology and Allergology, Ruhr-University Bochum, Gudrunstrasse 56, 44791 Bochum, Germany. Full Text Rosacea, acne and other diseases of the seborrheic spectrum. Boni R: Schweiz Rundsch Med Prax. 2000 Mar. 30; 89(14):566-70; Dermatologische Klinik, UniversitatsSpital Zurich.

Rosacea, acne and other diseases of the seborrheic spectrum. Boni R: Schweiz Rundsch Med Prax. 2000 Mar. 30; 89(14):566-70. Dermatologische Klinik, UniversitatsSpital Zurich.

Treatment of rosacea-like demodicidosis with oral ivermectin and topical permethrin cream. JAAD, November 1999, part 1. Volume 41. Number 5 Christa Forstinger, MD, Harald Kittler, MD Michael Binder, MD Vienna, Austria, and Boston, Mass. (Full Report if you scroll down)

Unilateral demodicidosis. Pallotta S, Cianchini G, Martelloni E, Ferranti G, Girardelli C R, Di LeIla G, Puddu P: Eur J Dermatol. 1998 April-May; 8(3):191-2. Department of Immunoderma-tology, Istituto Dermopatico Dell Imma-colata, IRCCS, Via dei Monti di Creta 104, 00167 Rome, Italy.

The significance of *Demodex folliculorum* density in rosacea. Erbagci Z, Ozgortasi O: Int J Dermatol. 1998 June; 37(6):421-5. Department of Dermatology, Faculty of Medicine, Gaziantep University, Turkey.

*Demodex*-associated folliculitis. Forton F. Am J Dermatopathol. 1998 October; 20(5):536-7

Blepharitis. *Demodex folliculorum*, associated pathogen spectrum and specific therapy Demmler M; de Kaspar H M; Mohring C; Klauss V—Ophthalmologe—1997 March; 94(3): 191-6

Pilocarpine gel for the treatment of demodicosis—a case series. Fulk G W, Murphy B, Robins M D: Optom Vis Sci. 1996 December; 73(12):742-5. College of Optometry, Northeastern State University, Tahlequah, Okla., USA.

Demodicidosis in childhood acute lymphoblastic leukemia; an opportunistic infection occurring with immunosuppression. Ivy SP—Journal of Pediatrics—1995 November; 127(5): 751-4

Acne rosacea complicated with demodicosis. Bobrov V M; Vestn Otorinolaringol. 1994 July-August(4):43-4.

Rosacea. Decauchy F, Beauvais L, Meunier L, Meynadier J: Rev Prat. 1993 Nov. 15; 43(18):2344-8. Service de dermatologie allergologie et photobiologie, hopital Saint-Charles, Montpellier.

The *Demodex* mite population in rosacea. Bonnar E, Eustace P, Powell F C: J Am Acad Dermatol. 1993 March; 28(3):443-8.University Department of Ophthalmology, Mater Misercordiae Hospital, Dublin, Ireland.

Granulomatous rosacea associated with *Demodex folliculorum*. Amichai B, Grunwald M H, Avinoach I, Halevy S: Int J Dermatol. 1992 October; 31(10):718-9 Department of Dermatology, Soroka Medical Center of Kupat Holim, Beer-Sheva, Israel.

The possible role of skin surface lipid in rosacea with epitheloid granulomas. Basta-Juzbasic A, Marinovic T, Dobric I, Bolanca-Bumber S, Sencar J: Acta Med *Croatica*. 992; 46(2):119-23. University Department of Dermatology, Medical Faculty, University of Zagreb, Croatia.

Topical steroid induced chronic demodicidosis. Sakuntabhai A, Timpatanapong P: J Med Assoc Thai. 1991 February; 74(2):116-9. Department of Medicine, Faculty of Medicine, Ramathibodi Hospital, Mahidol University, Bangkok, Thailand Demodicosis, what to do about it? Vroom M W: Tijdschr Diergeneeskd. 1991 Mar. 15; 116(6):296-7.

Papular pruritic eruption with human immunodeficiency virus infection. Bañuls J, Ramon D, Aniz E, Jorda E, Torres V. Int J Dermatol. 1991 November; 30(11):801-3

Unilateral demodectic rosacea. Shelley W B, Shelley E D, Burmeister V. Department of Medicine, Medical College of Ohio, Toledo. J Am Acad Dermatol. 1989 May; 20 (5 Pt 2):915-7.

Papulonodular demodicidosis associated with acquired immunodeficiency syndrome. Dominey A, Rosen T, Tschen J. J Am Acad Dermatol. 1989 February; 20(2 Pt 1):197-201.

*Demodex* mites contain immunoreactive lipase. Jimenez-Acosta F, Planas L, Penneys N. Arch Dermatol. 1989 October; 125(10):1436-7

Rosacea: histopathologic study of 75 cases. Ramelet A A, Perroulaz G: Ann Dermatol Venereol. 1988; 115(8):801-6.

Service de dermatologie et de venereologie, CHUV, (Centre Hospitalier universitaire vaudois), Lausanne, Suisse. *Demodex folliculorum*. Huismans H: Klin Monatsbl Augenheilkd. 1988 September; 193(3):304-6

Rosacea and rosacea-like demodicidosis. Ayres S: Int J Dermatol. 1987 April; 26(3):198-9.

Demodicosis—a rosaceiform dermatosis. Wätzig V, Zollmann C: Dermatol Monatsschr. 1987; 173(3):158-62.

Clinical manifestations of demodicosis. Heacock C E: J Am Optom Assoc. 1986 December; 57(12):914-9.

T-cell subsets in acne rosacea lesions and the possible role of *Demodex folliculorum*. Rufli T, Buchner S A: Dermatologica. 1984; 169(1):1-5.

Ultrastructural study of *demodex* infestation of the face in healthy subjects and acne rosacea patients: G Ital Dermatol Venereol. 1982 September-October; 117(5):277-81. Crosti C, Menni S, Piccinno R, Sala F.

Nosologic position of demodicidosis in humans. Bardach H G, Raff M, Poitschek C: Hautarzt. 1981 October; 32(10): 512-8.

Demodicosis of ophthalmic concern. English F P, Nutting W B: Am J Ophthalmol. 1981 March; 91(3):362-72.

*Demodex folliculorum*: aetiopathogenesis and therapy of rosacea and perioral dermatitis. Rufli T, Mumcuoglu Y, Cajacob A, Büchner S. Dermatologica. 1981; 162(1):12-26.

*Demodex folliculorum* and rosacea: experimental and immunological studies. Grosshans E, Dungler T, Kien T T, Kremer M: Z Hautkr. 1980 Sep. 15; 55(18):1211-8.

Perioral dermatitis—an allergic disease? Arutjunow V: Hautarzt. 1978 February; 29(2):89-91.

Pyroglyphid mites, xerophilic fungi and allergenic activity in dust from hospital mattresses. v d Lustgraaf B, Jorde W: Acta Allergol. 1977 December; 32(6):406-12.

*Demodex folliculorum* in rosacea. Ayers S Jr, Mihan R, Marks R, Harcourt-Webster J N.

*Demodex folliculorum* and the histogenesis of granulomatous rosacea. Grosshans E M, Kremer M, Maleville J. Hautarzt. 1974 April; 25(4):166-77.

The role of the acarid *Demodex folliculorum* in ophthalmology. English F P: Trans Aust Coll Ophthalmol. 1970; 2:89-92.

The role of *demodex* mites in the development of acne rosacea. Kiselev O A: Vestn Dermatol Venerol. 1967 October; 41(10):90-1.

*Demodex folliculorum* in patients with rosacea. Baksht B P: Vestn Dermatol Venerol. 1966 August; 40(8):15-22.

*Demodex folliculorum* and rosacea. A clinical and histological study. Robinson T W: Arch Dermatol. 1965 November; 92(5):542-4.

DEMODICOSIS Ind. MAN. AKBULATOVA LKh: Vestn Dermatol Venerol. 1964 March; 38:34-42.

Rosacdea-Like Demodicidosis. Samuel Ayres, Jr. Calif Med. 1963 June; 98(6): 328-330. pdf download Demodectic eruptions (demodicidosis) in the human. 30 years' experience with 2 commonly unrecognized entities: *pityriasis folliculorum* (*Demodex*) and acne rosacea (*Demodex* type). AYRES S Jr, AYRES S 3rd: Arch Dermatol. 1961 May; 83:816-27.

Rosacea: the role of *Demodex folliculorum*. BRODIE RC: Aust J Dermatol. 1952 April; 1(3):149-52.

*Demodex Folliculorum* in Diseased Conditions of the Human Face. Geo. E. Fell Proceedings of the American Society of Microscopists Published by: Wiley-Blackwell on behalf of American Microscopical Society Optom Vis Sci. 2013 Jun. 6. *Demodex*. Hom M M, Mastrota K M, Schachter S E.

Non-invasive in vivo detection and quantification of *Demodex* mites by confocal laser scanning microscopy. Sattler E C, Maier T, Hoffmann V S, Hegyi J, Ruzicka T, Berking C. Br J Dermatol. 2012 Jun. 20. doi: 10.1111/j.1365-2133.2012.11096.x.

*Demodex*-associated *Bacillus* proteins induce an aberrant wound healing response in a corneal epithelial cell line (hTCEpi). O'Reilly N, Gallagher C, Katikireddy K, Clynes M, O'Sullivan F, Kavanagh K. Invest Ophthalmol Vis Sci. 2012 Apr. 24.

The potential role of *Demodex folliculorum* mites and bacteria in the induction of rosacea. Stanislaw Jarmuda, Niamh O'Reilly, Ryszard Zaba, Oliwia Jakubowicz, Andrzej Szkaradkiewicz and Kevin Kavanagh. Journal of Medical Microbiology, 2012 DOI: 10.1099/jmm.0.048090-0 Article at PubMed Facial dermatosis associated with *Demodex*: a case-control study. Zhao Y E, Peng Y, Wang X L, Wu L P, Wang M, Yan H L, Xiao S X. J Zhejiang Univ Sci B. 2011 December; 12(12):1008-15.

Density of *Demodex folliculorum* in Patients Receiving Epidermal Growth Factor Receptor Inhibitors. Gerber P A, Kukova G, Buhren B A, Homey B. Dermatology. 2011 February 22

Rosacea-like demodicidosis and chronic blepharitis. Anane S, Mokni M, Beltaief O. Ann Dermatol Venereol. 2011 January; 138(1):30-34.

*Demodex* mites: Facts and controversies. Elston D M. Clin Dermatol. 2010 September-October; 28(5):502-504.

Reaction to Mites May Mimic Rosacea Signs. NRS Rosacea Review, Winter 2010, Article 6 Mites and Eye Symptoms, NRS Web Blog Thursday, Jul. 15, 2010

Criotherapy in treatment of skin demodecosis. Georgian Med News. 2009 May; (170):43-5.

PCR analysis for *Wolbachia* in human and canine *Demodex* mites. Borgo S N, Sattler E C, Hogardt M, Adler K, Plewig G. Department of Dermatology and Allergology, Ludwig-Maximilian-University, Frauenlobstrasse 9-11, 80337, Munich, Germany. Arch Dermatol Res. 2009 Aug. 4

Rejecting common wisdom: Red, scaly faces not always rosacea or seborrheic dermatitis. Dermatology Times. Publish date: Jun. 1, 2009. By: Jane Schwanke Demodicosis. Manolette R Roque, M, Barbara L Roque, MD, eMedicine, WebMD Frequency of Demodicosis in various patient and age groups. Aycan O M, Otlu G H, Karaman U, Daldal N, Atambay M. Inönü Üniversitesi Tip Fakültesi, Parazitoloji Anabilim Dali, Malatya, Turkey. Turkiye Parazitol Derg. 2007; 31(2):115-118.

Electron microscopic investigation into the possible etiology of rosacea and the implication for treatment, Richard Burroughs, MD, National Capital Consortium (Walter Reed Army Medical Center), Washington, DC, United States; Kurt Maggio, MD, Walter Reed Army Medical Center, Washington, DC, United States., Poster Abstract P516, American Academy of Dermatology, 65th Annual Meeting Feb. 2-6, 2007, Washington, DC. Published in Journal of the American Academy of Dermatology Volume 56, Number 2.

Recalcitrant papulopustular rosacea in an immunocompetent patient responding to combination therapy with oral ivermectin and topical permethrin. Allen K J, Davis C L, Billings S. Dak., Mousdicas N; Cutis. 2007 August; 80(2):149-51

Clinical treatment of ocular demodecosis by lid scrub with tea tree oil. Gao Y Y, Di Pascuale M A, Elizondo A, Tseng S C. Cornea. 2007 February; 26(2):136-43.

Empirical treatment is key to identifying rosacea, other dermatoses. Modern Medicine—Publish date: Nov. 1, 2007. By: John Jesitu

*Demodex folliculorum* and *Demodex brevis* as a cause of chronic marginal blepharitis. Czepita D, Ku?na-Grygiel W, Czepita M, Grobelny A. Katedra i Klinika Okulistyki Pomorskiej Akademii Medycznej w Szczecinie al. Powsta?ców Wlkp. 72, 70-111 Szczecin. Ann Acad Med Stetin. 2007; 53(1):63-7; discussion 67.

Dispelling the Mystery of *Demodex*. Neal Bhatia, MD and James Q Del Rosso, DO, FAOCD US PHARMACY REVIEW 2006, p. 38-41

Could matrix metalloproteinase-9 be a link between *Demodex folliculorum* and rosacea? RR Bonamigo, L Bakos, M Edelweiss, A Cartell. Journal of the European Academy of Dermatology & Venereology. Volume 19 Page 646—September 2005, Volume 19 Issue 5

A clinico-pathological approach to the classification of human demodicosis. Akilov O E, Butov Y S, Mumcuoglu K Y: J Dtsch Dermatol Ges. 2005 August; 3(8):607-14. Department of Dermatology, Cosmetology Hospital "Aesthetics", Ekaterinburg, Russian Federation.

The role of HLA A2 and Cw2 in the pathogenesis of human demodicosis. Mumcuoglu K Y, Akilov O E: Dermatology. 2005; 210(2):109-14. Department of Parasitology, Hebrew University-Hadassah Medical School, Jerusalem, Israel.

Assen L. Dourmishev, Lyubomir A. Dourmishev, Robert A. Schwartz (2005) Ivermectin: pharmacology and application in dermatology. International Journal of Dermatology 44 (12), 981-988. doi:10.1111/j.1365-4632.2004.02253.x Topical application of 1-methylnicotinamide in the treatment of rosacea: a pilot study. Wozniacka A, Wieczorkowska M, Gebicki J, Sysa-Jedrzejowska A: Clin Exp Dermatol. 2005 November; 30(6):632-5. Department of Dermatology, Medical University of Lodz, Poland.

Rosacea and *Demodex*. Rufli T: J Dtsch Dermatol Ges. 2005 August; 3 (8):585-6.

[Investigations on the occurrence as well as the role of *Demodex* follicuforum and *Demodex brevis* in the pathogensis of blepharitis]. Czepita D, Ku?na-Grygiel W, Kosik-Bogacka D. Klin Oczna. 2005; 107(1-3):80-2

Consider *Demodex* mites regardless of immune status. Skin; Allergy News, September, 2005 by Patrice Wendling Rosacea: I. Etiology, pathogenesis, and subtype classification. Crawford G H, Pelle M T, James W D. Department of Dermatology, University of Pennsylvania Medical Center, USA: J Am Acad Dermatol. 2004 September; 51(3):327-41; quiz 342-4.

Rosacea and the pilosebaceous follicle. Powell F C: Cutis. 2004 September; 74(3 Suppl):9-12, 32-4. Regional Centre of Dermatology, Mater Misercordiae Hospital, Dublin, Ireland.

The clinical importance of *Demodex folliculorum* presenting with nonspecific facial signs and symptoms. Karincaoglu Y, Bayram N, Aycan O, Esrefoglu M: J Dermatol. 2004 August; 31(8):618-26.

Efficiency of benzoyl peroxide-erythromycin gel in comparison with metronidazole gel in the treatment of acne rosacea. Ozturkcan S, Ermertcan A T, Sahin M T, Afsar F S; J Dermatol. 2004 August; 31(8):610-7; Department of Dermatology, Medical Faculty of Celal Bayar University, Manisa, Turkiye.

Facial demodicosis. Zomorodian K, Geramishoar M, Saadat F, Tarazoie B, Norouzi M, Rezaie S; Eur J Dermatol. 2004 March-April; 14(2):121-2. Div. of Molecular Biology, Dept. of Medical Mycology & Parasitology, School of Public Health and Institute of Public Health Research, Tehran University of Medical Sciences, P.O. Box 14155, 64410 Tehran, Iran.

Treatment of human *Demodex folliculorum* by camphor oil and metronidazole. EI-Shazly A M, Hassan A A, Soliman M, Morsy G H, Morsy T A; J Egypt Soc Parasitol. 2004 April; 34(1):107-16. Departments of Parasitology, Faculty of Medicine, Mansoura University, Mansoura, Egypt.

Induction of rosaceiform dermatitis during treatment of facial inflammatory dermatoses with tacrolimus ointment. Antille C, Saurat J H, Lubbe J; Arch Dermatol. 2004 April; 140(4):457-60. Department of Dermatology, University Hospital, Geneva, Switzerland.

It's Enough To Make Your Skin Crawl: Microscopic Mites May Be Linked To Acne, Thinning Hair And Other Skin Disorders. Chuck Woods: Apr. 23, 2003. University of Florida's Institute of Food and Agricultural Sciences Is permethrin 5% cream effective for rosacea? Swenor M E: J Fam Pract. 2003 March; 52(3):183-4. Harrisburg Family Practice, Residency Program, PinnacleHealth Hospitals, Pa, USA Symbiotic intraceullular bacteria of *Demodex folliculorum* and the pathogenesis of rosacea. Drs. Richard Burroughs, Mark Peake and Richard Vinson, of William Beaumont Army Medical Center; Dr. Scott Norton, chief, Dermatology Service, Walter Reed Army Medical Center; and Dr. John Werren, professor of biology, and Seth Bordenstein, University of Rochester.

The researchers were awarded $12,250 to test *Demodex* from rosacea patients for the presence of bacteria, and analyze data for a possible statistical or clinical link between the bacteria and the presence of rosacea. They hypothesize that the cutaneous changes of rosacea may be due to an inflammatory response to bacteria within *Demodex* rather than the mite itself. Status: Interim report submitted April 2003. Study continues [editor's note: what happened to this report? Why pay this and wait this long for a final report?]

Effects of intense pulsed light on sun-damaged human skin, routine, and ultrastructural analysis. Prieto V G, Sadick N S, Lloreta J, Nicholson J, Shea C R: Lasers Surg Med. 2002; 30(2):82. Department of Pathology, UT-MD Anderson Cancer Center, Houston, Tex. 77030, USA.

The management of rosacea. Rebora A: Am J Clin Dermatol. 2002; 3(7):489-96. Department of Endocrinological and Metabolic Diseases, Section of Dermatology, University of Genoa, Genoa, Italy.

Permethrin 5% cream versus metronidazole 0.75% gel for the treatment of papulopustular rosacea. A randomized double-blind placebo-controlled study. Kocak M, Yagli S, Vahapoglu G, Eksioglu M: Dermatology. 2002; 205(3): 265-70. Department of Dermatology, Kirikkale University, Faculty of Medicine, Kirikkale, Turkey.

*Demodex folliculorum* in development of dermatitis rosaceiformis steroidica and rosacea-related diseases. Basta-Juzbasi? A, Subi? J S, Ljubojevi? S. Clin Dermatol. 2002 March-April; 20(2):135-40.

The pathogenesis of *Demodex folliculorum* (hair follicular mites) in females with and without rosacea. el-Shazly A M, Ghaneum B M, Morsy T A, Aaty H E: J Egypt Soc Parasitol. 2001 December; 31(3):867-75. Department of Parasitology, Faculty of Medicine, Mansoura University, Egypt.

Is *demodex* really non-pathogenic? Pena G P, Andrade Filho J S: Rev Inst Med Trop Sao Paulo. 2000 May-June; 42(3):171-3. Laboratorio Distrital Centro-Sul, Prefeitura de Belo Horizonte, Minas Gerais, Brasil Tubero-pustular demodicosis. Grossmann B, Jung K, Linse R. Hautarzt. 1999 July; 50(7):491-4.

Limitations of standardized skin surface biopsy in measurement of the density of *Demodex folliculorum*. A case report. Forton F, Song M: Br J Dermatol. 1998 October; 139(4):697-700. Clinic of Dermatology, Universite Libre de Bruxelles, Saint Pierre University Hospital, Brussels, Belgium

*Demodex* mites in acne rosacea. Roihu T, Kariniemi A L: J Cutan Pathol. 1998 November; 25(10):550-2. Department of Dermatology, Helsinki University Central Hospital, Finland.

*Demodex folliculorum* and topical treatment: acaricidal action evaluated by standardized skin surface biopsy. Forton F, Seys B, Marchal J L, Song A M. Br J Dermatol. 1998 March; 138(3):461-6.

A study on *Demodex folliculorum* in rosacea. Abd-EI-AI A M, Bayoumy A M, Abou Salem E A: J Egypt Soc Parasitol. 1997 April; 27(1):183-95. Department of Dermatology, Faculty of Medicine, Al-Azhar University, Nasr City, Cairo Rosacea-like demodicosis in an HIV-positive child. Barrio J, Lecona M, Hernanz J M, Sanchez M, Gurbindo M D, Lazaro P, Barrio J L: Dermatology. 1996; 192(2):143-5. Dermatology, Service, Hospital General Universitario Gregorio Maranon, Madrid, Spain.

Demodicidosis or rosacea: what did we treat? Hoekzema R, Hulsebosch H J, Bos J D: Br J Dermatol. 1995 August; 133(2):294-9. Department of Dermatology, Academisch Medisch Centrum, University of Amsterdam, The Netherlands.

*Demodex* mites in rosacea. Diaz-Perez J L: J Am Acad Dermatol. 1994 May; 30(5 Pt 1):812-3.

*Demodex*-attributed rosacea-like lesions in AIDS. Redondo Mateo J, Soto Guzmán O, Fernández Rubio E, Domínguez Franjo F: Acta Derm Venereol. 1993 December; 73(6):437.

Density of *Demodex folliculorum* in rosacea: a case-control study using standardized skin-surface biopsy. Forton F, Seys B. Br J Dermatol 1993; 128:650-9.

Rosacea: a study of clinical patterns, blood flow, and the role of *Demodex folliculorum*. Sibenge S, Gawkrodger D J: J Am Acad Dermatol. 1992 April; 26(4):590-3. Department of Dermatology, University of Sheffield, Royal Hallamshire Hospital, U.K.

Demodicidosis in a child with leukemia. Sahn E E, Sheridan D M. J Am Acad Dermatol. 1992 November; 27(5 Pt 2):799-801.

Demodicosis and rosacea. Skrlin J, Richter B, Basta-Juzbasic A, Matica B, Ivacic B, Cvrlje M, Kucisec N, Baucic A: 1991 Mar. 23; 337(8743):734.

[*Demodex folliculorum* and *Demodex brevis* (Acarida) as the factors of chronic marginal blepharitis] Humiczewska M. Wiad Parazytol. 1991; 37(1):127-30.

Papular pruritic eruption of *Demodex* folliculitis in patients with acquired immunodeficiency syndrome. Ashack R J, Frost M L, Norins A L. J Am Acad Dermatol. 1989 August; 21(2 Pt 1):306-7

*Pityriasis folliculorum* revisited. Dominey A, Tschen J, Rosen T, Batres E, Stern J K. J Am Acad Dermatol. 1989 July; 21(1):81-4.

The hair follicle mites (*Demodex* spp.). Could they be vectors of pathogenic microorganisms? Wolf R, Ophir J, Avigad J, Lengy J, Krakowski A: Acta Derm Venereol. 1988; 68(6):535-7. Department of Dermatology, Ichilov Medical Center, Tel-Aviv, Israel.

Demodicidosis mimicking granulomatous rosacea and transient acantholytic dermatosis (Grover's disease). Lindmaier A, Jurecka W, Lindemayr H: Dermatologica. 1987; 175(4):200-4.

*Demodex* and perifollicular inflammation in man: review and report of 69 biopsies. Forton F. Ann Dermatol Venereol. 1986; 113(11):1047-58

Rosacea and demodicosis (a review of the literature) Glukhen'ki? BT, Snitsanenko O V. Vrachebnoe Delo. 1984 February; (2):94-6.

The hair follicle mites *Demodex folliculorum* and *Demodex brevis*: biology and medical importance. A review. Rufli T, Mumcuoglu Y. Dermatologica. 1981; 162(1):1-11.

Metronidazole and *Demodex folliculorum*. Persi A, Rebora A: Acta Derm Venereol. 1981; 61(2):182-3

Pathogenesis associated with hair follicle mites (*Demodex* spp.) in Australian *Aborigines*. Nutting W B, Green A C: Br J Dermatol. 1976 March; 94(3):307-12.

Demodecidosis and rosaceiform dermatitis. Hojyo Tomoka M T, Dominguez Soto L: Med Cutan Ibero Lat Am. 1976; 4(2):83-90.

Rosacea-like demodicidosis involving the eyelids. A case report. Ayres S, Mihan R: Arch Dermatol. 1967 January; 95(1):63-6.

The pathogenic role of the mite *Demodex* and the clinical forms of demodicosis in man. Akbulatova LKh: Vestn Dermatol Venerol. 1966 December; 40(12):57-61.

U.S. Patent Application Publication No. 2011/0033395; U.S. Pat. Nos. 5,952,372 and 5,629,300; PCT Pub. WO 2009/010754; EP Pub. EP2355790

I claim:

1. A method of treating a mite-induced skin affliction comprising a step of topically applying to an individual having the skin affliction an organophosphate in a dosage sufficient to inactivate mites from hair follicles or skin of said individual, resulting in attenuation or cessation of a one or more clinical symptom of the skin affliction, wherein the mites are *Demodex brevis* mites, *Demodex folliculorum* mites, or both; and the organophosphate is an organophosphate acetylcholinesterase inhibitor and the organophosphate is metrifonate or a prodrug or pharmaceutically acceptable salt or ester thereof.

2. The method of claim 1, wherein the one or more clinical symptom is associated with an allergic and/or vasomotor response to the mites that cause the skin affliction or symptoms thereof.

3. The method of claim 1, wherein said organophosphate is provided at said dosage sufficient to kill said *Demodex brevis* mites, *Demodex folliculorum* mites or both from hair follicles and/or skin of the individual contacted with said organophosphate.

4. The method of claim 1, wherein said organophosphate is provided to said individual at said dosage is sufficient to provide a reduction in the population of said *Demodex brevis* mites, *Demodex folliculorum* mites or both from said hair follicles or skin contacted with said organophosphate greater than or equal to 80%.

5. The method of claim 4, wherein said reduction in the population is by one or more of: killing adult mites; killing mite larva; or affecting a fertilized egg to prevent emergence of a viable larva.

6. The method of claim 4, wherein said dosage is sufficient to provide for said reduction in the population of said *Demodex brevis* mites, *demodex folliculorum* mites or both over a time interval less than or equal to 1 month 1 month.

7. The method of claim 4, further comprising re-applying said organophosphate in a dosage sufficient to maintain said reduction in said population of said *Demodex brevis* mites, *Demodex folliculorum* mites or both over a time interval greater than or equal to two months.

8. The method of claim 7, wherein the re-applying is synchronized with a life cycle of the mites so as to inactivate a second generation of mites that were in an egg or larval form during the initial topically applying step and before a substantial portion of the second generation of mites are capable of reproducing.

9. The method of claim 8, further comprising re-applying a second time, wherein the time interval between temporally adjacent applications is independently selected over a time that is greater than or equal to 3 days and less than or equal to 7 days.

10. The method of claim 1, wherein said organophosphate is provided at said dosage sufficient to render said *Demodex brevis* mites, *Demodex folliculorum* mites or both incapable of reproducing in or on hair follicles and/or skin of the individual contacted with said organophosphate.

11. The method of claim 1, wherein said organophosphate is provided at said dosage sufficient to fill pores of said skin, hair follicles or both of the individual contacted with said organophosphate.

12. The method of claim 1, wherein the skin affliction affects facial skin or eyelids, or both.

13. The method of claim 1, wherein the skin affliction is one or more of: common acne, seborrheic dermatitis, perioral dermatitis, an acneform rash, transient acantholytic dermatosis, acne necrotica milliaris, psoriasis, steroid induced dermatitis, primary irritation dermatitis or rosacea.

14. The method of claim 1, wherein the skin affliction is rosacea.

15. The method of claim 1, wherein the skin affliction is erythematotelangiectatic rosacea, papulopustular rosacea, phymatous rosacea, ocular rosacea or rhinophyma.

16. The method of claim 1, wherein the skin affliction is acne vulgaris.

17. The method of claim 1, wherein said organophosphate is a miticide or an insecticide.

18. The method of claim 17, wherein said organophosphate kills *demodex brevis* mites, *Demodex folliculorum* mites or both.

19. The method of claim 1, wherein said organophosphate is transported into an epidermis or a subdermal region upon contact with said hair follicles and/or skin of the individual.

20. The method of claim 19, wherein said organophosphate is characterized by a transport rate into said epidermis or a subdermal region upon contact with said hair follicles and/or skin of the individual equal to or greater than 0.1 microns per second or a biological half-life less than or equal to 15 minutes.

21. The method of claim 1, wherein the organophosphate is metrifonate.

22. The method of claim 1, wherein the organophosphate is metrifonate or a pharmaceutically acceptable salt or ester thereof.

23. The method of claim 1, wherein the organophosphate topically applied as formulated in a carrier lotion, cream, soap, wash, shampoo or gel.

24. The method of claim 23, wherein the organophosphate: has a concentration in the topically applied carrier lotion, cream, soap, wash, shampoo or gel selected from the range 0.001 to 5 percent by weight; is provided in a lowest concentration effective for killing the *Demodex brevis* mites, *Demodex folliculorum* mites or both; is provided in the topically applied carrier lotion, cream, soap, wash, shampoo or gel at a dosage less than 150 mg/kg of body mass; is encapsulated inside microliposomes or micelles; or is provided as an emulsion in said topically applied lotion, cream, soap, wash, shampoo or gel.

25. The method of claim 1, comprising topically applying said organophosphate to skin areas exhibiting the clinical symptom.

26. The method of claim 25, further comprising topically applying said organophosphate to skin areas not exhibiting the clinical symptom.

27. The method of claim 1, comprising topically applying said organophosphate to skin and hair areas of the body where *Demodex brevis* mite or *Demodex folliculorum* mites are present.

28. The method of claim 1, comprising: topically applying said organophosphate to all skin areas of said individual; topically applying said organophosphate to all hair areas of said individual; applying the organophosphate to the individual's clothing, linens or both clothing and linens; or topically applying the organophosphate to others having contact with the individual in a dosage sufficient to inactivate *Demodex brevis* mites, *Demodex folliculorum* mites or both from hair follicles or skin of the others.

29. The method of claim 1, wherein the topically applied organophosphate penetrates an outer layer of the skin of the individual, thereby exposing the *Demodex brevis* mites, *Demodex folliculorum* mites or both present below the outer layer of the skin to the organophosphate.

30. The method of claim 1, wherein the topically applied organophosphate is applied to affected skin areas at least once and not more than twice daily for a period of two to twelve weeks.

31. The method of claim 1, wherein the topically applied organophosphate is applied to the affected skin areas and/or to non-affected skin areas during a first application period, thereby inactivating said *Demodex brevis* mites, *Demodex folliculorum* mites or both from the hair follicles in the skin of the individual.

32. The method of claim 31, wherein the topically applied organophosphate is further applied to the affected skin areas and/or to non-affected skin areas during a second application period, thereby inactivating said *Demodex brevis* mites, *Demodex folliculorum* mites or both from the hair follicles and/or skin of the individual that have matured from a larval form and/or an egg form present on and/or in the skin during or after the first application period.

33. The method of claim 32, wherein the topically applied organophosphate is further applied to the affected skin areas and/or to non-affected skin areas during a third application period, thereby inactivating said *Demodex brevis* mites, *Demodex folliculorum* mites or both from the hair follicles and or skin of the individual *Demodex brevis* and/or *Demodex folliculorum* mites that have matured from a larval form and/or an egg form present on and/or in the skin and/or the hair follicles during or after the first application period and/or the second application period.

34. The method of claim 32, wherein the first application period and the second application period are separated by at least three days and not more than seven days.

35. The method of claim 32, wherein the first application period and the second application period are separated by at least three days.

36. The method of claim 32, wherein the first application period and the second application period are separated by a time sufficient to allow larva of said *Demodex brevis* mites, *Demodex folliculorum* mites or both to mature into an adult form and/or to allow eggs of said *Demodex brevis* mites, *Demodex folliculorum* mites or both to mature into the adult form.

37. The method of claim 33, wherein the second application period and the third application period are separated by at least three days and not more than seven days.

38. The method of claim 33, wherein the second application period and the third application period are separated by at least three days.

39. The method claim 33, wherein the second application period and the third application period are separated by a time sufficient to allow larva of said *Demodex brevis* mites, *Demodex folliculorum* mites or both to mature into an adult form and/or to allow eggs of said *Demodex brevis* mites, *demodex folliculorum* mites or both to mature into the adult form.

40. The method of claim 1, wherein the organophosphate is topically applied in a continued intermittent regime sufficient for prophylactic control of *demodex* mite population in the hair follicles and/or skin of the individual.

41. The method of claim 1, wherein the inactivation of the *Demodex brevis* and/or *Demodex folliculorum* mites from hair follicles and/or skin of the individual results in a reduction in population of one or more bacteria in the hair follicles and/or skin of the individual.

42. The method of claim 2, wherein the manifestations of allergic and/or vasomotor responses to the mites result from a presence of one or more bacteria associated with the mites in the hair follicles and/or skin of the individual.

43. The method of claim 42, wherein the one or more bacteria comprise one or more bacteria from the genus *staphylococcus* or from the genus *bacillus*.

44. The method of claim 42, wherein the one or more bacteria comprise *Bacillus oleronius*.

45. The method of claim 42, wherein the one or more bacteria comprise *Staphylococcus epidermidis*.

46. The method of claim 42, wherein the one or more bacteria are present in a digestive system of the *Demodex brevis* and/or *demodex folliculorum* mites.

47. A method of treating a mite-induced skin affliction comprising a step of topically applying an active ingredient in a dosage to an individual having the skin affliction to inactivate *Demodex brevis* mites, *demodex folliculorum* mites or both from hair follicles or skin of said individual, resulting in attenuation or cessation of a clinical symptom associated with the skin affliction, wherein the topically applied active ingredient is applied to skin areas exhibiting the clinical symptom and to skin areas not exhibiting the clinical symptom;
  wherein the active ingredient comprises an organophosphate that is an organophosphate acetylcholinesterase inhibitor and the organophosphate is metrifonate or a pharmaceutically acceptable salt or ester thereof.

48. The method of claim 47, wherein the clinical symptom is a manifestation of allergic and/or vasomotor responses to the *Demodex brevis* mites, *demodex folliculorum* mites or both *Demodex brevis* mites and *Demodex folliculorum* mites.

49. The method of claim 47, wherein the topically applied active ingredient is applied to all skin of the individual to inactivate *Demodex brevis* mites, *demodex folliculorum* mites or both from all skin of the individual.

50. The method of claim 47, wherein the active ingredient is formulated in a shampoo or body-wash and the shampoo or body-wash is applied to at least 50% of the total surface area of skin of the individual.

51. The method of claim 47, wherein the active ingredient comprises metrifonate.

52. The method of claim 47, wherein said organophosphate kills *Demodex brevis* mites, *Demodex folliculorum* mites or both.

53. The method of claim 47, wherein the skin affliction comprises one or more of common acne, seborrheic dermatitis, perioral dermatitis, an acneform rash, transient acantholytic dermatosis, acne necrotica milliaris, steroid induced dermatitis, primary irritation dermatitis or rosacea.

54. The method of claim 47, further comprising co-administration or post-administration with intense light or intense pulsed light.

55. The method of claim 47, wherein the method of treating is for a human patient.

* * * * *

UNITED STATES PATENT AND TRADEMARK OFFICE
CERTIFICATE OF CORRECTION

PATENT NO. : 10,709,135 B2
APPLICATION NO. : 14/444748
DATED : July 14, 2020
INVENTOR(S) : Frank Anthony Spallitta Page 1 of 1

It is certified that error appears in the above-identified patent and that said Letters Patent is hereby corrected as shown below:

In Claim 6, Column 69, Line 38, replace "1 month 1 month" with --1 month--.

In Claim 13, Column 70, Line 2, delete "psoriasis,".

Signed and Sealed this
Tenth Day of November, 2020

Andrei Iancu
*Director of the United States Patent and Trademark Office*